(12) United States Patent
Vandenberghe et al.

(10) Patent No.: US 12,134,786 B2
(45) Date of Patent: Nov. 5, 2024

(54) METHODS OF PREDICTING ANCESTRAL VIRUS SEQUENCES AND USES THEREOF

(71) Applicants: Massachusetts Eye and Ear Infirmary, Boston, MA (US); The Schepens Eye Research Institute, Inc., Boston, MA (US)

(72) Inventors: Luk H. Vandenberghe, Weston, MA (US); Eric Zinn, Lynn, MA (US)

(73) Assignees: Schepens Eye Research Institute, Inc., Boston, MA (US); Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 18/308,590

(22) Filed: Apr. 27, 2023

(65) Prior Publication Data

US 2023/0287359 A1    Sep. 14, 2023

Related U.S. Application Data

(60) Division of application No. 17/408,104, filed on Aug. 20, 2021, which is a division of application No.
(Continued)

(51) Int. Cl.
*A61K 39/23* (2006.01)
*A61K 39/00* (2006.01)
(Continued)

(52) U.S. Cl.
CPC ............... *C12N 7/00* (2013.01); *A61K 39/00* (2013.01); *C07K 14/00* (2013.01); *C07K 14/005* (2013.01); *C07K 16/22* (2013.01); *C12N 15/86* (2013.01); *A61K 2039/525* (2013.01); *A61K 2039/6075* (2013.01); *C07K 2317/24* (2013.01); *C07K 2317/76* (2013.01); *C12N 2750/14121* (2013.01); *C12N 2750/14122* (2013.01); *C12N 2750/14123* (2013.01);
(Continued)

(58) Field of Classification Search
None
See application file for complete search history.

(56) References Cited

U.S. PATENT DOCUMENTS

| 5,037,384 | A | 8/1991 | Chang |
| 5,817,075 | A | 10/1998 | Giungo |

(Continued)

FOREIGN PATENT DOCUMENTS

| CA | 2193802 | 1/1996 |
| CN | 1826414 | 8/2006 |

(Continued)

OTHER PUBLICATIONS

Office Action in New Zealand Appln. No. 739476, dated Apr. 18, 2024, 4 pages.

(Continued)

*Primary Examiner* — M Franco G Salvoza
(74) *Attorney, Agent, or Firm* — Fish & Richardson P.C.

(57) ABSTRACT

Methods are described for predicting ancestral sequences for viruses or portions thereof. Also described are predicted ancestral sequences for adeno-associated virus (AAV) capsid polypeptides. The disclosure also provides methods of gene transfer and methods of vaccinating subjects by administering a target antigen operably linked to the AAV capsid polypeptides.

21 Claims, 23 Drawing Sheets

Specification includes a Sequence Listing.

Related U.S. Application Data

16/906,849, filed on Jun. 19, 2020, now Pat. No. 11,466,258, which is a continuation of application No. 16/717,942, filed on Dec. 17, 2019, now Pat. No. 11,104,885, which is a division of application No. 16/179,524, filed on Nov. 2, 2018, now Pat. No. 10,526,584, which is a division of application No. 15/633,292, filed on Jun. 26, 2017, now Pat. No. 10,119,125, which is a division of application No. 15/291,470, filed on Oct. 12, 2016, now Pat. No. 9,719,070, which is a division of application No. 15/095,856, filed on Apr. 11, 2016, now Pat. No. 9,695,220, which is a continuation-in-part of application No. PCT/US2014/060163, filed on Oct. 10, 2014.

(60) Provisional application No. 61/889,827, filed on Oct. 11, 2013.

(51) Int. Cl.

| | | |
|---|---|---|
| *C07K 14/00* | (2006.01) | |
| *C07K 14/005* | (2006.01) | |
| *C07K 16/22* | (2006.01) | |
| *C12N 7/00* | (2006.01) | |
| *C12N 15/86* | (2006.01) | |

(52) U.S. Cl.
CPC .............. *C12N 2750/14141* (2013.01); *C12N 2750/14142* (2013.01); *C12N 2750/14143* (2013.01); *C12N 2750/14171* (2013.01)

(56) References Cited

U.S. PATENT DOCUMENTS

| | | | |
|---|---|---|---|
| 7,906,111 | B2 | 3/2011 | Wilson et al. |
| 9,782,232 | B1 | 10/2017 | Papac |
| 10,738,087 | B2 | 8/2020 | Vandenberghe et al. |
| 11,034,732 | B2 | 6/2021 | Vandenberghe et al. |
| 2001/0014788 | A1 | 8/2001 | Morris |
| 2002/0106729 | A1 | 8/2002 | Bleck |
| 2004/0216750 | A1 | 11/2004 | Snyder et al. |
| 2007/0028928 | A1 | 2/2007 | Peyman |
| 2007/0225727 | A1 | 9/2007 | Matsuhisa et al. |
| 2008/0090914 | A1 | 4/2008 | Enaida et al. |
| 2009/0226531 | A1 | 9/2009 | Lyons |
| 2011/0098536 | A1 | 4/2011 | Corcosteugi et al. |
| 2012/0093772 | A1 | 4/2012 | Horsager et al. |
| 2013/0095071 | A1 | 4/2013 | Bance et al. |
| 2014/0248231 | A1 | 9/2014 | Askari et al. |
| 2015/0182756 | A1 | 7/2015 | Peyman |
| 2015/0283265 | A1 | 10/2015 | Peyman |
| 2015/0374543 | A1 | 12/2015 | Shapiro et al. |
| 2016/0296221 | A1 | 10/2016 | Morris |
| 2019/0254870 | A1 | 8/2019 | Hopkins |
| 2021/0371471 | A1 | 12/2021 | McCoy et al. |

FOREIGN PATENT DOCUMENTS

| | | |
|---|---|---|
| JP | 2007-500518 | 1/2007 |
| WO | WO 2003/089612 | 10/2003 |
| WO | WO 2005/033321 | 4/2005 |
| WO | WO 2006/110689 | 10/2006 |
| WO | WO 2010/136549 | 12/2010 |
| WO | WO 2014/160092 | 10/2014 |
| WO | WO 2015/054653 | 4/2015 |
| WO | WO 2018/119330 | 6/2018 |
| WO | WO 2020/069461 | 4/2020 |
| WO | WO 2021/154923 | 8/2021 |
| WO | WO 2022/150634 | 7/2022 |

OTHER PUBLICATIONS

Office Action in New Zealand Appln. No. 778484, dated Apr. 22, 2024, 4 pages.

[No Author Listed], "American Society of Gene & Cell Therapy 17th Annual Meeting," Molecular Therapy, May 1, 2014, 22(Supplement 1): S1-S305.

Adachi et al., "MOLPHY: Programs for Molecular Phylogenetics based on Maximum Likelihood," Tokyo Institute of Statistical Mathematics, 1996, ed., 150 pages.

Altschul et al., "Gapped BLAST and PSI-Blast: A new generation of protein database search programs," Nucleic Acids Res., 1997, 25(17):3389-3402.

Anisimova et al., "Approximate likelihood-ratio test for branches: A fast, accurate, and powerful alternative," Systematic Biology, 2006, 55:539-52.

AU Office Action in Australian Appln. No. 2019201986, dated Mar. 13, 2020, 7 pages.

Balazs et al., "Antibody-based protection against HIV infection by vectored immunoprophylaxis," Nature, 2012, 481:81-4.

Balazs et al., "Broad protection against influenza infection by vectored immunoprophylaxis in mice," Nat. Biotechnol., 2013, 31:647-52.

Bartel et al., "Directed evolution of novel adeno-associated viruses for therapeutic gene delivery," Gene Therapy, Mar. 2012, 19: 694-700.

Boutin et al., "Prevalence of serum IgG and neutralizing factors against AAV types 1, 2, 5, 6, 8 and 9 in the healthy population: implications for gene therapy using AAV vectors," Hum. Gene Ther., 2010, 21:704-12.

CA Office Action in Canadian Application No. 2,927,077, dated Jul. 2, 2020, 3 pages.

Calcedo et al. "Worldwide Epidemiology of Neutralizing Antibodies to Adeno-Associated Viruses," J. Infect. Dis., 2009, 199:381-90.

Cao et al., "Phylogenetic relationships among eutherian orders estimated from inferred sequences of mitochondrial proteins: instability of a tree based on a single gene," J. Mol. Evol., 1994, 39:519-27.

Carvalho et al., "Abstract #: 120: Retinal Tropism of In Silico Reconstructed Ancestral Adeno-Associated Viruses, " Molecular Therapy, May 2014, 22(Supplement 1): S45.

Darriba et al., "ProTest3: Fast selection of best-fit models of protein evolution," Bioinformatics, 2011, 27(8):1164-5.

Dayhoff et al., "22: A model of evolutionary change in proteins," Atlas of protein sequence and structure, vol. 5, National Biomedical Research Foundation Silver Spring, 1978, pp. 345-352.

Deal et al., "Vectored antibody gene delivery protects against plasmodium falciparum sporozoite challenge in mice," PNAS USA, 2014, 111:12528-32.

EBI Accession No. GSP:ANJ81137, "Adeno-associated viral capsid protein, AAV -8," Dec. 13, 2007, 2 pages.

Edgar, "MUSCLE: A multipole sequence alignment method with reduced time and space complexity," BMC Bioinform., 2004, 5:113.

EP European Search Report in Application No. 16790158.6, dated Jan. 3, 2019, 5 pages.

EP European Search Report in Application No. 18190809.6, dated Dec. 19, 2018, 5 pages.

EP Extended European Search Report in Application No. 16831443. 3, dated Nov. 26, 2018, 20 pages.

Extended European Search Report in European Appln. No. 22182170. 5, dated Jan. 4, 2023, 11 pages.

Eyewiki.aao.org [online], "Pars Plana Vitrectomy," Nov. 20, 2019, retrieved on Mar. 27, 2020, retrieved from URL<https://eyewiki.aao.org/Pars_Plana_Vitrectomy>, 7 pages.

Felsenstein, "Maximum Likelihood and Minimum-Steps Methods for Estimating Evolutionary Trees from Data on Discrete Characters," Systematic Biology, 1973, 22:240-9.

Fisher et al., "Recombinant adeno-associated virus for muscle directed gene therapy," Nature Med., 1997, 3:306-12.

Gao et al., "Adeno-associated viruses undergo substantial evolution in primates during natural infections," PNAS, 2003, 100:6081-6.

Gao et al., "Clades of Adeno-associated viruses are widely disseminated in human tissues," J. Virol., 2004, 78:6381-88.

(56) References Cited

OTHER PUBLICATIONS

Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
GenBank Accession No. AAC03780.1, "major coat protein VP1 [Adeno-associated virus—2]," Feb. 24, 1998, 1 page.
GenBank Accession No. AAD13756.1, "capsid protein [Adeno-associated virus—5], " Feb. 10, 1999, 1 page.
GenBank Accession No. AAD27757.1, "capsid protein [Adeno-associated virus—1]," Apr. 27, 1999, 1 page.
GenBank Accession No. AAN03857.1, "capsid protein [Adeno-associated virus—8]," Sep. 2, 2002, 1 page.
GenBank Accession No. AAO88201.1, "capsid protein [Non-human primate Adeno-associated virus]," Apr. 9, 2003, 1 page.
GenBank Accession No. AAS99264.1, "capsid protein VP1 [Adeno-associated virus 9]," May 25, 2004, 1 page.
GenBank Accession No. ACB55317, "capsid protein VP1, partial (endogenous virus) [Adeno-associated virus], " dated Jul. 31, 2008, 2 pages.
GenBank Accession No. EU368910.1, "Adeno-associated virus isolate AAV6.2 capsid protein VP1 gene, partial cds," Jul. 31, 2008, 1 page.
GenBank Accession No. EU368925.1, "Adeno-associated virus isolate rh.8R capsid protein VP1 gene, partial cds," dated Jul. 31, 2008, 2 pages.
GenBank Accession No. EU368926, "Adeno-associated virus isolate rh32.33 capsid protein VP1 gene, partial cds," Jul. 31, 2008, 1 page.
Guindon et al., "A simple, fast, and accurate algorithm to estimate large phylogenies by maximum likelihood," Systematic Biology, 2003, 52:696-704.
Henikoff at al., "Amino acid substitution matrices from protein blocks," PNAS, 1992, 89:10915-9.
IN Office Action in Indian Appln. No. 201637014659, dated May 28, 2020, 8 pages.
Jones et al., "The rapid generation of mutation data matrices from protein sequences," Comp. Appl. Biosci., 1992, 8:275-82.
JP Office Action in Japanese Application No. 2018-504699 dated Jun. 9, 2020, 6 pages (with English translation).
Katoh et al., "MAFFT version 5: Improvement in accuracy of multiple sequence alignment," Nuc. Acids Res., 2005, 33:511-8.
Koerber et al., "DNA Shuffling of Adeno-associated Virus Yields Functionally Diverse Viral Progeny," Molecular Therapy, Aug. 2008, 16: 1703-1709.
Lassmann et al., "Kalign, Kalignvu and Mumsa: Web servers for multiple sequence alignment," Nuc. Acids Res., 2006, 34:W596-99.
Limberis et al., "Intranasal antibody gene transfer in mice and ferrets elicits broad protection against pandemic influenza," Sci. Transl. Med., 2013, 5:187ra72.
Lock et al., "Rapid, simple, and versatile manufacturing of recombinant adeno-associated viral vectors at scale," Hum. Gene Ther., 2010, 21:1259-71.
Loytynoja et al., "An Algorithm for progressive multiple alignment of sequences with insertions," PNAS USA, 2005, 102:10557-62.
Loytynoja et al., "Phylogeny-Aware Gap Placement Prevents Errors in Sequence Alignment and Evolutionary Analysis," Science, 2008, 320:1632-5.
Maheshri et al., "Directed evolution of adeno-associated virus yields enhanced gene delivery vectors," Nature Biotechnology, Jan. 2006, 24: 198-204.
Manning et al., "Transient immunosuppression allows transgene expression following readministration of adeno-associated viral vectors," Human Gene Ther., 1998, 9:477-85.
Mao et al., "Persistent Suppression of Ocular Neovascularization with intravitreal administration of AAVrh.10 coding for Bevacizumab," Hum. Gene Ther., 2011, 22:1525-35.

Nakai et al., "A limited No. of transducible hepatocytes restricts a wide-range linear vector dose response in recombinant adeno-associated virus-mediated liver transduction," J. Virol., 2002, 76:11343-9.
Nakai et al., "Unrestricted hepatocyte transduction with adeno-associated virus serotype 8 vectors in mice," J. Virol., 2005, 79:214-24.
Ncbi.nlm.nih.gov [online], "Facts and Figures Concerning the Human Retina," Jul. 5, 2007, retrieved on Mar. 28, 2020, retrieved from URL<https://www.ncbi.nlm.nih.gov/books/NBK11556/>, 6 pages.
Notice of Acceptance in Australian Appln. No. 2021290371, dated Jun. 16, 2023, 4 pages.
Office Action in Australian Appln. No. 2016298394, dated Feb. 25, 2022, 4 pages.
Office Action in Australian Appln. No. 2016298394, dated Mar. 16, 2022, 8 pages.
Office Action in Australian Appln. No. 2021290371, dated Jan. 16, 2023, 6 pages.
Office Action in Chinese Appln. No. 201680057177.2, dated Feb. 25, 2022, 13 pages (with English translation).
Office Action in Chinese Appln. No. 201680057177.2, dated May 31, 2023, 18 pages (with English translation).
Office Action in Chinese Appln. No. 201680057177.2, dated Oct. 9, 2022, 12 pages (with English translation).
Paul et al., "Determination of hepatitis E virus seroprevalence by using recombinant fusion proteins and synthetic peptides," J. Infect. Dis., 1994, 169:801-6.
PCT International Preliminary Report on Patentability in International Application No. PCT/US2016/031218, mailed on Nov. 16, 2017, 7 pages.
PCT International Preliminary Report on Patentability in International Application No. PCT/US2016/044819, mailed on Feb. 8, 2018, 5 pages.
PCT International Search Report and Written Opinion in International Application No. PCT/US2014/060163, mailed on Jul. 13, 2015, 19 pages.
PCT International Search Report and Written Opinion in International Application No. PCT/US2016/031218, mailed on Aug. 8, 2016, 12 pages.
PCT International Search Report and Written Opinion in International Application No. PCT/US2016/044819, mailed on Oct. 31, 2016, 5 pages.
Reeves, "Heterogeneity in the substitution process of amino acid sites of proteins coded for by mitochondrial DNA," J. Mol. Evol., 1992, 35:17-31.
Sakhria et al., "Co-Circulation of Toscana Virus and Punique Virus in Northern Tunisia: A microneutralisation-based seroprevalence study," PLOS Negl. Trop. Dis., 2013, 7:e2429.
Santiago-Ortiz et al., "AAV ancestral reconstruction library enables selection of broadly infectious viral variants," Gene Therapy, Jul. 2015, 22: 934-946, 28 pages.
Sarkar et al., Abstract #: 194: "Seroprevalence Assessment of Novel, Ancestrally Derived AAV Vectors," Molecular Therapy, May 2014, 22(Supplement 1): S74.
Sauerbrei et al. "Seroprevalence of herpes simplex virus type 1 and type 2 in Thuringia, Germany, 1999 to 2006," Euro Survell., 2011, 16(44):3).
Schneider et al., "Empirical codon substitution matrix," BMC Bioinform., 2005, 6:134.
Schon et al., "Retinal gene delivery by adeno-associated virus (AAV) vectors: Strategies and applications," European Journal of Pharmaceutics and Biopharmaceutics, Jan. 2015, 95: 343-352.
Schuster et al., "Biodistribution of adeno-associated virus serotype 9 (AAV9) vector after intrathecal and intravenous delivery in mouse," Frontiers in Neuroanatomy, Jun. 2014, 8: 42 (14 pages).
Schwarz, "Estimating the Dimension of a Model," Ann. Statist. 1978, 6:461-4.
Sen et al., "Improved adeno-associated virus (AAV) serotype 1 and 5 vectors for gene therapy", Scientific Reports, May 2013, 3(1):1-6.
Wang et al., "Systematic Evaluation of AAV Vectors for Liver directed Gene Transfer in Murine Models, " Mol. Ther., 2010, 18:118-25.

(56) References Cited

OTHER PUBLICATIONS

Watanabe et al., "AAVrh10-mediated genetic delivery of bevacizumab to the pleura to provide local anti-VEGF to suppress growth of metastatic lung tumors," Gene Ther., 2010, 17:1042-51.

Whelan et al., "A general empirical model of protein evolution derived from multiple protein families using a maximum-likelihood approach," Mol. Biol. Evol., 2001, 18:691-9.

Xie et al., "AAV-mediated persistent bevacizumab therapy suppresses tumor growth of ovarian cancer," Gynecol. Oncol, 2014, 135: 325-32.

Xu et al., "Seroprevalence of herpes simplex virus types 1 and 2 in pregnant women in the United States," Am. J. Obstet. Gynecol., 2007, 196:43.e1-6.

Yang, "Maximum-likelihood estimation of phylogeny from DNA sequences when substitution rates differ over sites," Mol. Biol. Evol., 1993, 10:1396-1401.

Yang, "PAML: A program package for phylogenetic analysis by maximum likelihood," Comp. Applic. BioSci., 1997, 13:555-6.

Zinn and Vandenberghe, "Adeno-associated virus: fit to serve," Current Opinion in virology, Oct. 2014, 8: 90-97.

Zinn et al., "Abstract #: 237: In Silico, Ancestral Reconstruction of AAV Particles Circumvents Pre-Existing Immunity in Humans," Molecular Therapy, May 2014, 22(Supplement 1): S90.

Zinn et al., "In Silico Reconstruction of the Viral Evolutionary Lineage Yields a Potent Gene Therapy Vector," Cell Rep., Aug. 2015, 12(6):1056-1068.

Notice of Allowance in Japanese Appln. No. 2022-203970, dated Oct. 3, 2023, 6 pages (with English translation).

International Search Report in International Appln. No. PCT/US2006/013375, mailed Dec. 13, 2006, 9 pages.

Office Action in European Appln. No. 20171389.8, dated May 10, 2024, 5 pages.

Office Action in Chinese Appln. No. 202210398488.2, dated Aug. 8, 2024, 11 pages (with English translation).

Office Action in Chinese Appln. No. 202210398489.7, dated Aug. 8, 2024, 11 pages (with English translation).

Office Action in Chinese Appln. No. 202210398490.X, dated Aug. 9, 2024, 12 pages (with English translation).

Office Action in Chinese Appln. No. 202210398491.4, dated Aug. 8, 2024, 11 pages (with English translation).

Office Action in Australian Appln. No. 2023226672, dated Sep. 10, 2024, 4 pages.

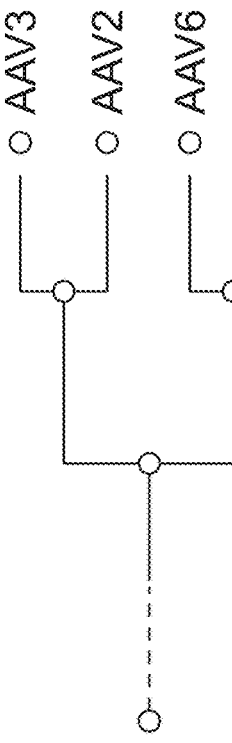
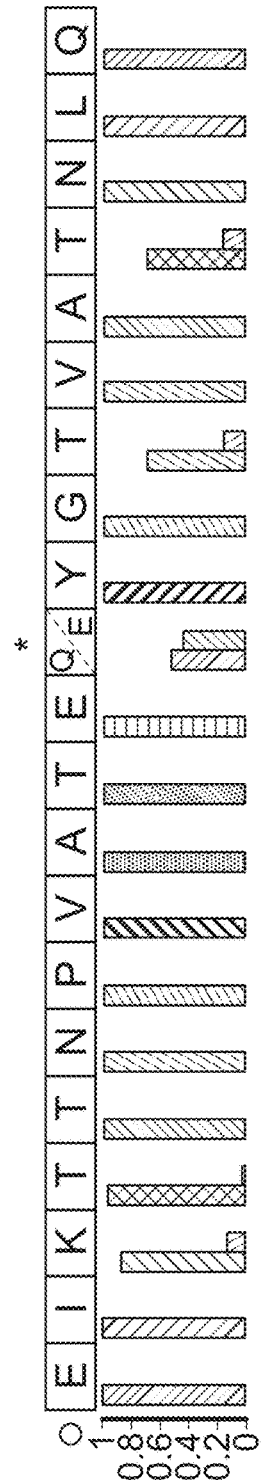
FIG. 2A
FIG. 2B
FIG. 2C
FIG. 2D

```
        10        20        30        40        50        60        70        80        90       100
         |         |         |         |         |         |         |         |         |         |
L0065  MAADGYLPDWLEDNLSEGIREWDDLKPGAPKPKANQKQDDGRGLVLPGYKYLGPFNGLDKGEPVNAADAAALEHDKAYDQQLKAGDNPYLRYNHADAEF
L0027  ..................................................................................................
L0033  ..................................................................................................
L0036  ..................................................................................................
L0044  ..................................................................................................
L0059  ..................................................................................................
L0060  ..................................................................................................
L0062  ..................................................................................................

110       120       130       140       150       160       170       180       190       200
         |         |         |         |         |         |         |         |         |         |
L0065  QERLQEDTSFGGNLGRAVFQAKKRVLEPLGLVEEGAKTAPGKKKRPVEQSPQRPDSSSGIGKKGQQPARKRLNFGQTGDSESVPDPQPLGEPPAAPSGVGS
L0027  ................................................................K.................................
L0033  ................................................................K.................................
L0036  ................................................................K.................................
L0044  ................................................................K.................................
L0059  ..................................................................................................
L0060  ..................................................................................................
L0062  ..................................................................................................

210       220       230       240       250       260       270       280       290       300
         |         |         |         |         |         |         |         |         |         |
L0065  NTMAAGGAPMADNNEGADGVGNASGNWHCDSTWLGDRVITTSTRTWALPTYNNHLYKQISSQSGGSTNDNTYFGYSTPWGYFDFNRFHCHFSPRDWQRL
L0027  ..................................................................................................
L0033  ..................................................................................................
L0036  ..................................................................................................
L0044  ..................................................................................................
L0059  ..................................................................................................
L0060  ..................................................................................................
L0062  ..................................................................................................

310       320       330       340       350       360       370       380       390       400
         |         |         |         |         |         |         |         |         |         |
L0065  INNNWGFRPKKLNFKLFNIQVKEVTTNDGTTTIANNLTSTVQVFTDSEYQLPYVLGSAHQGCLPPFPADVFMIPQYGYLTLNNGSQAVGRSSFYCLEYFP
L0027  ......R...........................................................................................
L0033  ..................................................................................................
L0036  ....S.............................................................................................
L0044  ....S.............................................................................................
L0059  ....S.....R.......................................................................................
L0060  ..........R.......................................................................................
L0062  ....S.............................................................................................
```

| VP1 seq. Δ | AAV5 | AAV2 | AAV8 | rh10 | Anc80L65 | Anc80Lib |
|---|---|---|---|---|---|---|
| AAV5 | ID | 43.0% | 42.6% | 43.0% | 40.5% | 39.9-40.5% |
| AAV2 | 320 | ID | 17.1% | 15.9% | 12.2% | 12.0-12.8% |
| AAV8 | 317 | 127 | ID | 6.5% | 9.1% | 8.7-10.1% |
| rh10 | 320 | 118 | 48 | ID | 8.6% | 7.8-8.9% |
| L0065 | 301 | 91 | 68 | 64 | 0-11 | 0-1.5% |
| Anc80Lib | 297-302 | 89-95 | 65-75 | 58-66 | | ID |

FIG. 8

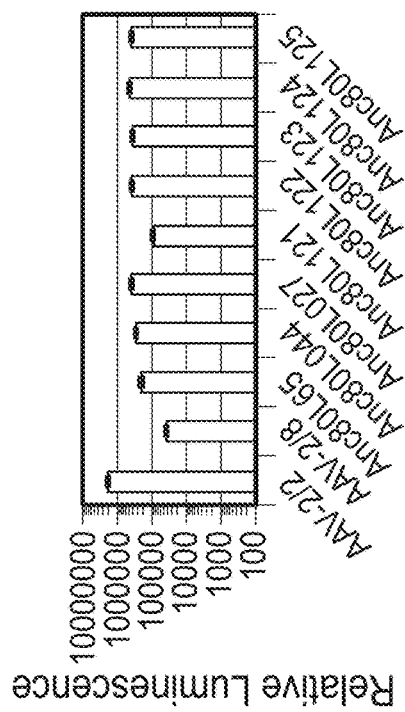
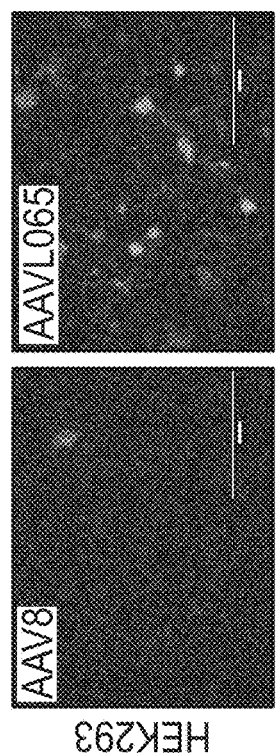
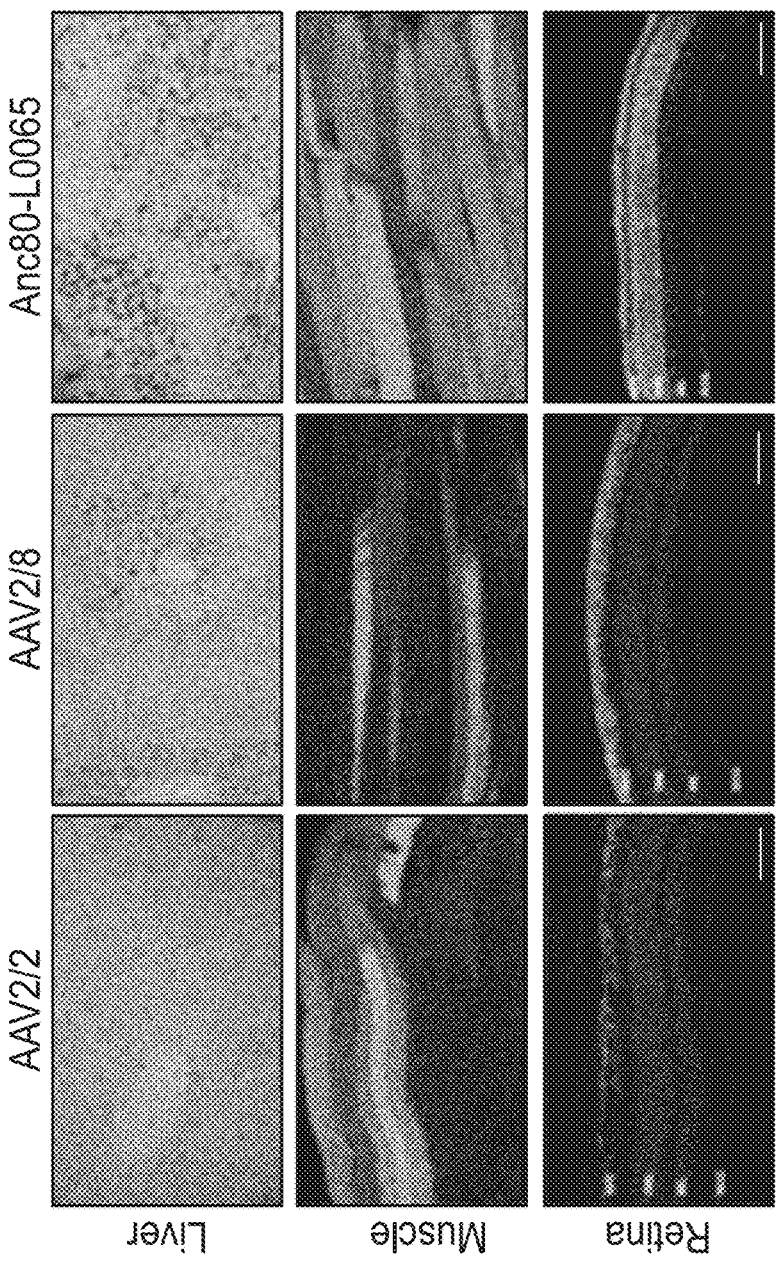

FIG. 11A

| | Anc81 | Anc126 | Anc127 | Anc82 | Anc83 | Anc84 | Anc110 | AAV8 | Anc113 | AAV7 | AAV3 | AAV1 | AAV2 | AAV9 |
|---|---|---|---|---|---|---|---|---|---|---|---|---|---|---|
| L0065 | 97.8% | 97.2% | 95.5% | 95.5% | 94.0% | 92.1% | 94.0% | 90.7% | 93.4% | 90.7% | 90.5% | 89.5% | 87.9% | 86.1% |
| Anc81 | ID | 95.9% | 93.6% | 97.4% | 95.6% | 93.9% | 95.1% | 92.1% | 94.7% | 91.4% | 88.6% | 88.3% | 86.7% | 86.5% |
| Anc126 | | ID | 97.4% | 93.4% | 92.0% | 90.7% | 89.1% | 88.8% | 91.9% | 91.5% | 89.2% | 89.4% | 90.7% | 85.8% |
| Anc127 | | | ID | 91.7% | 90.7% | 89.7% | 92.5% | 88.3% | 91.8% | 88.8% | 91.9% | 91.5% | 90.7% | 86.0% |
| Anc82 | | | | ID | 98.2% | 96.2% | 97.4% | 94.7% | 92.8% | 89.7% | 94.4% | 89.4% | 85.2% | 87.8% |
| Anc83 | | | | | ID | 97.8% | 95.6% | 96.0% | 91.7% | 92.8% | 86.8% | 86.4% | 84.8% | 87.1% |
| Anc84 | | | | | | ID | 93.7% | 94.5% | 91.3% | 89.1% | 86.1% | 85.3% | 84.1% | 86.3% |
| Anc110 | | | | | | | ID | 92.5% | 90.5% | 89.1% | 85.5% | 85.0% | 85.6% | 89.0% |
| AAV8 | | | | | | | | ID | 89.7% | 88.2% | 86.3% | 86.5% | 82.9% | 85.2% |
| Anc113 | | | | | | | | | ID | 87.8% | 85.3% | 84.0% | 82.9% | 83.3% |
| AAV7 | | | | | | | | | | ID | 96.4% | 85.9% | 86.7% | 83.8% | 81.8% |
| AAV3 | | | | | | | | | | | ID | 84.2% | 85.0% | 82.3% | 83.7% |
| AAV1 | | | | | | | | | | | | ID | 86.4% | 87.3% | 82.4% |
| AAV2 | | | | | | | | | | | | | ID | 83.2% | 81.9% |
| AAV9 | | | | | | | | | | | | | | | ID |

FIG. 11B

| | Anc81 | Anc126 | Anc127 | Anc82 | Anc83 | Anc84 | Anc110 | AAV8 | AAV3 | Anc113 | AAV7 | AAV2 | AAV1 | AAV9 |
|---|---|---|---|---|---|---|---|---|---|---|---|---|---|---|
| L0065 | 97.3% | 96.6% | 94.9% | 94.3% | 92.1% | 90.2% | 92.1% | 88.5% | 90.6% | 92.1% | 88.7% | 88.7% | 86.8% | 84.1% |
| Anc81 | ID | 94.7% | 92.7% | 96.6% | 94.3% | 92.7% | 93.6% | 90.4% | 88.4% | 93.4% | 89.7% | 87.4% | 85.2% | 84.4% |
| Anc126 | | ID | 97.5% | 91.5% | 89.7% | 88.7% | 89.9% | 86.7% | 88.4% | 89.7% | 86.5% | 90.8% | 89.5% | 83.3% |
| Anc127 | | | ID | 97.5% | 89.7% | 88.7% | 88.0% | 86.3% | 92.6% | 88.2% | 85.2% | 92.1% | 87.6% | 83.1% |
| Anc82 | | | | ID | 90.2% | 88.7% | 88.5% | 86.3% | 94.9% | 90.6% | 87.1% | 92.1% | 82.8% | 86.3% |
| Anc83 | | | | | ID | 97.7% | 97.0% | 93.8% | 86.1% | 89.3% | 86.3% | 85.6% | 81.4% | 85.6% |
| Anc84 | | | | | | ID | 95.7% | 95.5% | 85.0% | 88.4% | 85.8% | 84.8% | 81.6% | 84.6% |
| Anc110 | | | | | | | ID | 94.7% | 84.8% | 88.0% | 85.6% | 84.4% | 81.6% | 87.8% |
| AAV8 | | | | | | | | ID | 92.8% | 85.0% | 85.6% | 85.7% | 82.4% | 87.8% |
| AAV3 | | | | | | | | | ID | 91.4% | 88.0% | 82.4% | 80.1% | 83.5% |
| Anc113 | | | | | | | | | | ID | 84.5% | 86.7% | 84.5% | 80.9% |
| AAV7 | | | | | | | | | | | ID | 85.4% | 82.8% | 88.9% | 80.5% |
| AAV2 | | | | | | | | | | | | ID | 95.8% | 84.1% | 78.9% |
| AAV1 | | | | | | | | | | | | | ID | 82.4% | 81.4% |
| AAV9 | | | | | | | | | | | | | | ID | 79.6% |

| Viral Production Relative to AAV8 (%) | |
|---|---|
| Anc80-L0065 | 21.75% |
| Anc81 | 54.14% |
| Anc82 | 100.99% |
| Anc83 | 76.86% |
| Anc84 | 91.20% |
| Anc110 | 118.97% |
| Anc113 | 183.10% |
| Anc126 | 2.71% |
| Anc127 | 25.34% |
| AAV2 | 32.56% |
| Neg | 0.27% |

FIG. 13

| Viral Infectivity Relative to AAV8 (%) | |
|---|---|
| Anc80-L0065 | 850.83% |
| Anc81 | 102.26% |
| Anc82 | 28.31% |
| Anc83 | 47.36% |
| Anc84 | 68.78% |
| Anc110 | 24.56% |
| Anc113 | 117.12% |
| Anc127 | 113.78% |
| AAV2 | 5225.61% |
| Neg | 0.35% |

FIG. 16

| | AAV8 | AAV2 | Anc80-L0065 | Anc81 | Anc82 | Anc83 | Anc84 | Anc110 | Anc113 | Anc126 | Anc127 |
|---|---|---|---|---|---|---|---|---|---|---|---|
| Infectivity | = | +++ | +++ | = | - | - | - | - | = | ND | = |
| Production | = | - | -- | - | = | = | = | = | ++ | -- | - |

Key
+++ : > 225%
++ : 175% - 224.5%
+ : 125 - 174.9%
= : 75% - 124.9%
- : 25-74.9%
-- : 0-24.9%
ND : Not Determined

FIG. 17

METHODS OF PREDICTING ANCESTRAL VIRUS SEQUENCES AND USES THEREOF

CROSS REFERENCE TO RELATED APPLICATIONS

This application is a Divisional application of, and claims the benefit under 35 U.S.C. § 121 to, U.S. application Ser. No. 17/408,104, filed Aug. 20, 2021, which is a Divisional application of, and claims the benefit under 35 U.S.C. § 121 to, U.S. application Ser. No. 16/906,849, filed Jun. 19, 2020, now U.S. Pat. No. 11,466,258, which is a Continuation application of, and claims the benefit under 35 U.S.C. § 121 to, U.S. application Ser. No. 16/717,942, filed Dec. 17, 2019, now U.S. Pat. No. 11,104,885, which is a Divisional application of, and claims the benefit under 35 U.S.C. § 121 to, U.S. application Ser. No. 16/179,524, filed Nov. 2, 2018, now U.S. Pat. No. 10,526,584, which is a Divisional application of, and claims the benefit under 35 U.S.C. § 121 to, U.S. application Ser. No. 15/633,292, filed Jun. 26, 2017, now U.S. Pat. No. 10,119,125, which is a Divisional application of, and claims the benefit under 35 U.S.C. § 121 to, U.S. application Ser. No. 15/291,470, filed Oct. 12, 2016, now U.S. Pat. No. 9,719,070, which is a Divisional application of, and claims the benefit under 35 U.S.C. § 121 to, U.S. application Ser. No. 15/095,856, filed Apr. 11, 2016, now U.S. Pat. No. 9,695,220, which is a Continuation-In-Part of International Application No. PCT/US2014/060163 filed Oct. 10, 2014, which claims the benefit of priority under 35 U.S.C. § 119(e) to U.S. Application No. 61/889,827, filed Oct. 11, 2013, the contents of all of which are incorporated herein by reference in their entireties.

SEQUENCE LISTING

This application contains a Sequence Listing that has been submitted electronically as an XML file named "49998-0155008_SL_ST26.XML." The XML file, created on Apr. 20, 2023, is 143,599 bytes in size. The material in the XML file is hereby incorporated by reference in its entirety.

TECHNICAL FIELD

This disclosure generally relates to viruses.

BACKGROUND

Circumventing and avoiding a neutralizing or toxic immune response against a gene therapy vector is a major challenge with all gene transfer vector types. Gene transfer to date is most efficiently achieved using vectors based on viruses circulating in humans and animals, e.g., adenovirus and adeno-associated virus (AAV). However, if subjects have been naturally infected with a virus, a subsequent treatment with a vector based on that virus leads to increased safety risks and decreased efficiency of gene transfer due to cellular and humoral immune responses. Capsid antigens are primarily responsible for the innate and/or adaptive immunity toward virus particles, however, viral gene-encoded polypeptides also can be immunogenic.

SUMMARY

This disclosure describes methods of predicting and synthesizing ancestral viral sequences or portions thereof, and also describes virus particles containing such ancestral viral sequences. The methods described herein were applied to adeno-associated virus (AAV); thus, this disclosure describes predicted ancestral AAV sequences and AAV virus particles containing such ancestral AAV sequences. This disclosure also describes the reduced seroprevalance exhibited by virus particles containing ancestral sequences relative to virus particles containing contemporary sequences.

In one aspect, this disclosure includes adeno-associated virus (AAV) capsid polypeptides, e.g., synthetic and/or artificial AAV capsid polypeptides, having an amino acid sequence selected from the group consisting of SEQ ID NOs: 1, 3, 5, 7, 9, 11, 13, 15 and 17. In some implementations, the AAV capsid polypeptides or virus particles comprising the AAV capsid polypeptides exhibit a lower seroprevalence than do an AAV2 capsid polypeptide or a virus particle comprising an AAV2 capsid polypeptide, and the AAV capsid polypeptides or virus particles comprising the AAV capsid polypeptides exhibit about the same or a lower seroprevalence than do an AAV8 capsid polypeptide or a virus particle comprising an AAV8 capsid polypeptide. In some embodiments, the AAV capsid polypeptides or virus particles comprising the AAV capsid polypeptides are neutralized to a lesser extent by human serum than is an AAV2 capsid polypeptide or a virus particle comprising an AAV2 capsid polypeptide, and the AAV capsid polypeptides or virus particles comprising the AAV capsid polypeptides are neutralized to a similar or lesser extent by human serum as is an AAV8 capsid polypeptide or a virus particle comprising an AAV8 capsid polypeptide. In some embodiments, the AAV capsid polypeptides are purified. The AAV capsid polypeptides provided herein can be encoded by a nucleic acid sequence selected from the group consisting of SEQ ID NOs: 2, 4, 6, 8, 10, 12, 14, 16, and 18.

In one aspect, the disclosure provides nucleic acid molecules, e.g., synthetic and/or artificial nucleic acid molecules, encoding an adeno-associated virus (AAV) capsid polypeptide having a nucleic acid sequence selected from the group consisting of SEQ ID NOs: 2, 4, 6, 8, 10, 12, 14, 16, and 18. Also provided are vectors that includes such a nucleic acid, and a host cell that includes such a vector.

In another aspect, the disclosure provides purified virus particles that include an AAV capsid polypeptide described herein. In some embodiments, the virus particles include a transgene.

In other aspects, the disclosure provides adeno-associated virus (AAV) capsid polypeptides, e.g., synthetic and/or artificial AAV capsid polypeptides, having at least 95% (e.g., 97, 98, 99, or 100%) sequence identity to an amino acid sequence selected from the group consisting of SEQ ID NOs: 19, 20, 21, 22, 23, 24, 25 and 26. In some embodiments, the AAV capsid polypeptides or virus particles comprising the AAV capsid polypeptide exhibit a lower seroprevalence than does an AAV2 capsid polypeptide or a virus particle comprising an AAV2 capsid polypeptide, and the AAV capsid polypeptide or a virus particle comprising the AAV capsid polypeptide exhibit about the same or a lower seroprevalence than does an AAV8 capsid polypeptide or a virus particle comprising an AAV8 capsid polypeptide. In some embodiments, the AAV capsid polypeptides or virus particles comprising the AAV capsid polypeptide are neutralized to a lesser extent by human serum than is an AAV2 capsid polypeptide or a virus particle comprising an AAV2 capsid polypeptide, and the AAV capsid polypeptide or a virus particle comprising the AAV capsid polypeptide is neutralized to a similar or lesser extent by human serum as is an AAV8 capsid polypeptide or a virus particle comprising an AAV8 capsid polypeptide. In some embodiments, the AAV capsid polypeptides are purified.

In another aspect, the AAV capsid polypeptides described herein can be encoded by nucleic acid sequences as described herein. In one implementation, the disclosure provides nucleic acid molecules encoding an adeno-associated virus (AAV) capsid polypeptide, wherein the nucleic acid molecules have at least 95% (e.g., 97, 98, 99, or 100%) sequence identity to a nucleic acid sequence as shown herein. The disclosure also provides vectors including such nucleic acid molecules, as are host cells that include such a vector.

In one aspect, the disclosure provides virus particles that include at least one of the AAV capsid polypeptides described herein. In some embodiments, the virus particles include a transgene.

In certain aspects, the disclosure provides methods of administering a virus particle as described herein to a subject in need of gene transfer or vaccination. In some embodiments, the virus particles exhibit less seroprevalence than does an AAV2 virus particle. In some embodiments, the virus particles exhibit about the same or less seroprevalence than does an AAV8 virus particle. In some embodiments, the virus particles are neutralized to a lesser extent by human serum than is an AAV2 virus particle, and the AAV virus particles are neutralized to a similar or lesser extent by human serum than is an AAV8 virus particle.

In one aspect, the disclosure provides methods of administering a target antigen operably linked to an AAV capsid polypeptide as described herein to a subject in need of vaccination. In some embodiments, the AAV capsid polypeptides exhibit less seroprevalence than does an AAV2 capsid polypeptide. In some embodiments, the AAV capsid polypeptide exhibits about the same or less seroprevalence than does an AAV8 capsid polypeptide. In some embodiments, the AAV capsid polypeptides are neutralized to a lesser extent by human serum than is an AAV2 capsid polypeptide, and the AAV capsid polypeptide is neutralized to a similar or lesser extent by human serum than is an AAV8 capsid polypeptide.

In another aspect, the disclosure provides in silico methods of predicting a sequence of an ancestral virus or portion thereof. Such methods typically include providing nucleotide or amino acid sequences from a plurality of contemporary viruses or portions thereof; aligning the sequences using a multiple sequence alignment (MSA) algorithm; modeling evolution to obtain a predicted ancestral phylogeny of the plurality of contemporary viruses or portions thereof estimating, at a phylogenic node of the predicted ancestral phylogeny, the evolutionary probability of a particular nucleotide or amino acid residue at each position of the sequence; and predicting, based on the estimated probability at each position, a sequence of an ancestral virus or portion thereof.

In some embodiments, one or more, or all, of the steps are performed using a computer processor. In some embodiments, the MSA algorithm uses phylogenetic information to predict if a gap in the alignment is a result of a deletion or an insertion. In some embodiments, the MSA algorithm is a Probabilistic Alignment Kit (PRANK). In some embodiments, the model used for modeling evolution is selected using Aikake Information Criterion (AIC). In some embodiments, the predicted ancestral phylogeny is obtained using a JTT model with a Gamma distribution model ("+G") and a frequency calculation of πi ("+F"). In some embodiments, the modeling the evolution step is performed using a JTT+G+F model. In some embodiments, the methods include synthesizing, based on the predicted sequence, the ancestral virus or portion thereof. In some embodiments, the methods include assembling the ancestral virus or portion thereof into an ancestral virus particle.

In some embodiments, the methods also include screening the ancestral virus particle for at least one of the following: (a) replication; (b) gene transfer properties; (c) receptor binding; or (d) seroprevalence. In some embodiments, the ancestral virus particles exhibit less seroprevalence than does a virus particle assembled from at least one of the plurality of contemporary viruses or portions thereof. In some embodiments, the ancestral virus particle is neutralized to a lesser extent by human serum than is a virus particle assembled from at least one of the plurality of contemporary viruses or portions thereof. In some embodiments, the plurality of contemporary viruses or portions thereof belong to a family selected from the group consisting of adenovirus (AV), human immunodeficiency virus (HIV), retrovirus, lentivirus, herpes simplex virus (HSV), vaccinia virus, pox virus, influenza virus, respiratory syncytial virus, parainfluenza virus, and foamy virus.

Thus, the present disclosure provides ancestral viruses or portions thereof that exhibit reduced susceptibility to pre-existing immunity in current day human populations than do contemporary viruses or portions thereof. Generally, the reduced susceptibility to pre-existing immunity exhibited by the ancestral viruses or portions thereof in current day human populations is reflected as a reduced susceptibility to neutralizing antibodies.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

The patent or application file contains at least one drawing executed in color. Copies of this patent or patent application publication with color drawings will be provided by the Office upon request and payment of the necessary fee.

FIG. 1 is a schematic showing the relationships between ancestral/contemporary viral infections and ancestral/contemporary host immune response.

FIGS. 2A to 2D are a series of schematics showing an example of an ancestral reconstruction procedure. Data shown are excerpted from a full dataset and represent residues 564-584 (AAV2-VP1 numbering; SEQ ID NOs: 37-43 (top to bottom)).

FIG. 3 illustrates a phylogenetic tree of AAV contemporary sequences generated using the methods described herein.

FIG. 4 illustrates an alignment of ancestral AAV VP1 polypeptides (SEQ ID NOs: 23, 19, 24, 25, 26, 20, 21 and 22, top to bottom).

FIGS. 5A and 5B together illustrate an alignment of functional ancestral AAV VP1 polypeptides and contemporary AAV VP1 polypeptides (SEQ ID NOs: 23, 19, 24, 25 21, 22, 26, 20, 27, 28, 29, 30, 31, 32, 33 and 34, top to bottom).

FIG. 6 is an electrophoretic gel demonstrating that ancestral AAV VP1 sequences are transcribed and alternately spliced in a manner similar to that for contemporary AAV VP1 sequences.

FIG. 8 is a graph showing the sequence comparison (% up from diagonal, #of aa differences below) between the Anc80 library and Anc80L65.

FIGS. 9A-D are images of experimental results demonstrating that Anc80L65 is capable of assembling and yielding particles of high titer. Panel A shows that Anc80L65 is able to produce vector yields equivalent to AAV2; Panel B is a TEM image of virus particles that include Anc80L65; Panel C shows that virus particles that include Anc80L65 are able to produce AAV cap VP1, 2 and 3 proteins based on SDS-PAGE gel under denaturing conditions; and Panel D shows a Western blot of Anc80L65 using the AAV capsid antibody, B1.

FIGS. 10A-C are images of experimental results demonstrating that Anc80L65 is able to infect cells in vitro on HEK293 cells using GFP as readout (Panel A) or luciferase (Panel B) versus AAV2 and/or AAV8 controls and also is efficient at targeting liver following an IV injection of AAV encoding a nuclear LacZ transgene (top row, Panel C: liver), following direct IM injection of an AAV encoding GFP (middle row, Panel C: muscle), and following sub-retinal injection with AAV encoding GFP (bottom row, Panel C: retina).

FIGS. 11A and 11B are sequence identity matrices producing using MAFFT that show the amino acid sequences of the VP1 proteins of ancestral vectors aligned with those of representative extant AAVs (FIG. 11A), and the amino acid sequences of the VP3 proteins of ancestral vectors aligned with those of representative extant AAVs (FIG. 11B).

Figure 12:
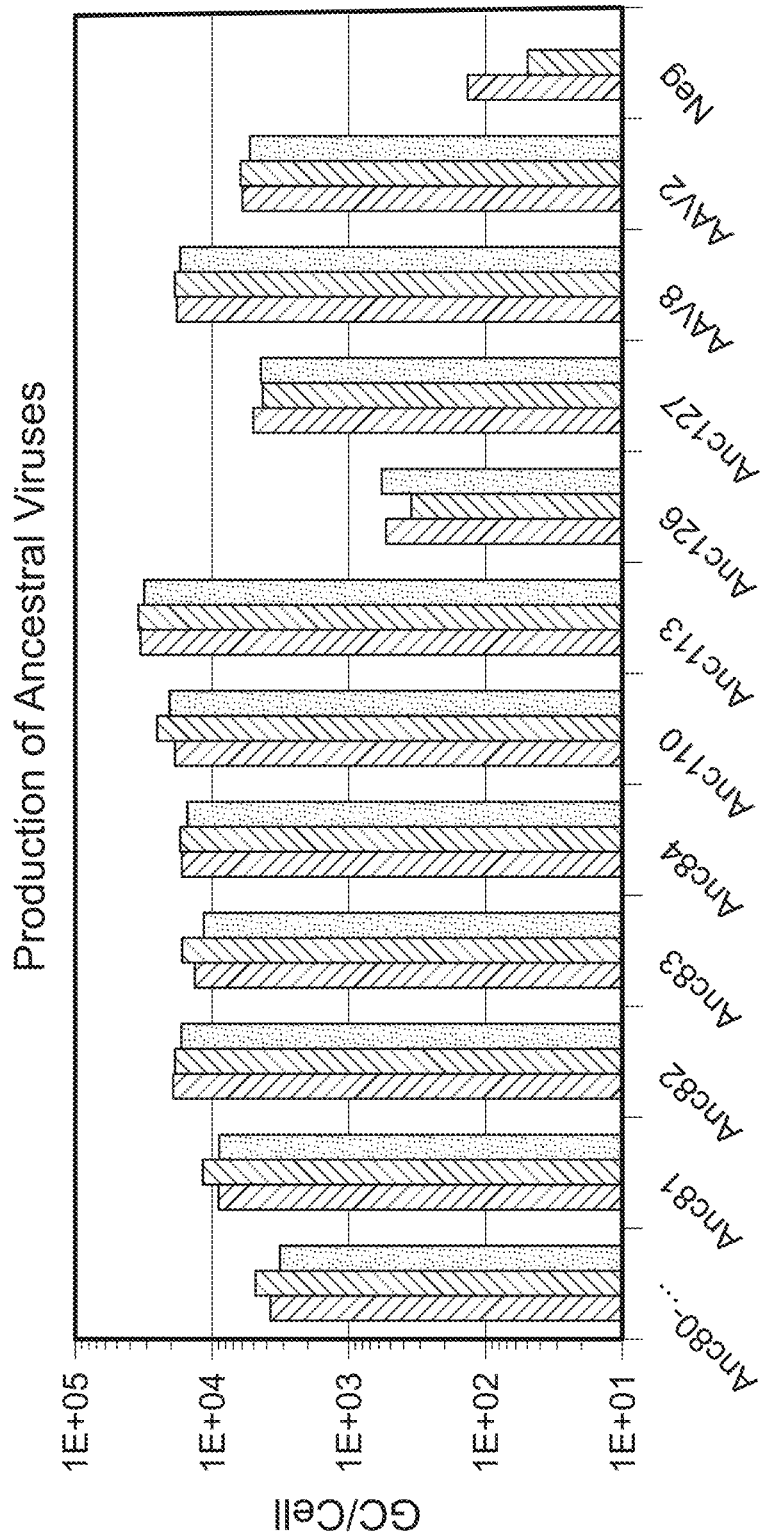

FIG. 12 is a graph that demonstrates that AAV vectors were produced in triplicate in small scale (6-well dishes). Crude viruses were assessed via qPCR to determine the absolute production of each vector.

FIG. 13 is a table showing the titers of each vector, averaged and compared, to those of AAV8.

Figure 14:
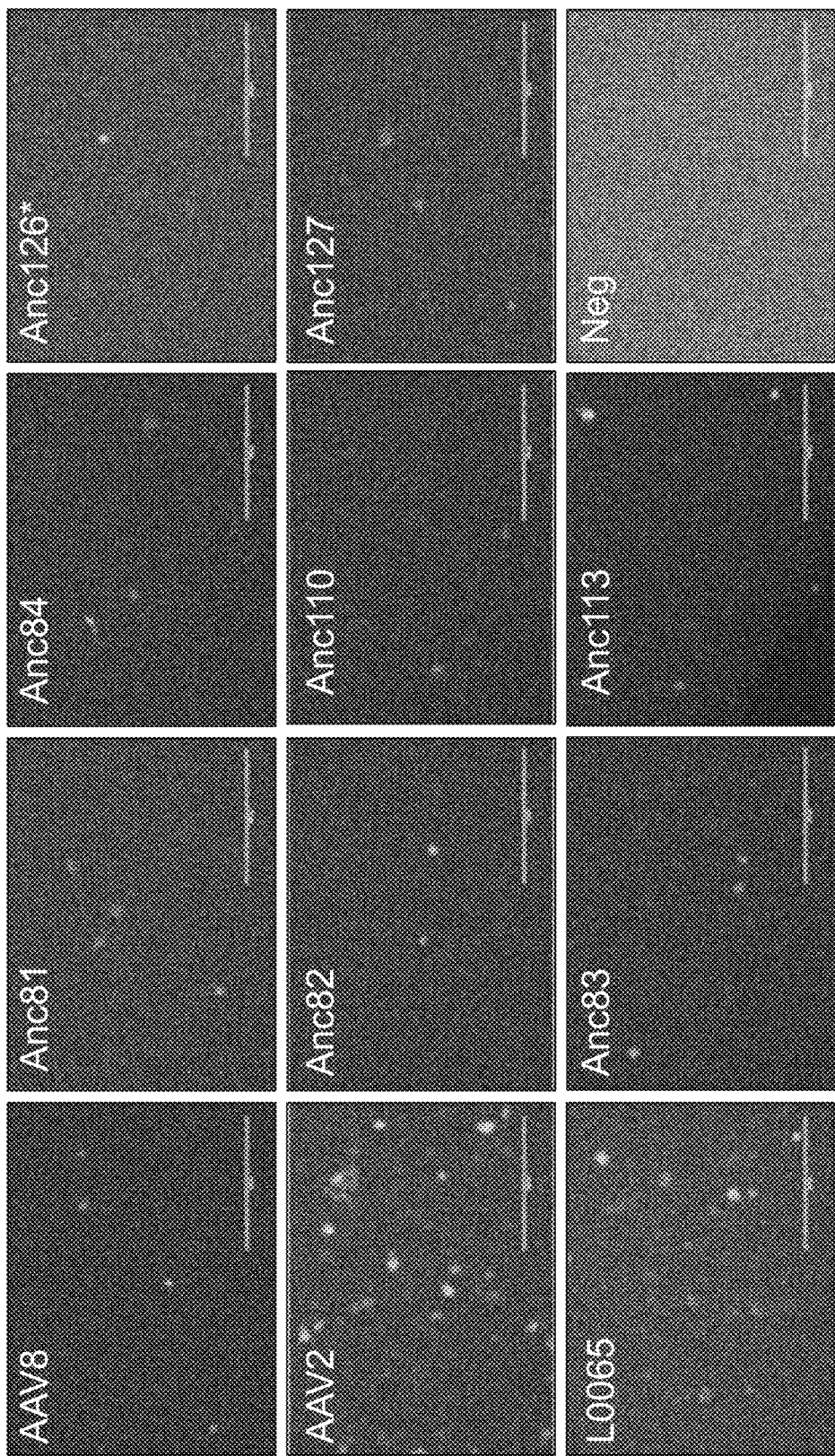

FIG. 14 are photographs that show the results of experiments in which 1.9E3 GC/cell of each vector was added to HEK293 cells (except for Anc126, in which case MOIs of 2.5E2-3.1E2 GC/cell were achieved). Sixty hours later, infectivity was assessed using fluorescence microscopy.

Figure 15:
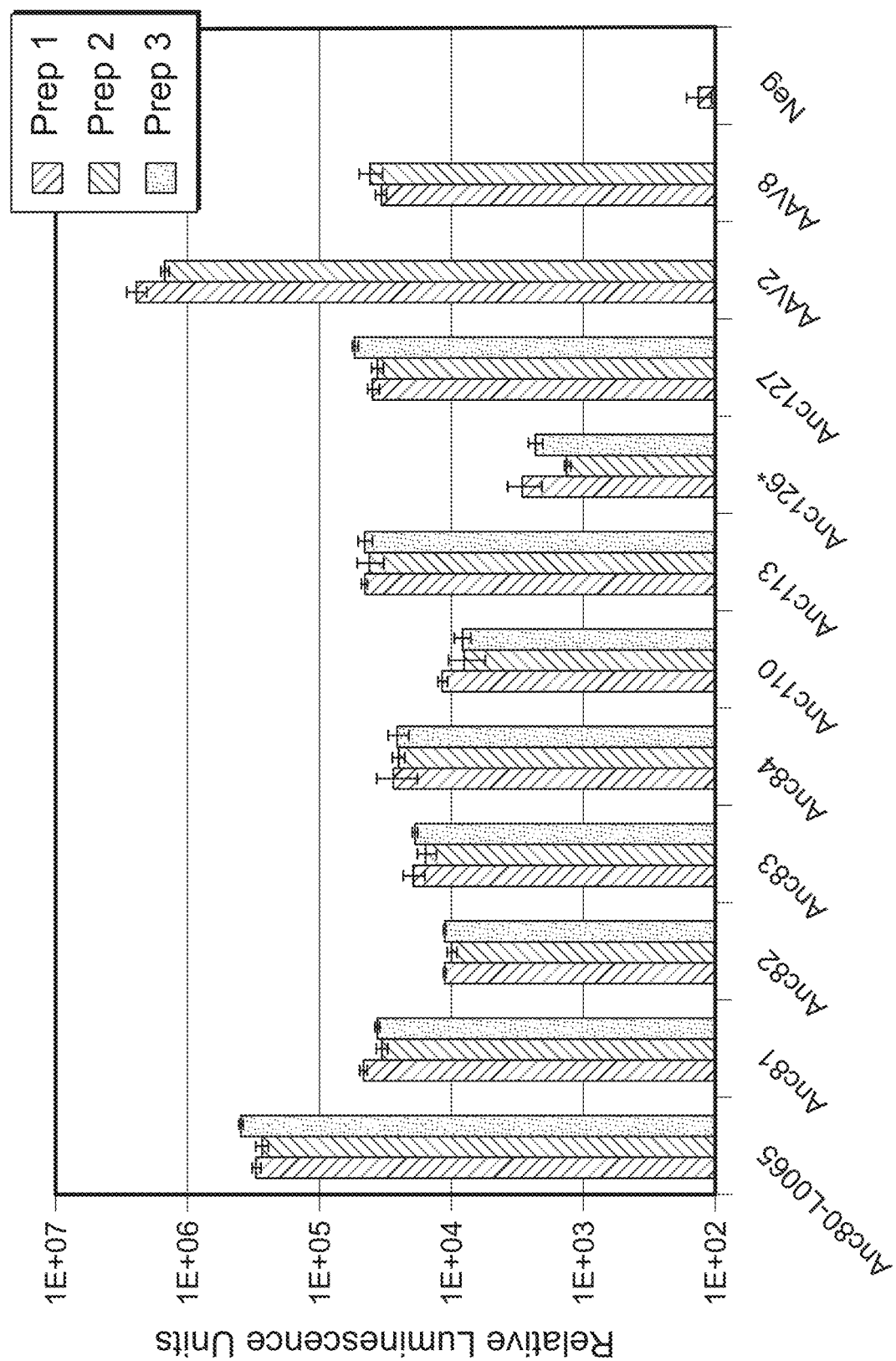

FIG. 15 is a graph showing the results of experiments in which the same cells from FIG. 16 were lysed and assayed for luciferase expression. As in FIG. 14, Anc126 was not titer controlled with the other vectors, but rather ranged from an MOI of 2.5E2-3.1E2 GC/cell.

FIG. 16 is a table showing the luminescence of cells transduced by each vector, which were averaged and compared to those of AAV8.

FIG. 17 is a chart that provides a summary of in vitro experiments to determine the relative production and infectivity of the ancestral AAV vectors described herein.

DETAILED DESCRIPTION

Gene transfer, either for experimental or therapeutic purposes, relies upon a vector or vector system to shuttle genetic information into target cells. The vector or vector system is considered the major determinant of efficiency, specificity, host response, pharmacology, and longevity of the gene transfer reaction. Currently, the most efficient and effective way to accomplish gene transfer is through the use of vectors or vector systems based on viruses that have been made replication-defective.

Seroprevalence studies, however, indicate that significant proportions of worldwide human populations have been pre-exposed (e.g., by natural infection) to a large number of the viruses currently used in gene transfer and, therefore, harbor pre-existing immunity. Neutralizing antibodies toward the viral vector in these pre-exposed individuals are known to limit, sometimes significantly, the extent of gene transfer or even re-direct the virus away from the target. See, for example, Calcedo et al. (2009, J. Infect. Dis., 199:381-90) and Boutin et al. (2010, Human Gene Ther., 21:704-12). Thus, the present disclosure is based on the recognition that ancestral viruses or portions thereof exhibit reduced susceptibility to pre-existing immunity (e.g., reduced susceptibility to neutralizing antibodies) in current day human populations than do contemporary viruses or portions thereof.

Figure 1:
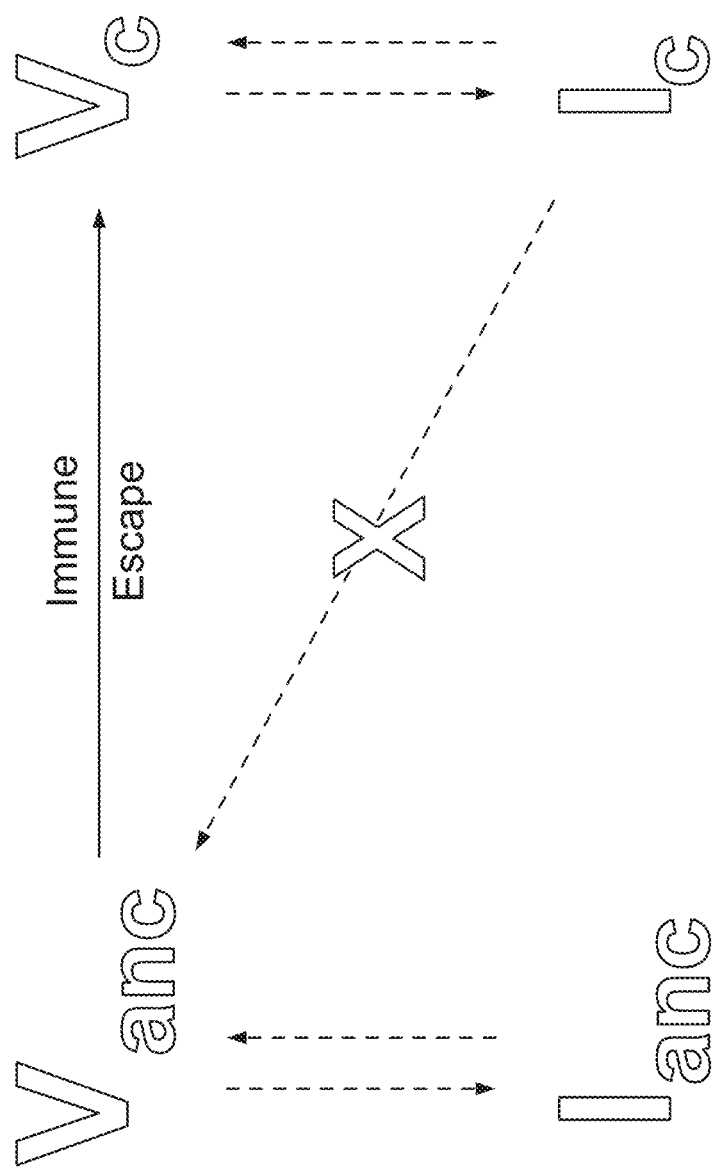

FIG. 1 is a schematic showing the relationships between ancestral and contemporary viral infections and ancestral and contemporary host immune response. FIG. 1 shows how ancestral AAVs can be refractory to contemporary pre-existing immunity. A contemporary, extant virus (Vc) is presumed to have evolved from an ancestral species (Vanc), primarily under evolutionary pressures of host immunity through mechanisms of immune escape. Each of these species, Vanc and Vc, have the ability to induce adaptive immunity including B and T cell immunity (Ianc and Ic, respectively). It was hypothesized, and confirmed herein, that immunity induced by contemporary viruses does not necessarily cross-react with an ancestral viral species, which can be substantially different in terms of epitope composition than the extant virus.

This disclosure provides methods of predicting the sequence of an ancestral virus or a portion thereof. One or more of the ancestral virus sequences predicted using the methods described herein can be generated and assembled into a virus particle. As demonstrated herein, virus particles assembled from predicted ancestral viral sequences can exhibit less, sometimes significantly less, seroprevalence than current-day, contemporary virus particles. Thus, the ancestral virus sequences disclosed herein are suitable for use in vectors or vector systems for gene transfer.

Methods of Predicting and Synthesizing an Ancestral Viral Sequence

To predict an ancestral viral sequence, nucleotide or amino acid sequences first are compiled from a plurality of contemporary viruses or portions thereof. While the methods described herein were exemplified using adeno-associated virus (AAV) capsid sequences, the same methods can be applied to other sequences from AAV (e.g., the entire genome, rep sequences, ITR sequences) or to any other virus or portion thereof. Viruses other than AAV include, without limitation, adenovirus (AV), human immunodeficiency virus (HIV), retrovirus, lentivirus, herpes simplex virus (HSV), measles, vaccinia virus, pox virus, influenza virus, respiratory syncytial virus, parainfluenza virus, foamy virus, or any other virus to which pre-existing immunity is considered a problem.

Sequences from as few as two contemporary viruses or portions thereof can be used, however, it is understood that a larger number of sequences of contemporary viruses or portions thereof is desirable so as to include as much of the landscape of modern day sequence diversity as possible, but also because a larger number of sequences can increase the predictive capabilities of the algorithms described and used. For example, sequences from 10 or more contemporary viruses or portions thereof can be used, sequences from 50 or more contemporary viruses or portions thereof can be used, or sequences from 100 or more contemporary viruses or portions thereof can be used.

Such sequences can be obtained, for example, from any number of public databases including, without limitation, GenBank, UniProt, EMBL, International Nucleotide Sequence Database Collaboration (INSDC), or European Nucleotide Archive. Additionally or alternatively, such sequences can be obtained from a database that is specific to a particular organism (e.g., HIV database). The contemporary sequences can correspond to the entire genome, or only a portion of the genome can be used such as, without limitation, sequences that encode one or more components of the viral capsid, the replication protein, or the ITR sequences.

Next, the contemporary sequences are aligned using a multiple sequence alignment (MSA) algorithm. FIG. 2A is a schematic showing an alignment of multiple sequences. MSA algorithms are well known in the art and generally are designed to be applied to different size datasets and different inputs (e.g., nucleic acid or protein), and to align the sequences in a particular manner (e.g., dynamic programming, progressive, heuristic) and apply different scoring schemes in the alignment (e.g., matrix-based or consistency-based, e.g., minimum entropy, sum of pairs, similarity matrix, gap scores). Well known MSA algorithms include, for example, ClustalW (Thompson et al., 1994, Nuc. Acids Res., 22:4673-90), Kalign (Lassmann et al., 2006, Nuc. Acids Res., 34:W596-99), MAFFT (Katoh et al., 2005, Nuc. Acids Res., 33:511-8), MUSCLE (Edgar, 2004, BMC Bioinform., 5:113), and T-Coffee (Notredame et al., 2000, J. Mol. Biol., 302:205-17).

As described herein, one of the main features when selecting a MSA algorithm for use in the methods described herein is the manner in which the algorithm treats a gap in the alignment. Gaps in a sequence alignment can be assigned a penalty value that is either dependent or independent on the size of the gap. In the present methods, it is preferred that the MSA algorithm used in the methods described herein apply phylogenetic information to predict whether a gap in the alignment is a result of a deletion or an insertion as opposed to a biased, non-phylogenetic treatment of gaps due to, e.g., insertions and/or deletions. A suitable method of treating gaps in alignments and evolutionary analysis is described in Loytynoja and Goldman, 2008, Science, 320:1632-5, and commercially available algorithms that apply gaps in alignments in a manner that is suitable for use in the methods described herein is a Probabilistic Alignment Kit (PRANK; Goldman Group Software; Loytynoja and Goldman, 2005, PNAS USA, 102:10557-62), and variations of the PRANK algorithm.

An evolutionary model is then applied to the resulting alignment to obtain a predicted ancestral phylogeny (see FIG. 2B). There are a number of evolutionary models available in the art, each of which apply slightly different matrices of replacement rates for amino acids. Without limitation, algorithms for applying models of evolution include the Dayhoff models (e.g., PAM120, PAM160, PAM250; Dayhoff et al., 1978, In *Atlas of Protein Sequence and Structure* (ed. Dayhoff), pp. 345-52, National Biomedical Research Foundation, Washington D.C.), the JTT model (Jones et al., 1992, Comp. Appl. Biosci., 8:275-82), the WAG model (Whelan and Goldman, 2001, Mol. Biol. Evol., 18:691-9), and the Blosum models (e.g., Blosum45, Blosum62, Blosum80; Henikoff and Henikoff, 1992, PNAS USA, 89:10915-9). In addition, the constraints that structure and function impose on an evolutionary model can themselves be modeled, for example, by considering that some positions are invariant ("+I"; Reeves, 1992, J. Mol. Evol., 35:17-31), that some positions undergo different rates of change ("+G"; Yang, 1993, Mol. Biol. Evol., 10:1396-1401), and/or that equilibrium frequencies of nucleotides or amino acids are the same as those in the alignment ("+F"; Cao et al., 1994, J. Mol. Evol., 39:519-27).

The fitness of one or more models of evolution can be evaluated using the Aikake Information Criterion (AIC; Akaike, 1973, In *Second International Symposium on Information Theory*, Petrov and Csaki, eds., pp 267-81, Budapest, Akademiai Kiado), the Bayesian Information Criterion (BIC; Schwarz, 1978, Ann. Statist. 6:461-4), or variations or combinations thereof. In addition, AIC, BIC, or variations or combinations thereof can be used to evaluate the relative importance of including one or more parameters (e.g., the constraints discussed above) in the evolutionary model.

As explained in the Example section below, ProTest3 (Darriba et al., 2011, Bioinformatics, 27(8):1164-5) can be used to determine, based on the lowest AIC, that a JTT+G+F algorithm was the most suitable model for AAV evolution. It would be understood by a skilled artisan that a JTT+G+F algorithm also may be used to predict ancestral viral sequences other than AAV capsid polypeptides, however, it also would be understood by a skilled artisan that, depending on the dataset and the fitness score, a different model of evolution may be more suitable.

Once a model of evolution has been selected and its fitness determined, a phylogenetic tree of the virus sequences or portions thereof can be constructed. Constructing phylogenetic trees is known in the art and typically employs maximum likelihood methods such as those implemented by PhyML (Guindon and Gascuel, 2003, Systematic Biology, 52:696-704)), MOLPHY (Adachi and Hasegawa, 1996, ed. Tokyo Institute of Statistical Mathematics), BioNJ (Gascuel, 1997, Mol. Biol. Evol., 14:685-95), or PHYLIP (Felsenstein, 1973, Systematic Biology, 22:240-9). A skilled artisan would understand that a balance between computational complexity and the goodness of fit is desirable in a model of amino acid substitutions.

If desired, the phylogenetic tree can be assessed for significance. A number of statistical methods are available and routinely used to evaluate the significance of a model including, without limitation, bootstrap, jackknife, cross-validation, permutation tests, or combinations or variations thereof. Significance also can be evaluated using, for example, an approximate likelihood-ratio test (aLRT; Anisimova and Gascuel, 2006, Systematic Biology, 55:539-52)).

At any phylogenetic node of the phylogeny (e.g., an interior phylogenetic node), the sequence can be reconstructed by estimating the evolutionary probability of a particular nucleotide or amino acid residue at each position of the sequence (FIG. 2C). A phylogenic node refers to an intermediate evolutionary branch point within the predicted ancestral phylogeny. As used herein, "evolutionary probability" refers to the probability of the presence of a particular nucleotide or amino acid at a particular position based on an evolutionary model as opposed to a model that does not take into account, for example, an evolutionary shift in the codon usage. Exemplary models that take into account the evolutionary probability of a particular nucleotide or amino acid residue at a particular position can be estimated using, for example, any number of maximum likelihood methods including, without limitation, Phylogenetic Analysis by Maximum Likelihood (PAML; Yang, 1997, Comp. Applic. BioSci., 13:555-6) or Phylogenetic Analysis Using Parsimony (PAUP; Sinauer Assoc., Inc., Sunderland, MA).

Based on the estimated evolutionary probability of a particular nucleotide or amino acid residue at each position, the predicted sequence of an ancestral virus or portion thereof can be assembled to form a complete or partial synthetic nucleic acid or polypeptide sequence. If desired, the likelihood that any residue was in a given state at a given node along the node can be calculated, and any position along the sequence having a calculated posterior probability beneath a particular threshold can be identified (FIG. 2D). In this manner, an ancestral scaffold sequence can be generated, which can include variations at those positions having a probability below the particular threshold.

If the ancestral sequence that is predicted using the methods herein is a nucleic acid sequence, the sequence then can be codon optimized so that it can be efficiently translated into an amino acid sequence. Codon usage tables for different organisms are known in the art. Optionally, however, a codon usage table can be designed based on one or more contemporary sequences that has homology (e.g., at least 90% sequence identity) to the ancestral scaffold sequence, and an ancestral sequence as described herein can be codon optimized toward mammalian (e.g., human) codon usage.

Any or all of the steps outlined herein for predicting an ancestral viral sequence can be performed or simulated on a computer (e.g., in silico) using a processor or a microprocessor.

Ancestral Adeno Associated Virus (AAV) Scaffold Sequences

Figure 3:
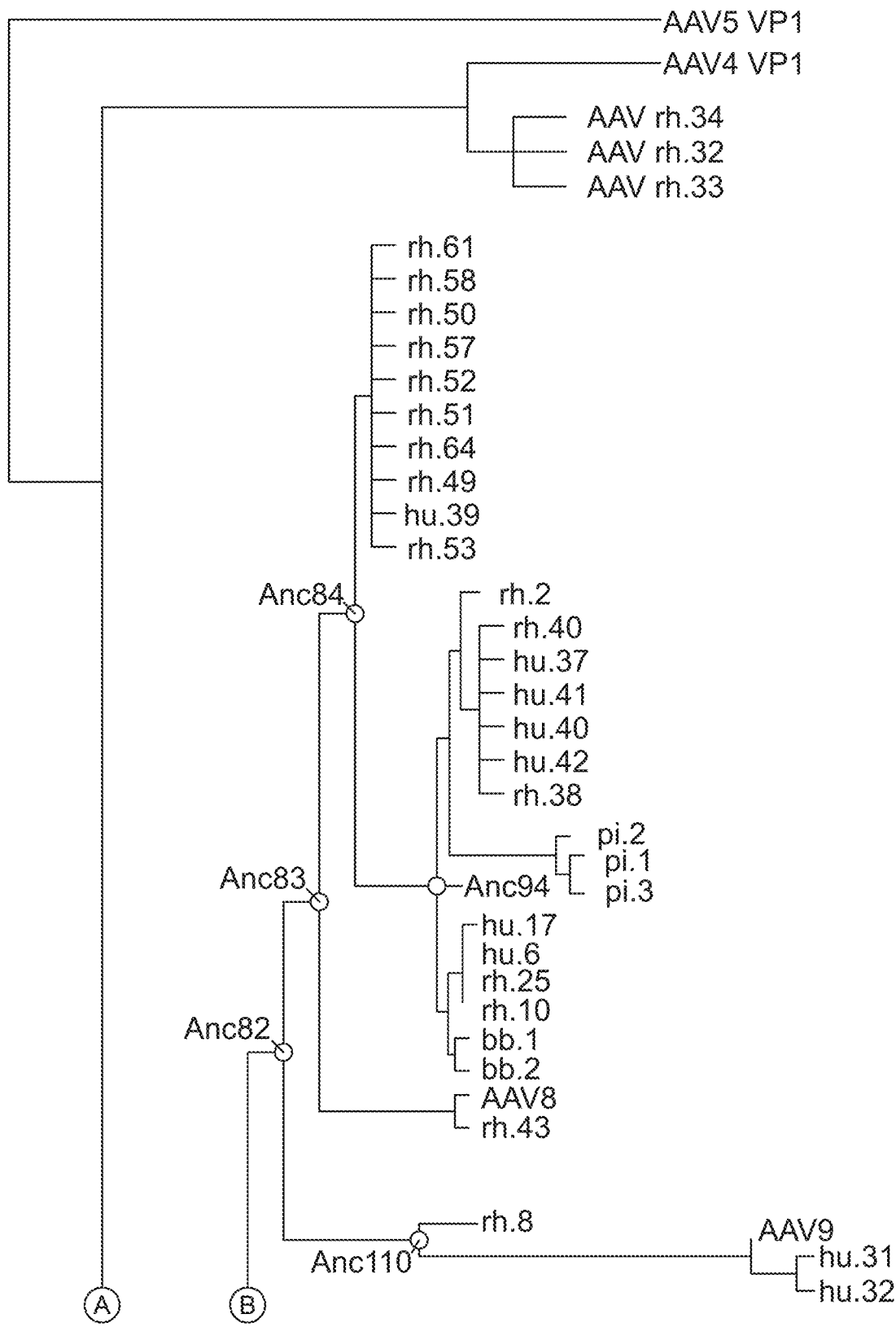
Figure 3:
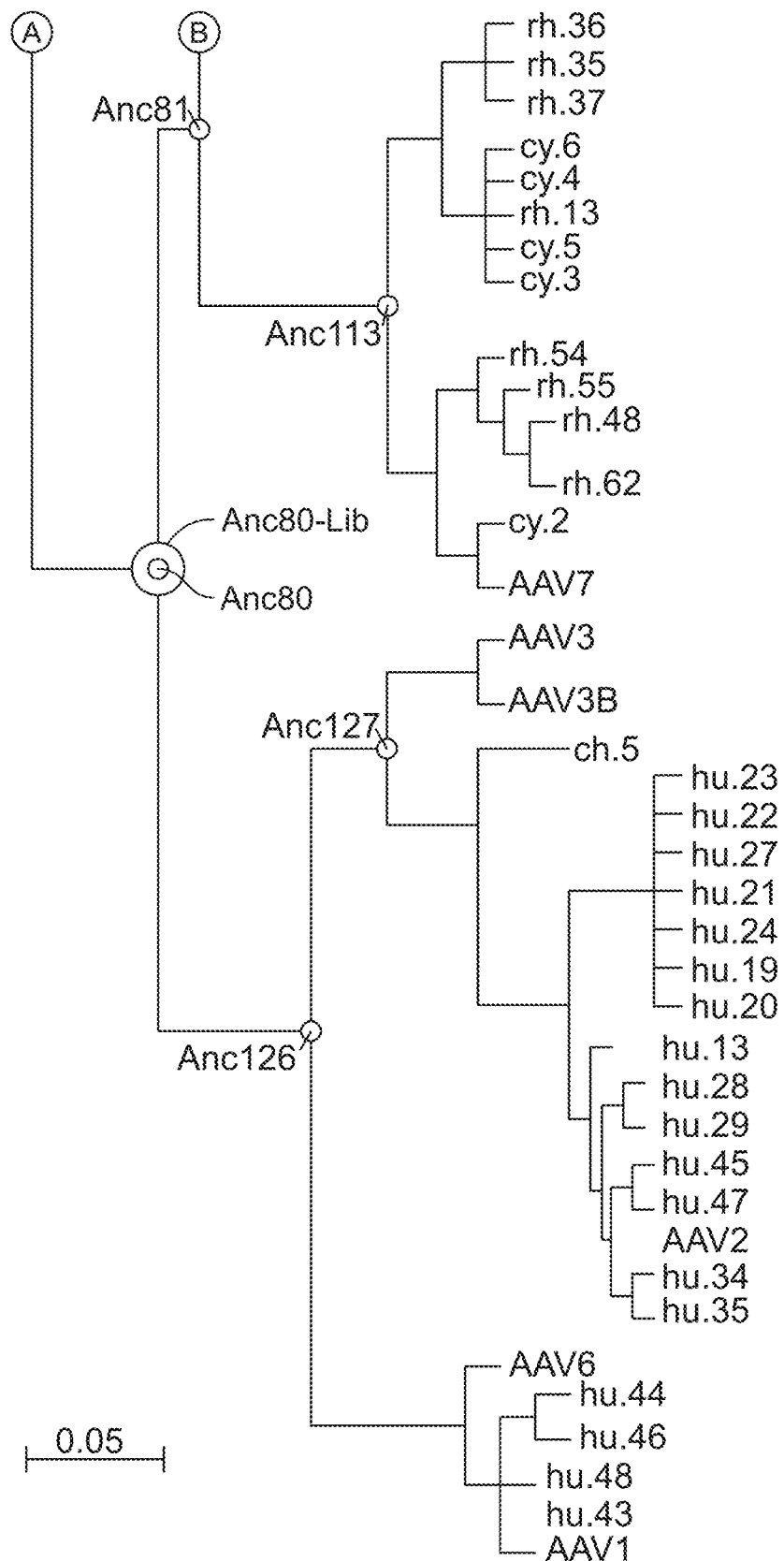

The methods described herein were applied to adeno-associated virus (AAV) using contemporary capsid sequences (described in detail in the Examples below). AAV is widely considered as a therapeutic gene transfer vector and a genetic vaccine vehicle, but exhibits a high seroprevalence in human populations. Using the methods described herein, a phylogenetic tree was assembled using contemporary AAV sequences (see FIGS. 3A-3C) and predicted ancestral scaffold sequences were obtained at the designated phylogenic node (Table 1). As used herein, an ancestral scaffold sequence refers to a sequence that is constructed using the methods described herein (e.g., using evolutionary probabilities and evolutionary modeling) and is not known to have existed in nature. As used herein, the ancestral scaffold sequences are different from consensus sequences, which are typically constructed using the frequency of nucleotides or amino acid residues at a particular position.

TABLE 1

| Node | Polypeptide (SEQ ID NO) | Nucleic Acid (SEQ ID NO) |
| --- | --- | --- |
| Anc80 | 1 | 2 |
| Anc81 | 3 | 4 |
| Anc82 | 5 | 6 |
| Anc83 | 7 | 8 |
| Anc84 | 9 | 10 |
| Anc94 | 11 | 12 |
| Anc113 | 13 | 14 |
| Anc126 | 15 | 16 |
| Anc127 | 17 | 18 |

The scaffold sequence of the Anc80 polypeptide is shown in SEQ ID NO:1, which is encoded by the scaffold sequence of the Anc80 nucleic acid shown in SEQ ID NO:2. The scaffold sequence of Anc80 contains 11 positions at which either of two residues were probable. Therefore, the Anc80 scaffold sequence represents 2048 (211) different sequences.

To demonstrate the effectiveness of the methods described herein for predicting the ancestral sequence of a virus or portion thereof, a library of the 2048 predicted ancestral sequences at the AAV Anc80 node was generated and, as described herein, demonstrated to form viable virus particles exhibiting less seroprevalence, in some instances, significantly less seroprevalance, than virus particles assembled with contemporary capsid polypeptides.

Methods of Making Ancestral Virus Particles

After the predicted ancestral sequence of a virus or portion thereof has been obtained, the actual nucleic acid molecule and/or polypeptide(s) can be generated, e.g., synthesized. Methods of generating an artificial nucleic acid molecule or polypeptide based on a sequence obtained, for example, in silico, are known in the art and include, for example, chemical synthesis or recombinant cloning. Additional methods for generating nucleic acid molecules or polypeptides are known in the art and are discussed in more detail below.

Once an ancestral polypeptide has been produced, or once an ancestral nucleic acid molecule has been generated and expressed to produce an ancestral polypeptide, the ancestral polypeptide can be assembled into an ancestral virus particle using, for example, a packaging host cell. The components of a virus particle (e.g., rep sequences, cap sequences, inverted terminal repeat (ITR) sequences) can be introduced, transiently or stably, into a packaging host cell using one or more vectors as described herein. One or more of the components of a virus particle can be based on a predicted ancestral sequence as described herein, while the remaining components can be based on contemporary sequences. In some instances, the entire virus particle can be based on predicted ancestral sequences.

Such ancestral virus particles can be purified using routine methods. As used herein, "purified" virus particles refer to virus particles that are removed from components in the mixture in which they were made such as, but not limited to, viral components (e.g., rep sequences, cap sequences), packaging host cells, and partially- or incompletely-assembled virus particles.

Once assembled, the ancestral virus particles can be screened for, e.g., the ability to replicate; gene transfer properties; receptor binding ability; and/or seroprevalence in a population (e.g., a human population). Determining whether a virus particle can replicate is routine in the art and typically includes infecting a host cell with an amount of virus particles and determining if the virus particles increase in number over time. Determining whether a virus particle is capable of performing gene transfer also is routine in the art and typically includes infecting host cells with virus particles containing a transgene (e.g., a detectable transgene such as a reporter gene, discussed in more detail below). Following infection and clearance of the virus, the host cells can be evaluated for the presence or absence of the transgene. Determining whether a virus particle binds to its receptor is routine in the art, and such methods can be performed in vitro or in vivo.

Determining the seroprevalence of a virus particle is routinely performed in the art and typically includes using an immunoassay to determine the prevalence of one or more antibodies in samples (e.g., blood samples) from a particular population of individuals. Seroprevalence is understood in the art to refer to the proportion of subjects in a population that is seropositive (i.e., has been exposed to a particular pathogen or immunogen), and is calculated as the number of subjects in a population who produce an antibody against a particular pathogen or immunogen divided by the total number of individuals in the population examined. Immunoassays are well known in the art and include, without limitation, an immunodot, Western blot, enzyme immunoassays (EIA), enzyme-linked immunosorbent assay (ELISA), or radioimmunoassay (RIA). As indicated herein, ancestral virus particles exhibit less seroprevalence than do contemporary virus particles (i.e., virus particles assembled using contemporary virus sequences or portions thereof). Simply by way of example, see Xu et al. (2007, Am. J. Obstet. Gynecol., 196:43.e1-6); Paul et al. (1994, J. Infect. Dis., 169:801-6); Sauerbrei et al. (2011, Eurosurv., 16(44): 3); and Sakhria et al. (2013, PLoS Negl. Trop. Dis., 7:e2429), each of which determined seroprevalence for a particular antibody in a given population.

As described herein, ancestral virus particles are neutralized by a person's, e.g., patient's, immune system to a lesser extent than are contemporary virus particles. Several methods to determine the extent of neutralizing antibodies in a serum sample are available. For example, a neutralizing antibody assay measures the titer at which an experimental sample contains an antibody concentration that neutralizes infection by 50% or more as compared to a control sample without antibody. See, also, Fisher et al. (1997, Nature Med., 3:306-12) and Manning et al. (1998, Human Gene Ther., 9:477-85).

With respect to the ancestral AAV capsid polypeptides exemplified herein, the seroprevalence and/or extent of neutralization can be compared, for example, to an AAV8 capsid polypeptide or virus particle that includes an AAV8 capsid polypeptide, or an AAV2 capsid polypeptide or virus particle that includes an AAV2 capsid polypeptide. It is generally understood in the art that AAV8 capsid polypeptides or virus particles exhibit a seroprevalance, and a resulting neutralization, in the human population that is considered low, while AAV2 capsid polypeptide or virus particles exhibit a seroprevalance, and a resulting neutralization, in the human population that is considered high. Obviously, the particular seroprevalence will depend upon the population examined as well as the immunological methods used, but there are reports that AAV8 exhibits a seroprevalence of about 22% up to about 38%, while AAV2 exhibits a seroprevalence of about 43.5% up to about 72%. See, for example, Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12. See, also, Calcedo et al., 2009, J. Infect. Dis., 199:381-90.

Predicted Adeno-Associated Virus (AAV) Ancestral Nucleic Acid and Polypeptide Sequences A number of different clones from the library encoding predicted ancestral capsid polypeptides from the Anc80 node were sequenced, and the amino acid sequences of representative AAV predicted ancestral capsid polypeptides are shown in SEQ ID NO: 19 (Anc80L27); SEQ ID NO: 20 (Anc80L59); SEQ ID NO: 21 (Anc80L60); SEQ ID NO: 22 (Anc80L62); SEQ ID NO: 23 (Anc80L65); SEQ ID NO: 24 (Anc80L33); SEQ ID NO: 25 (Anc80L36); and SEQ ID NO:26 (Anc80L44). Those skilled in the art would appreciate that the nucleic acid sequence encoding each amino acid sequence can readily be determined.

In addition to the predicted ancestral capsid polypeptides having the sequences shown in SEQ ID NOs: 19, 20, 21, 22, 23, 24, 25 or 26, polypeptides are provided that have at least 95% sequence identity (e.g., at least 96%, at least 97%, at least 98%, at least 99% or 100% sequence identity) to the predicted ancestral capsid polypeptides having the sequences shown in SEQ ID NOs: 19, 20, 21, 22, 23, 24, 25, or 26. Similarly, nucleic acid molecules are provided that have at least 95% sequence identity (e.g., at least 96%, at least 97%, at least 98%, at least 99% or 100% sequence identity) to the nucleic acid molecules encoding the ancestral capsid polypeptides (i.e., having at least 95% sequence identity).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the algorithm described by Altschul et al. (1997, Nucleic Acids Res., 25:3389 3402) as incorporated into BLAST (basic local alignment search tool) programs, available at ncbi.nlm.nih.gov on the World Wide Web. BLAST searches can be performed to determine percent sequence identity between a sequence (nucleic acid or amino acid) and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence and another sequence, the default parameters of the respective programs generally are used.

Figure 4:
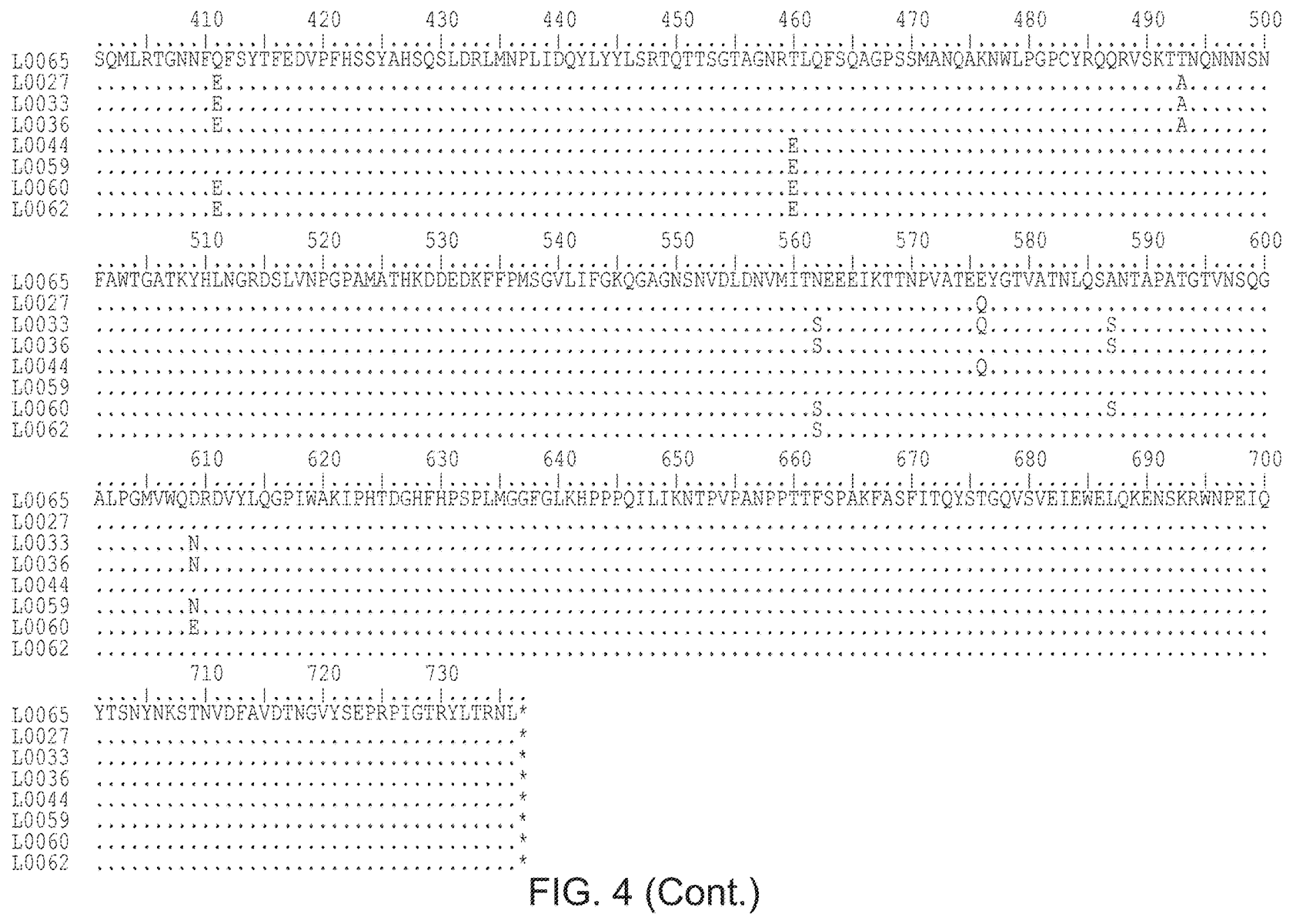
Figure 5A:
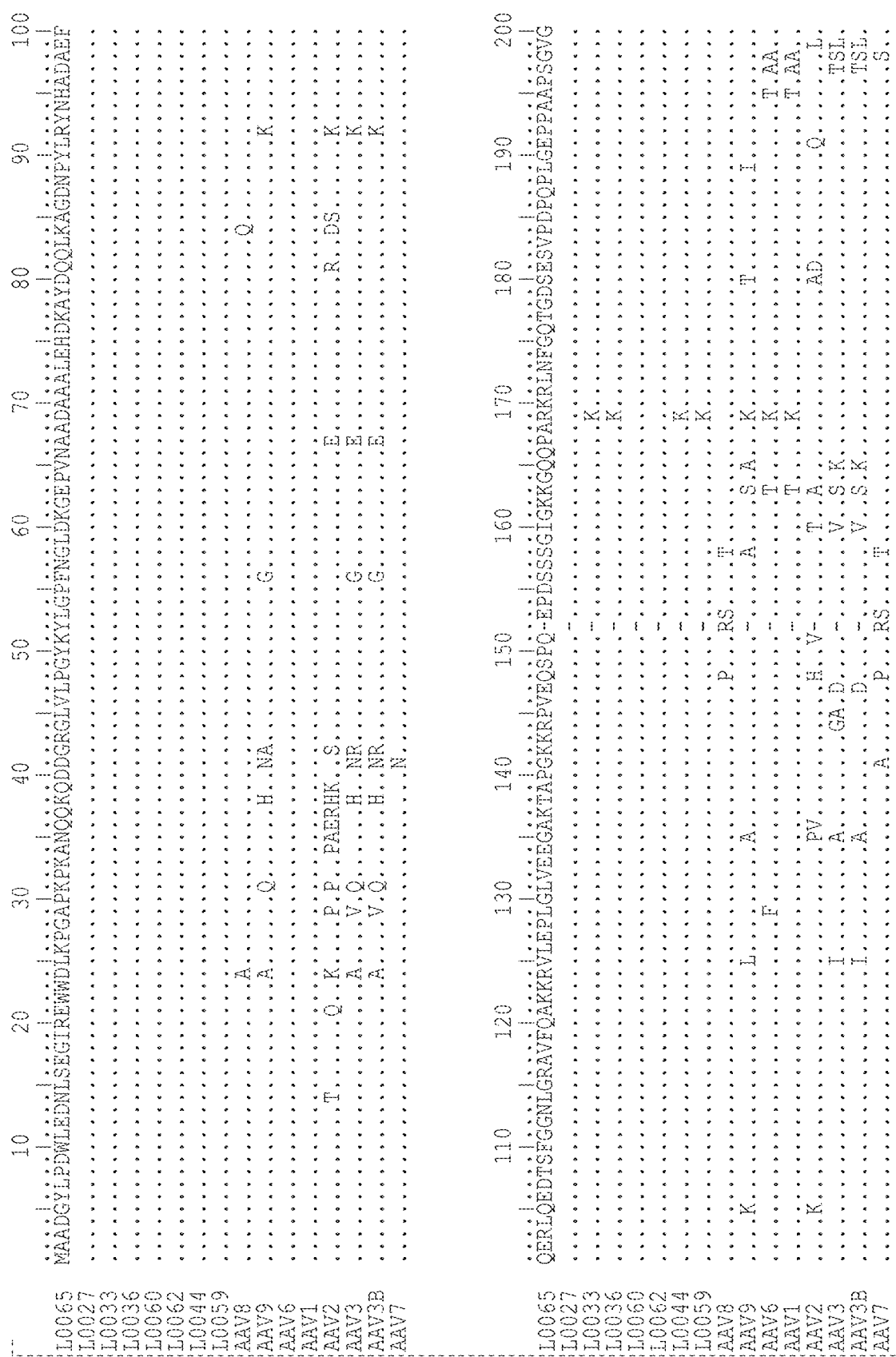
Figure 5B:
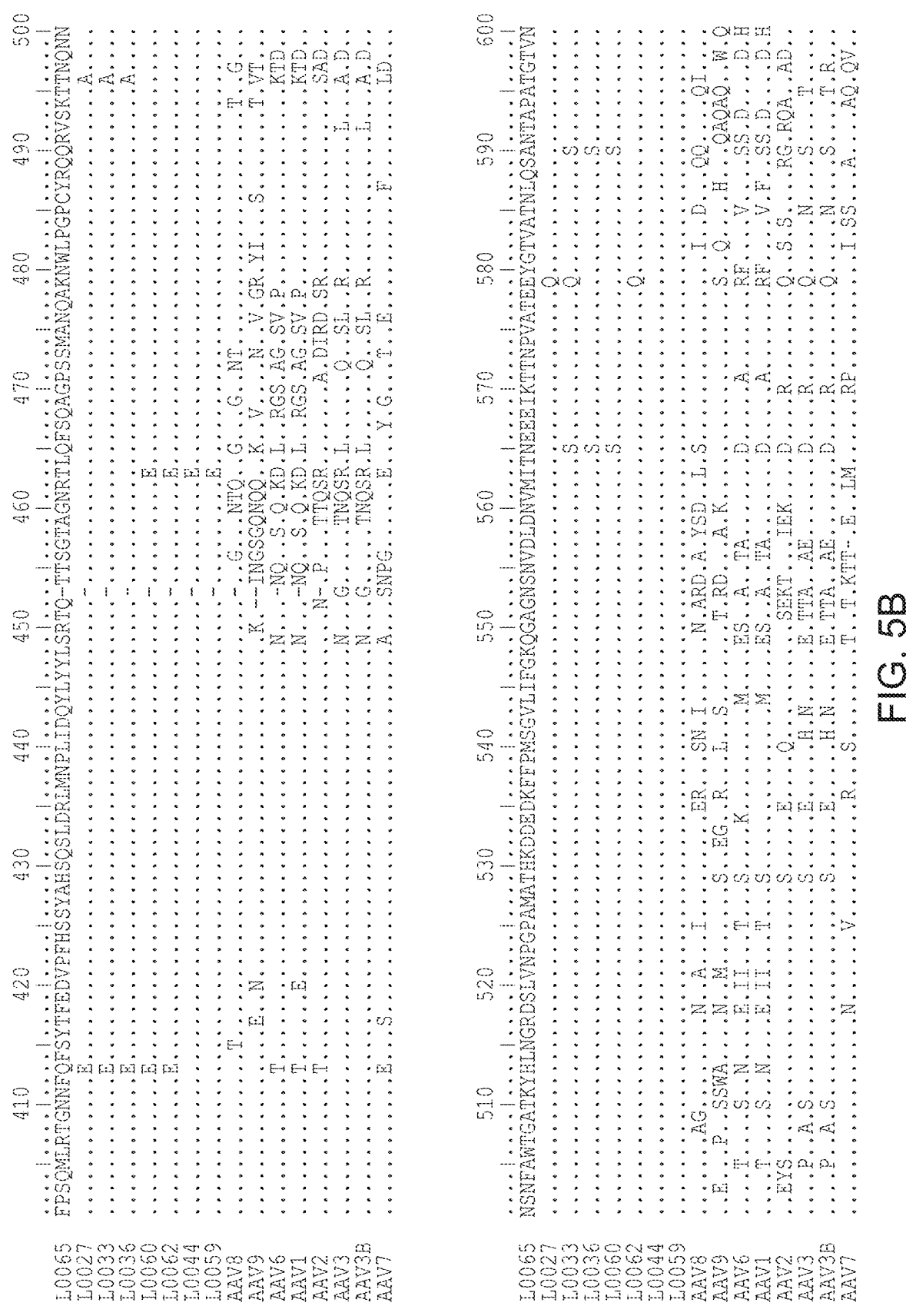
Figure 5B:
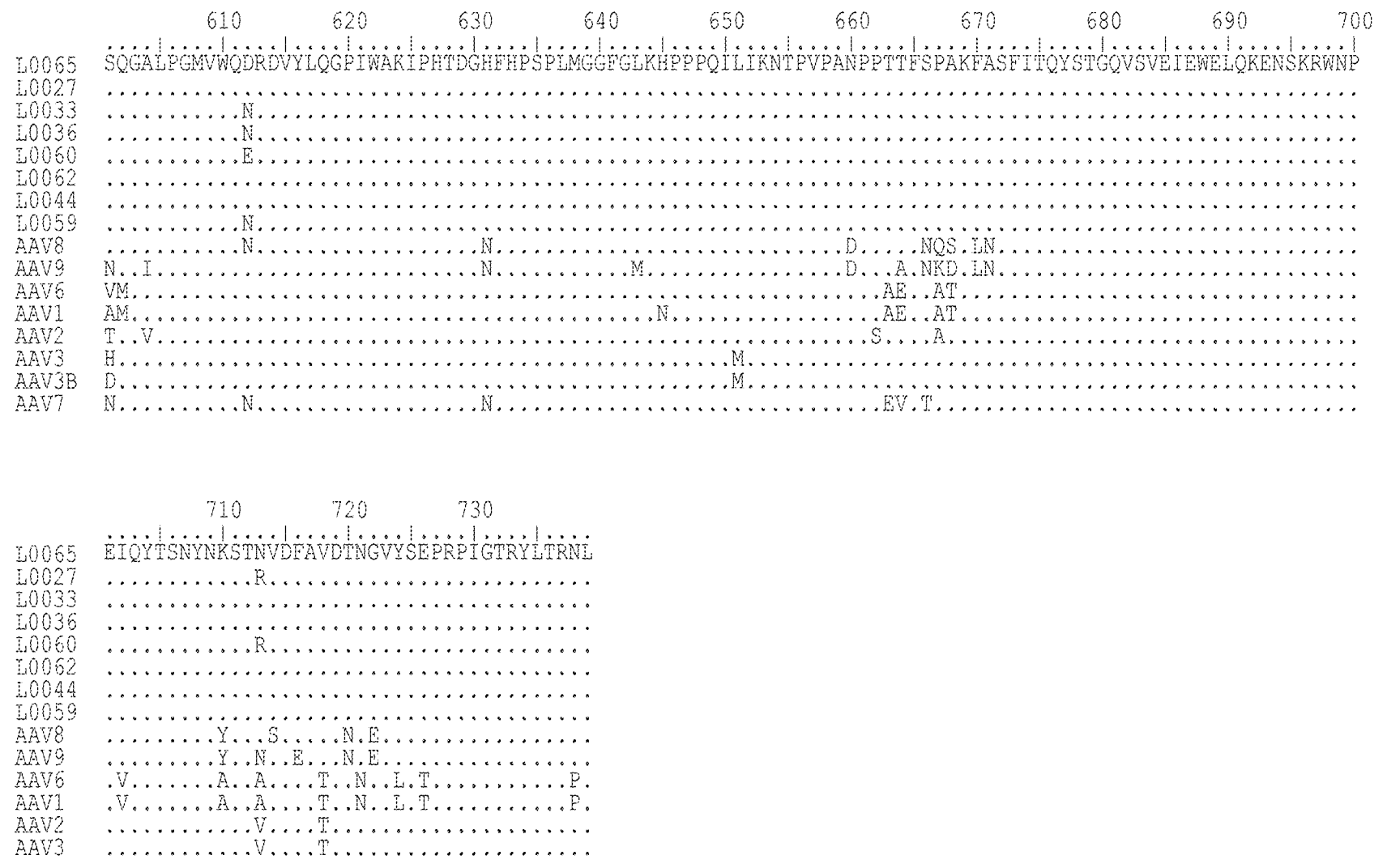

Representative alignments are shown in FIGS. 4A and 4B and FIGS. 5A and 5B. FIGS. 4A and 4B show an alignment of ancestral AAV VP1 capsid polypeptides, designated Anc80L65 (SEQ ID NO: 23), Anc80L27 (SEQ ID NO: 19), Anc80L33 (SEQ ID NO: 24), Anc80L36 (SEQ ID NO: 25), Anc80L44 (SEQ ID NO: 26), Anc80L59 (SEQ ID NO: 20), Anc80L60 (SEQ ID NO: 21), and Anc80L62 (SEQ ID NO: 22). The alignment shown in FIGS. 4A and 4B confirms the predicted variation at each of the 11 sites, and a single non-synonymous mutation at position 609E of Anc80L60 (SEQ ID NO: 21), which may be a cloning artifact. FIGS. 5A and 5B shows an alignment between ancestral AAV VP1 capsid polypeptides (Anc80L65 (SEQ ID NO: 23), Anc80L27 (SEQ ID NO: 19), Anc80L33 (SEQ ID NO: 24), Anc80L36 (SEQ ID NO: 25), Anc80L60 (SEQ ID NO: 21), Anc80L62 (SEQ ID NO: 22), Anc80L44 (SEQ ID NO: 26), and Anc80L59 (SEQ ID NO: 20)) and contemporary AAV VP1 capsid polypeptides (AAV8 (SEQ ID NO: 27), AAV9 (SEQ ID NO: 28), AAV6 (SEQ ID NO: 29), AAV1 (SEQ ID NO: 30), AAV2 (SEQ ID NO: 31), AAV3 (SEQ ID NO: 32), AAV3B (SEQ ID NO: 33), and AAV7 (SEQ ID NO: 34)). The alignment in FIGS. 5A and 5B shows that the ancestral AAV sequences have between about 85% and 91% sequence identity to contemporary AAV sequences.

Vectors containing nucleic acid molecules that encode polypeptides also are provided. Vectors, including expression vectors, are commercially available or can be produced by recombinant technology. A vector containing a nucleic acid molecule can have one or more elements for expression operably linked to such a nucleic acid molecule, and further can include sequences such as those encoding a selectable marker (e.g., an antibiotic resistance gene), and/or those that can be used in purification of a polypeptide (e.g., 6×His tag). Elements for expression include nucleic acid sequences that direct and regulate expression of nucleic acid coding sequences. One example of an expression element is a promoter sequence. Expression elements also can include one or more of introns, enhancer sequences, response elements, or inducible elements that modulate expression of a nucleic acid molecule. Expression elements can be of bacterial, yeast, insect, mammalian, or viral origin and vectors can contain a combination of expression elements from different origins. As used herein, operably linked means that elements for expression are positioned in a vector relative to a coding sequence in such a way as to direct or regulate expression of the coding sequence.

A nucleic acid molecule, e.g., a nucleic acid molecule in a vector (e.g., an expression vector, a viral vector) can be introduced into a host cell. The term "host cell" refers not only to the particular cell(s) into which the nucleic acid molecule has been introduced, but also to the progeny or potential progeny of such a cell. Many suitable host cells are known to those skilled in the art; host cells can be prokaryotic cells (e.g., E. coli) or eukaryotic cells (e.g., yeast cells, insect cells, plant cells, mammalian cells). Representative host cells can include, without limitation, A549, WEHI, 3T3, 10T1/2, BHK, MDCK, COS 1, COS 7, BSC 1, BSC 40, BMT 10, VERO, WI38, HeLa, 293 cells, Saos, C2C12, L cells, HT1080, HepG2 and primary fibroblast, hepatocyte and myoblast cells derived from mammals including human, monkey, mouse, rat, rabbit, and hamster. Methods for introducing nucleic acid molecules into host cells are well known in the art and include, without limitation, calcium phosphate precipitation, electroporation, heat shock, lipofection, microinjection, and viral-mediated nucleic acid transfer (e.g., transduction).

With respect to polypeptides, "purified" refers to a polypeptide (i.e., a peptide or a polypeptide) that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is considered "purified," but further can be removed from the components used to synthesize the polypeptide (e.g., amino acid residues). With respect to nucleic acid molecules, "isolated" refers to a nucleic acid molecule that is separated from other nucleic acid molecules that are usually associated with it in the genome. In addition, an isolated nucleic acid molecule can include an engineered nucleic acid molecule such as a recombinant or a synthetic nucleic acid molecule.

Polypeptides can be obtained (e.g., purified) from natural sources (e.g., a biological sample) by known methods such as DEAE ion exchange, gel filtration, and/or hydroxyapatite chromatography. A purified polypeptide also can be obtained, for example, by expressing a nucleic acid molecule in an expression vector or by chemical synthesis. The extent of purity of a polypeptide can be measured using any appropriate method, e.g., column chromatography, polyacrylamide gel electrophoresis, or HPLC analysis. Similarly, nucleic acid molecules can be obtained (e.g., isolated) using routine methods such as, without limitation, recombinant nucleic acid technology (e.g., restriction enzyme digestion and ligation) or the polymerase chain reaction (PCR; see, for example, PCR Primer: A Laboratory Manual, Dieffenbach & Dveksler, Eds., Cold Spring Harbor Laboratory Press, 1995). In addition, isolated nucleic acid molecules can be chemically synthesized.

Methods of Using Ancestral Viruses or Portions Thereof

An ancestral virus or portion thereof as described herein, particularly those that exhibit reduced seroprevalence relative to contemporary viruses or portions thereof, can be used in a number of research and/or therapeutic applications. For example, an ancestral virus or portion thereof as described herein can be used in human or animal medicine for gene therapy (e.g., in a vector or vector system for gene transfer) or for vaccination (e.g., for antigen presentation). More specifically, an ancestral virus or portion thereof as described herein can be used for gene addition, gene augmentation, genetic delivery of a polypeptide therapeutic, genetic vaccination, gene silencing, genome editing, gene therapy, RNAi delivery, cDNA delivery, mRNA delivery, miRNA delivery, miRNA sponging, genetic immunization, optogenetic gene therapy, transgenesis, DNA vaccination, or DNA immunization.

A host cell can be transduced or infected with an ancestral virus or portion thereof in vitro (e.g., growing in culture) or in vivo (e.g., in a subject). Host cells that can be transduced or infected with an ancestral virus or portion thereof in vitro are described herein; host cells that can be transduced or infected with an ancestral virus or portion thereof in vivo include, without limitation, brain, liver, muscle, lung, eye (e.g., retina, retinal pigment epithelium), kidney, heart, gonads (e.g., testes, uterus, ovaries), skin, nasal passages, digestive system, pancreas, islet cells, neurons, lymphocytes, ear (e.g., inner ear), hair follicles, and/or glands (e.g., thyroid).

An ancestral virus or portion thereof as described herein can be modified to include a transgene (in cis or trans with other viral sequences). A transgene can be, for example, a reporter gene (e.g., beta-lactamase, beta-galactosidase (LacZ), alkaline phosphatase, thymidine kinase, green fluorescent polypeptide (GFP), chloramphenicol acetyltransferase (CAT), or luciferase, or fusion polypeptides that include an antigen tag domain such as hemagglutinin or Myc) or a therapeutic gene (e.g., genes encoding hormones or receptors thereof, growth factors or receptors thereof, differentiation factors or receptors thereof, immune system regulators (e.g., cytokines and interleukins) or receptors thereof, enzymes, RNAs (e.g., inhibitory RNAs or catalytic RNAs), or target antigens (e.g., oncogenic antigens, autoimmune antigens)).

The particular transgene will depend, at least in part, on the particular disease or deficiency being treated. Simply by way of example, gene transfer or gene therapy can be applied to the treatment of hemophilia, retinitis pigmentosa, cystic fibrosis, leber congenital amaurosis, lysosomal storage disorders, inborn errors of metabolism (e.g., inborn errors of amino acid metabolism including phenylketonuria, inborn errors of organic acid metabolism including propionic academia, inborn errors of fatty acid metabolism including medium-chain acyl-CoA dehydrogenase deficiency (MCAD)), cancer, achromatopsia, cone-rod dystrophies, macular degenerations (e.g., age-related macular degeneration), lipopolypeptide lipase deficiency, familial hypercholesterolemia, spinal muscular atrophy, Duchenne's muscular dystrophy, Alzheimer's disease, Parkinson's disease, obesity, inflammatory bowel disorder, diabetes, congestive heart failure, hypercholesterolemia, hearing loss, coronary heart disease, familial renal amyloidosis, Marfan's syndrome, fatal familial insomnia, Creutzfeldt-Jakob disease, sickle-cell disease, Huntington's disease, fronto-temporal lobar degeneration, Usher syndrome, lactose intolerance, lipid storage disorders (e.g., Niemann-Pick disease, type C), Batten disease, choroideremia, glycogen storage disease type II (Pompe disease), ataxia telangiectasia (Louis-Bar syndrome), congenital hypothyroidism, severe combined immunodeficiency (SCID), and/or amyotrophic lateral sclerosis (ALS).

A transgene also can be, for example, an immunogen that is useful for immunizing a subject (e.g., a human, an animal (e.g., a companion animal, a farm animal, an endangered animal). For example, immunogens can be obtained from an organism (e.g., a pathogenic organism) or an immunogenic portion or component thereof (e.g., a toxin polypeptide or a by-product thereof). By way of example, pathogenic organisms from which immunogenic polypeptides can be obtained include viruses (e.g., picornavirus, enteroviruses, orthomyxovirus, reovirus, retrovirus), prokaryotes (e.g., Pneumococci, Staphylococci, *Listeria, Pseudomonas*), and eukaryotes (e.g., amebiasis, malaria, leishmaniasis, nematodes). It would be understood that the methods described herein and compositions produced by such methods are not to be limited by any particular transgene.

An ancestral virus or portion thereof, usually suspended in a physiologically compatible carrier, can be administered to a subject (e.g., a human or non-human mammal). Suitable carriers include saline, which may be formulated with a variety of buffering solutions (e.g., phosphate buffered saline), lactose, sucrose, calcium phosphate, gelatin, dextran, agar, pectin, and water. The ancestral virus or portion thereof is administered in sufficient amounts to transduce or infect the cells and to provide sufficient levels of gene transfer and expression to provide a therapeutic benefit without undue adverse effects. Conventional and pharmaceutically acceptable routes of administration include, but are not limited to, direct delivery to an organ such as, for example, the liver or lung, orally, intranasally, intratracheally, by inhalation, intravenously, intramuscularly, intraocularly, subcutaneously, intradermally, transmucosally, or by other routes of administration. Routes of administration can be combined, if desired.

The dose of the ancestral virus or portion thereof administered to a subject will depend primarily on factors such as the condition being treated, and the age, weight, and health of the subject. For example, a therapeutically effective dosage of an ancestral virus or portion thereof to be administered to a human subject generally is in the range of from about 0.1 ml to about 10 ml of a solution containing concentrations of from about $1\times10^{1}$ to $1\times10^{12}$ genome copies (GCs) of ancestral viruses (e.g., about $1\times10^{3}$ to $1\times10^{9}$ GCs). Transduction and/or expression of a transgene can be monitored at various time points following administration by DNA, RNA, or protein assays. In some instances, the levels of expression of the transgene can be monitored to determine the frequency and/or amount of dosage. Dosage regimens similar to those described for therapeutic purposes also may be utilized for immunization.

The methods described herein also can be used to model forward evolution, so as to modify or ablate one or more immunogenic domains of a virus or portion thereof.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Computational Prediction of Ancestral Sequences

A set of 75 different amino acid sequences of AAV capsids was obtained from a number of public databases including GenBank, and the sequences were aligned using the PRANK-MSA algorithm, version 121002, with the option "—F".

ProtTest3 (see, for example, Darriba et al., 2011, Bioinformatics, 27(8):1164-5; available at darwin.uvigo.es/software/prottest3 on the World Wide Web) was used to evaluate different models of polypeptide evolution (e.g., those included in ProTest3, namely, JTT, LG, WAG, VT, CpRev, RtRev, Dayhoff, DCMut, FLU, Blosum62, VT, HIVb, MtArt, MtMam) under different conditions (e.g., those included in ProTest3, namely, "+1", "+F", "+G", and combinations thereof). The JTT model (Jones et al., 1992, Comp. Appl. Biosci., 8:275-82) with +G and +F (Yang, 1993, Mol. Biol. Evol., 10:1396-1401; and Cao et al., 1994, J. Mol. Evol., 39:519-27) was selected based on its Aikake Information Criterion (AIC; Hirotugu, 1974, IEEE Transactions on Automatic Control, 19:716-23) score as implemented in ProTest3.

A phylogeny of AAV evolution was constructed using PhyML (Guindon and Gascuel, 2003, Systematic Biology, 52:696-704)). See FIG. 3. The tree was generated using the JTT+F substitution model with 4 discrete substitution categories and an estimated Gamma shape parameter. The resultant trees were improved via Nearest Neighbor Interchange (NNI) and Subtree Pruning and Re-Grafting (SPR), and assessed for significance via bootstrap and approximate likelihood-ratio test (aLRT; Anisimova and Gascuel, 2006, Systematic Biology, 55:539-52)) using the "SH-Like" variant.

The phylogenic tree constructed above was then used to estimate the ancestral states of the AAV capsid at every node interior to the phylogeny. The ancestral capsid sequences were reconstructed using maximum likelihood principles through the Phylogenetic Analysis by Maximum Likelihood (PAML) software (Yang, 1997, Comp. Applic. BioSci., 13:555-6; available at abacus.gene.ucl.ac.uk/software/paml.html on the World Wide Web) wrapped in Lazarus (Sourceforge at sfnet). More specifically, the Lazarus/PAML reconstruction was set to generate an amino acid reconstruction using the JTT+F substitution model using 4 gamma-distributed categories. AAV5 was used as an outgroup. Finally, the "I" option was added to place indels (i.e., coded binarily and placed via Maximum Parsimony using Fitch's algorithm) after the PAML reconstruction was done.

Because the reconstruction was done in a maximum-likelihood fashion, the likelihood that any residue was in a given position at a given node can be calculated. To do this, an additional script was written to identify all positions along the sequence with a calculated posterior probability beneath a certain threshold. A threshold of 0.3 was selected, meaning that any amino acid with a calculated posterior probability of greater than 0.3 was included in the synthesis of the library. These residues were selected to be variants of interest in the library.

To finalize the sequence, an additional utility had to be coded to select codons. A script was written to derive codons similar to those of another AAV sequence (AVVRh10, which has about 92% sequence identity to the Anc80 scaffold sequence) and apply a novel algorithm to substitute codons where there were sequence mismatches based on a codon-substitution matrix. The novel algorithm is shown below:

Given: amino acid sequence, Pt, with corresponding nucleotide sequence, Nt, where Nt codes for Pt; and protein sequence, Pi, where Pi exhibits strong homology to Pt.

Align Pi with Pt using Needleman-Wunsch using the Blosum62 table for scoring. Generate a new nucleotide sequence, Ni, by stepping through the protein alignment, using the corresponding codon from Nt, where the amino acid in Pt exactly matches that in Pi, the "best scoring" codon from the Codon-PAM matrix (Schneider et al., 2005, BMC Bioinform., 6:134) where there is a substitution, a gap where there exists a gap in Pi aligned against an amino-acid in Pt, and the most frequently occurring nucleotide in the Nt (coding for a given amino acid) where there exists an amino-acid in Pi aligned against a gap in Pt.

In addition, two single nucleotide changes were made to ablate transcription of assembly-activating protein (AAP), which is encoded out of frame within the AAV capsid gene in the wild type AAV. Since the coding of AAP (contemporary or ancestral) was not a part of this reconstruction, the expression of AAP was ablated by making a synonymous mutation in the cap sequence, and the AAP sequence was provided in trans during viral production.

Example 2—Expression of Ancestral AAV VP1 Sequences

Experiments were performed to determine whether predicted ancestral AAV capsid sequences can be used to make viral vectors.

A number of the predicted ancestral AAV capsid sequences were cloned. The library of ancestral capsids was transferred to a rep-cap expression plasmid to enable viral particle formation in transient transfection. To maintain appropriate expression levels and splicing of VP1, VP2, and VP3, library cap genes were cloned by cutting HindIII, located 5' of cap in the rep coding sequence, and SpeI, which was engineered between the cap stop codon and the polyadenylation signal. Consequently, to clone the ancestral capsids into a more conventional "REP/CAP" construct, the passaging-plasmid was digested with HindIII and SpeI, gel purified, and ligated into a similarly digested rep/cap plasmid.

Figure 6:
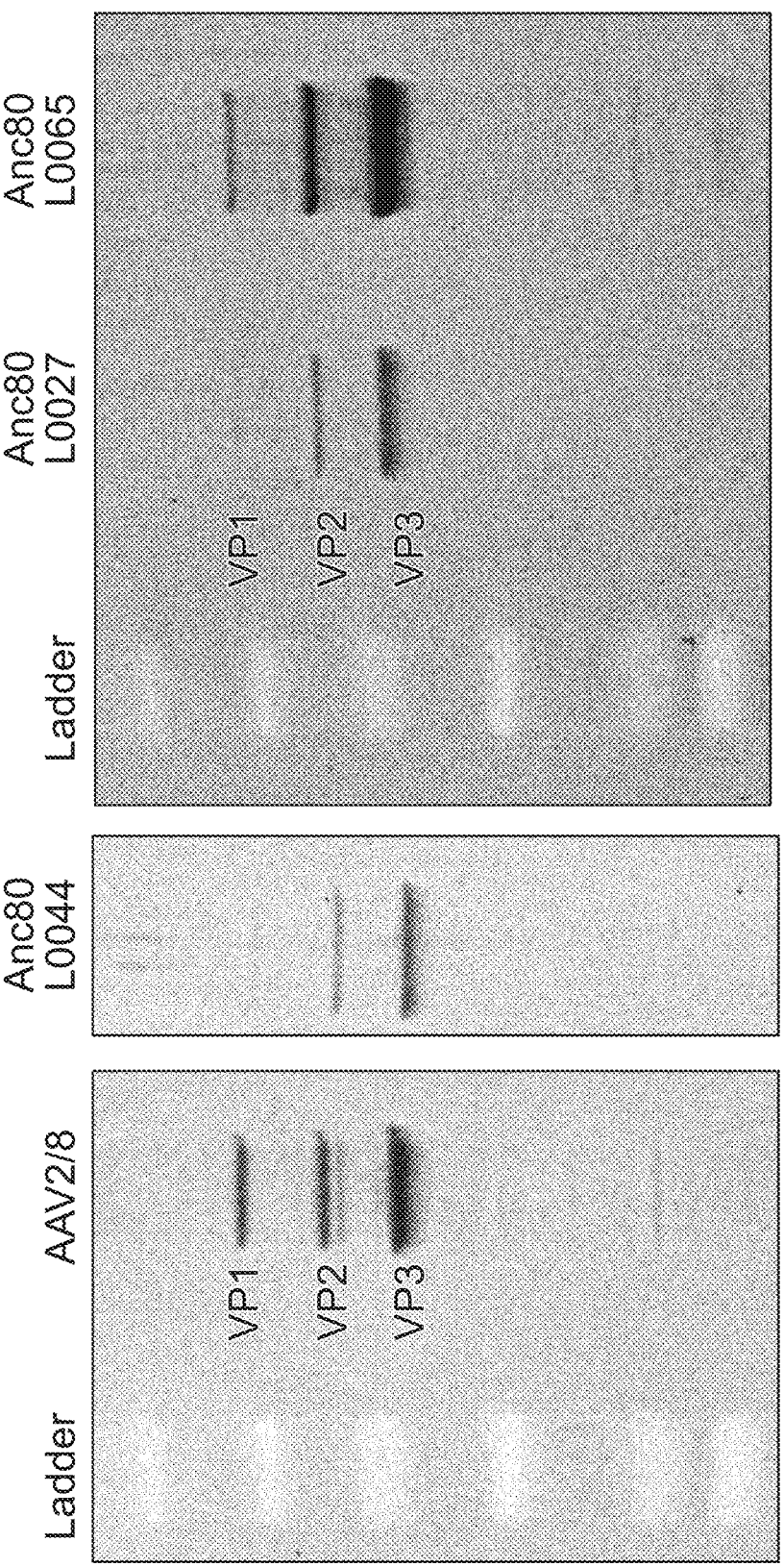

The expressed polypeptides were resolved on a 10% SDS gel. As shown in FIG. 6, the capsid polypeptides were appropriately expressed and spliced into VP1, VP2, and VP3 from a number of ancestral AAV sequences (Anc80L44, Anc80L27, and Anc80L65) as well as from a contemporary AAV sequence, AAV2/8.

Example 3—Viral Titration

AAV was produced in HEK293 cells via transient co-transfection of plasmids encoding all elements required for viral particle assembly. Briefly, HEK293 cells were grown to 90% confluency and transfected with (a) the viral genome plasmid encoding the luciferase transgene (expressed by the CMV promoter) flanked by AAV2 ITRs, (b) the AAV packaging plasmid encoding AAV2 rep and the synthesized capsid proteins disclosed herein, (c) AAV2-AAP expressing capsid, and (d) adenoviral helper genes needed for AAV packaging and assembly. Cells were incubated at 37° C. for 2 days, and cells and media were harvested and collected.

The cell-media suspension was lysed by 3 consecutive freeze-thaw cycles. Next, the lysate was cleared by centrifugation and treated with an enzyme under conditions to perform exhaustive DNA digestion, here BENZONASE™, to digest any DNA present outside of the virus particle. The AAV preparation was diluted to fall within the linear measurement range of a control DNA template, in this case linearized plasmid with identical TAQMAN™ primer and probe binding sequence as compared to the vector genome. TAQMAN™ PCR was performed with primers and probe annealing to the viral vector genome of choice. Titer was calculated based on the TAQMAN™ measurement in genome copies (GC) per milliliter (ml) as shown in Table 2 below.

TABLE 2

| Titers (GC/ml) | Small scale #1 | Small scale #2 |
| --- | --- | --- |
| AAV2/2 | $1.12 \times 10^9$ | $1.99 \times 10^9$ |
| AAV2/8 | $4.17 \times 10^{10}$ | $5.91 \times 10^{10}$ |
| Anc80L27 | $8.01 \times 10^8$ | $1.74 \times 10^9$ |
| Anc80L44 | $1.52 \times 10^9$ | $1.43 \times 10^9$ |
| Anc80L65 | $1.42 \times 10^9$ | $2.05 \times 10^9$ |
| No capsid control | $5.23 \times 10^5$ | $7.25 \times 10^5$ |

Small scale vector production results on ancestrally reconstructed AAV capsid particles demonstrated yields that were similar to AAV2, but reduced relative to AAV8, both of which are vector preparations based on contemporary AAVs.

Example 4 In Vitro Viral Transduction

In vitro viral transductions were performed to evaluate the ability of viruses containing the predicted ancestral AAV sequences to infect cells.

Following high throughput vector production using the Anc80 library of sequences, HEK293 cells were transduced with each viral vector. In addition to an Anc80 sequence, each viral vector contained a luciferase transgene. Luciferase was measured by quantification of bioluminescence in a 96 well plate reader following addition of luciferin substrate to the transduced cells or cell lysate. Following quantification, a heat map of luciferase expression in four concatenated 96-well plates was produced (excluding a column of controls in each plate). Due to the large number of insertions, deletions, and transitions associated with the process of high throughput vector production, many of the vectors were non-functional. For purposes herein, only viruses that were functional in this assay (i.e., able to transduce HEK293 cells and express the transgene) were evaluated further.

Figure 7:
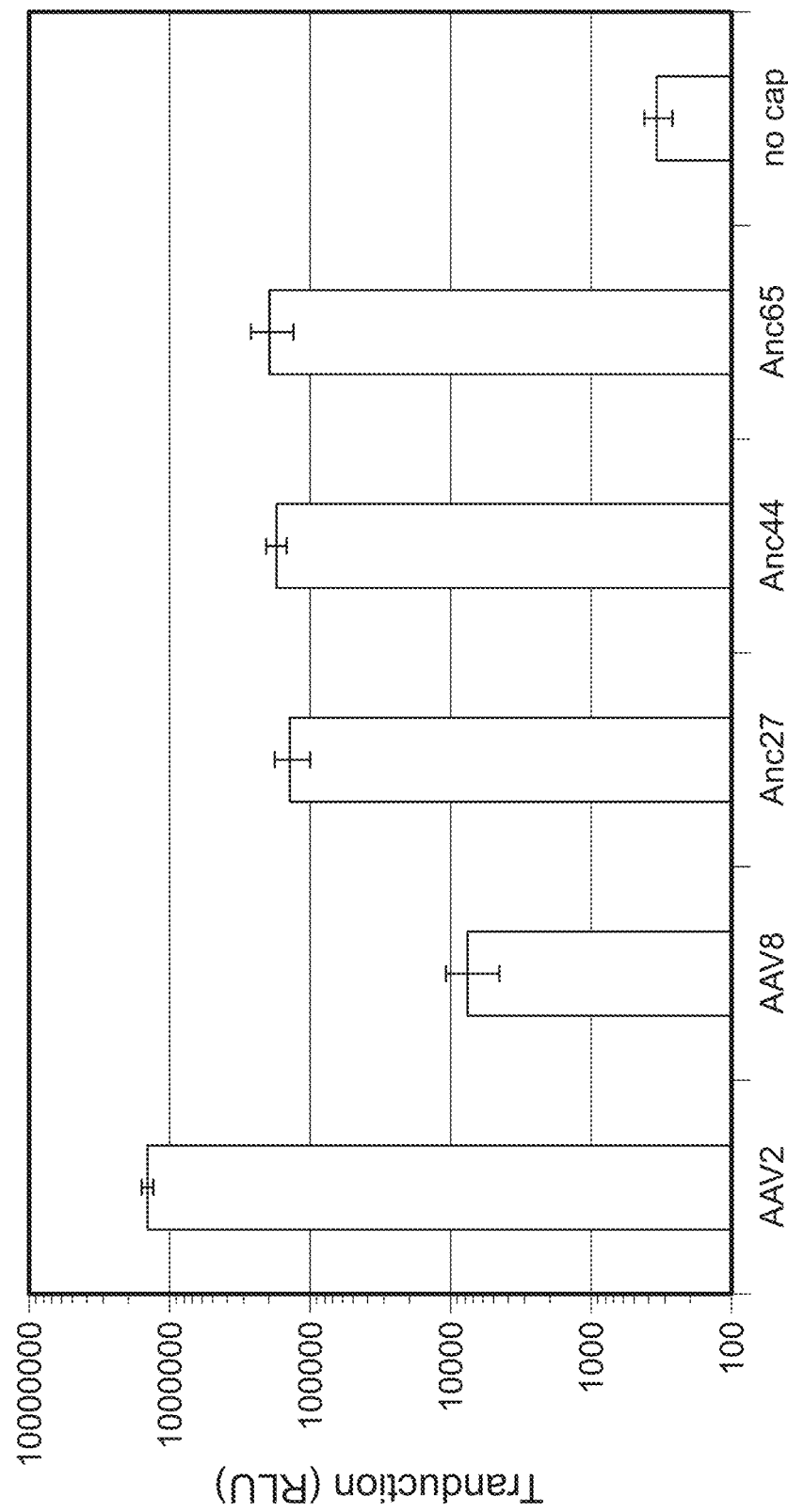
FIG. 7 is a graph showing the luciferase activity in HEK293 cells transduced with ancestral AAV vectors.

HEK293 cells were transduced, at equal multiplicity of infection (MOI) of $1 \times 10^4$ genome copies (GC) per cell, with two contemporary AAV vectors (AAV2/2 and AAV2/8) and three predicted ancestral AAV vectors (Anc80L27, Anc80L44, and Anc80L65). Each vector contained either a luciferase-encoding transgene or an eGFP-encoding transgene. Cells were imaged 60 hours later using the GFP channel of an AMG EvosF1 Optical Microscope. FIG. 7 shows the luciferase expression following the in vitro transduction. Each of the ancestral AAV viruses demonstrated efficient transduction of HEK293 cells.

Example 5 In Vivo Retinal Transduction

Retinal transductions were performed to determine whether or not the ancestral AAV vectors are able to target murine retinal cells in vivo.

Murine eyes were transduced with $2 \times 10^8$ genome copies (GC) of three different ancestral AAVs (Anc80L27, Anc80L44, and Anc80L65) and a contemporary AAV (AAV2/8), all of which included an eGFP-encoding transgene. For transductions, each AAV vector was surgically delivered below the retina by generating a space between the photoreceptor and retinal pigment epithelium layer through delivery of a vector bolus with an injection device. The vector bolus was left in the sub-retinal space and the sub-retinal detachment resolved over time. GFP expression was monitored non-invasively by fundus photography of the retina of the animal following pupil dilation with TROPI-CAMIDE™. All of the presented retinas demonstrated varying degrees of successful targeting of ancestral AAVs to the retina.

Retinal histology also was performed and visualized under fluorescent microscopy to identify the transduced cell type(s). Histology was performed on a murine retina transduced with the Anc80L65 ancestral AAV vector as described above. Anc80L65-mediated eGFP expression was evident in the outer nuclear layer (ONL), the inner segments (IS), and the retinal pigment epithelium (RPE), indicating that the ancestral Anc80L65 vector targets murine photoreceptors and retinal pigment epithelial cells.

Example 6—Neutralizing Antibody Assay

Neutralizing antibody assays were performed to evaluate whether or not an ancestral AAV virus is more resistant to antibody-neutralization than a contemporary AAV virus. Neutralizing antibody assays measure the antibody concentration (or the titer at which an experimental sample contains an antibody concentration) that neutralizes an infection by 50% or more as compared to a control in the absence of the antibody.

Serum samples or IVIG stock solution (200 mg/ml) were serially diluted by 2-fold, and undiluted and diluted samples were co-incubated with an ancestral AAV virus, Anc80L65, and a contemporary AAV virus, AAV2/8, at a MOI of $10^4$ for about 30 minutes at 37° C. Each virus included a luciferase transgene. The admixed vector and an antibody sample then were transduced into HEK293 cells. For these experiments, the antibody sample used was intravenous immunoglobulin (IVIG), pooled IgGs extracted from the plasma of over one thousand blood donors (sold commercially, for example, as GAMMAGARD™ (Baxter Healthcare; Deerfield, IL) or GAMUNEX™ (Grifols; Los Angeles, CA)). 48 hours following initiation of transduction, cells were assayed by bioluminescence to detect luciferase. Neutralizing antibody titer was determined by identifying the dilution of sample for which 50% or more neutralization (transduction of sample/transduction of control virus in absence of sample) was reached.

Example 7—Characterization of Anc80

Based on the methods described herein, the most probable Anc80 sequence (as determined through posterior probability) was obtained and designated Anc80L1 (SEQ ID NO:35 shows the nucleic acid sequence of the Anc80L1 capsid and SEQ ID NO:36 shows the amino acid sequence of the Anc80L1 VP1 polypeptide). The Anc80 probabilistic library also was synthesized using the sequences described herein by a commercial company and sub-cloned into expression vectors.

The Anc80 library was clonally evaluated for vector yield and infectivity in combined assays. Out of this screening, Anc80L65 (SEQ ID NO:23), as well as several other variants, were further characterized.

The Anc80 library and Anc80L65 were compared in terms of sequence difference (FIG. 8; % up from diagonal, # of amino acid differences below). Using NCBI-BLAST, the closest publically available sequence to Anc80L65 is rh10 (GenBank Accession No. AAO88201.1).

FIG. 9 shows that Anc80L65 produced vector yields equivalent to AAV2 (Panel A), generated virus particles under Transmission Electroscopy (TEM) (Panel B), and biochemically produced the AAV cap and the VP1, 2 and 3 proteins based on SDS page under denaturing conditions (Panel C) and Western Blotting using the AAV capsid antibody, B1 (Panel D). These experiments are described in more detail in the following paragraphs.

Figure 9A:
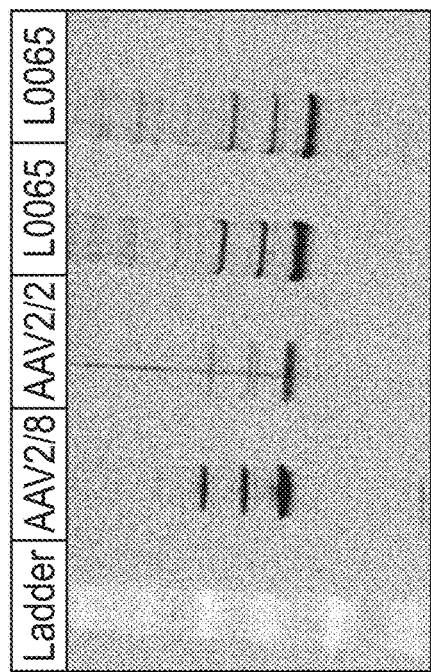

Briefly, AAV2/8, AAV2/2, AAV2/Anc80L27, AAV2/Anc80L44, and AAV2/Anc80L65 vectors were produced in small scale containing a reporter construct comprised of eGFP and firefly luciferase under a CMV promoter were produced in small scale. Titers of these small scale preparations of viruses were then obtained via qPCR. Based on these experiments, Anc80L27, Anc80L44, and Anc80L65 vectors were found to produce viral levels comparable to that of AAV2 (FIG. 9A).

Figure 9C:
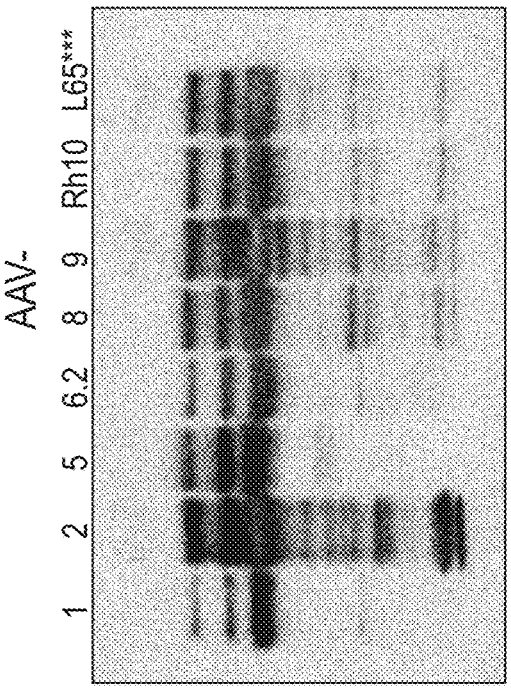
Figure 9B:
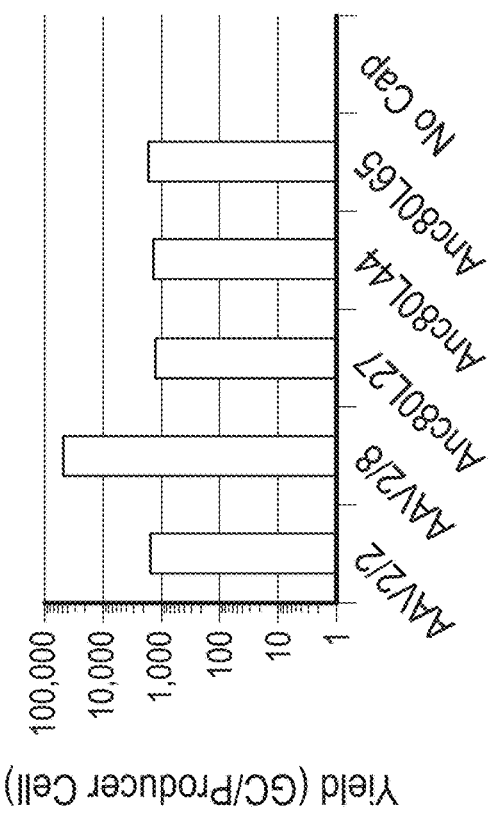

To confirm that the Anc80L65 capsid proteins assembled into intact virus-like particles of the proper size and conformation, micrographs were obtained using transmission electron microscopy (TEM). A large scale, purified preparation of Anc80-L065 was loaded onto polyvinyl formal (FORMVAR®) coated copper grids and was then stained with uranyl acetate. Micrographs revealed intact, hexagonal particles with diameters between 20 and 25 nm (FIG. 9B).

Figure 9D:
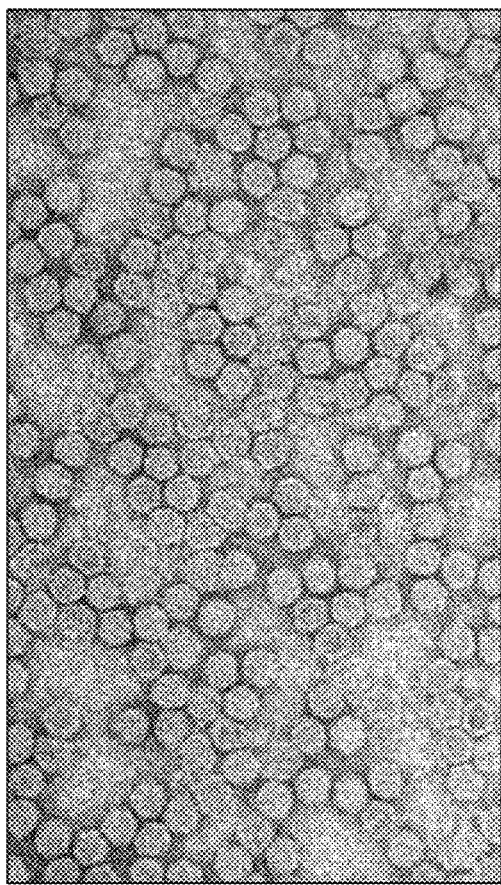

In order to determine whether the synthetic ancestral capsid genes were properly processed (i.e. spliced and expressed), large-scale purified preparations of AAV2/8, AAV2/2, and AAV2/Anc80L65 vectors were loaded onto an SDS-PAGE gel (1E10 GC/well) under denaturing conditions. Bands representing viral capsid proteins VP1, VP2, and VP3 were clearly present for each vector preparation (FIG. 9C). Western blotting with the AAV capsid antibody B1 further confirmed that these bands represented the predicted proteins (FIG. 9D).

In addition, FIG. 10 shows that Anc80L65 infected mammalian tissue and cells in vitro on HEK293 cells at MOI 10E4 GC/cell using GFP as readout (Panel A) or luciferase (Panel B) versus AAV2 and/or AAV8 controls. Anc80L65 also was efficient at targeting liver following an IV injection of the indicated AAV encoding a nuclear LacZ transgene (top row, Panel C), following direct intramuscular (IM) injection of the indicated AAV encoding GFP (middle row, Panel C), and following subretinal injection with the indicated AAV encoding GFP (bottom row, Panel C). These experiments are described in more detail in the following paragraphs.

To obtain a relative measure of the infectivity of ancestral virions, crude preparations of AAV2/2, AAV2/8, AAV2/Anc80L65, AAV2/Anc80L44, AAV2/Anc80L27, AAV2/Anc80L121, AAV2/Anc80L122, AAV2/Anc80L123, AAV2/Anc80L124, and AAV2/Anc80L125 containing a bi-cistronic reporter construct that includes an eGFP and firefly luciferase sequences under control of a CMV promoter were produced. 96-well plates confluent with HEK293 cells were then subjected to transduction with each vector at an MOI of 1E4 GC/cell (titers obtained via qPCR as above). 48 hours later, fluorescent microscopy confirmed the presence of GFP in transduced cells (FIG. 10A). Cells were then assayed for the presence of luciferase (FIG. 10B), which determined that expression of luciferase in cells transduced with Anc80-derived vectors was in-between that of cells transduced with AAV8 (lower level of transduction) and AAV2 (higher level of transduction).

To assess the relative efficiency of gene transfer in an in vivo context, purified high-titer preparations of AAV2/2, AAV2/8, and AAV2/Anc80L65 were obtained. 3.9E10 GC of each vector, encapsidating a transgene encoding nuclear LacZ under control of a TBG promoter, were injected into C57BL/6 mice (3 mice per condition) via IP injection following general anesthetization. 28 days post-injection, mice were sacrificed and tissues were collected. Livers were sectioned via standard histological techniques and stained for beta-galactosidase. Sections were then imaged under a microscope and representative images are shown in FIG. 10C, top row.

Vectors of the same serotypes were then obtained containing a bicistronic transgene encoding eGFP and hA1AT under control of a pCASI promoter. To assess the ability of Anc80L65 to transduce murine skeletal muscle, 1E10 GC of each vector was injected into skeletal muscle of C57BL/6 mice (5 mice per condition) following general anesthetization. 28 days post-injection, mice were sacrificed, tissues were cryosectioned, and the presence of eGFP was assessed using fluorescent confocal microscopy (blue is DAPI, green is eGFP). Representative images are shown in FIG. 10C, middle row. These experiments demonstrated that Anc80L65 vectors were capable of transducing murine skeletal muscle via intramuscular injection.

Vectors of the same serotypes were obtained, this time encapsidating constructs encoding only an eGFP transgene under control of a CMV promoter. 2E9 particles were injected sub-retinally into C57BL/6 mice following general anesthetization. 28 days post-injection, mice were sacrificed and the eyes were collected, cryosectioned, and the presence of eGFP was assessed using fluorescent confocal microscopy (blue is DAPI, green is eGFP). Representative images are shown in FIG. 10C, bottom row. These experiments demonstrate that Anc80L65 vectors are able to transduce murine retina at a level that is comparable to AAV8 vectors.

Briefly, purified, high titer preparations of AAV2/8, AAV2/2, AAV2/rh32.33, and AAV2/Anc80L65 viral vectors encapsidating a bicistronic transgene that includes eGFP and firefly luciferase under control of a CMV promoter were obtained. These vectors were then either incubated with two-fold serial dilutions of IVIG (10 mg, 5 mg, 2.5 mg, etc.) or incubated without IVIG (1E9 GC per condition). Following incubation, vectors were used to transduce HEK293 cells at an MOI of 1E4 per well (one dilution per well).

Example 8—Generation of Additional Ancestral AAV Capsids

The most probable ancestral AAV capsid sequences (as determined through posterior probability) were then synthesized through a commercial lab (Gen9) and provided as linear dsDNA. These amino acid sequences were then compared to those of extant AAVs in order to ascertain the degree to which they differ (FIG. 11). Each ancestral VP1 protein differs from those of selected representative extant AAVs by between 3.6% and 9.3% (FIG. 11A), while the ancestral VP3 proteins differ by between 4.2 and 9.4% (FIG. 11B). These capsids were each subcloned into AAV production plasmids (pAAVector2/Empty) via restriction enzyme digestion (HindIII & SpeI) and T4 ligation. These clones were confirmed via restriction digestion and Sanger sequencing, and medium scale preparations of plasmid DNA were then produced.

Each of these plasmids were then used to produce AAV vectors containing a reporter gene encoding both eGFP and firefly luciferase. These vectors were produced in triplicate in small scale as previously described. Crude preparations of the virus were then titered via qPCR and were found to produce between 2.71% and 183.1% viral particles relative to AAV8 (FIGS. 12 and 13). These titers were then used to set up a titer controlled experiment to assess relative infectivity. Anc126 was not titer controlled due to its significantly depressed production, and consequently, the data regarding the infectivity of Anc126 cannot be accurately compared to the infectivity of the other viruses in the experiment. The other vectors were used to transduce HEK293 cells at a multiplicity of infection (MOI) of 1.9E3 GC/cell.

60 hours post transduction, cells were assessed for GFP expression via fluorescence microscopy. eGFP positive cells were detected under each of the conditions except for the negative control (FIG. 14). This indicates that each of the ancestral sequences that were predicted, synthesized, and cloned is capable of producing viable, infectious virus particles. To get an idea of the relative levels of infectivity, luciferase assays also were performed on the same cells. The results indicate that each of the ancestral vectors is capable of transducing HEK293 cells between 28.3% and 850.8% relative to AAV8 (FIGS. 15 and 16). It is noted that Anc126 was excluded from the analysis of relative transduction since it was not titer-controlled.

In summary, eight novel ancestral AAV capsid genes were synthesized and used in the production of functional viral vectors along with AAV8, AAV2, and the previously described Anc80L65 vectors. Production and infectivity were assessed in vitro and a summary of those findings is shown in FIG. 17.

Example 9—Vectored Immunoprophylaxis

In vectored immunoprophylaxis, gene therapy vehicles (such as AAV) are used to deliver transgenes encoding broadly neutralizing antibodies against infectious agents. See, for example, Balazs et al. (2013, Nat. Biotechnol., 31:647-52); Limberis et al. (2013, Sci. Transl. Med., 5:187ra72); Balazs et al. (2012, Nature, 481:81-4); and Deal et al. (2014, PNAS USA, 111:12528-32). One advantage of this treatment is that the host produces the antibodies in their own cells, meaning that a single administration has the potential to confer a lifetime of protection against etiologic agents.

Example 10—Drug Delivery Vehicles

LUCENTIS® (ranibizumab) and AVASTIN® (bevacizumab) are both anti-angiogenesis agents based on the same humanized mouse monoclonal antibodies against vascular endothelial growth factor A (VEGF-A). Although bevacizumab is a full antibody and ranibizumab is a fragment (Fab), they both act to treat wet age-related macular degeneration through the same mechanism—by antagonizing VEGF. See, for example, Mao et al. (2011, Hum. Gene Ther., 22:1525-35); Xie et al. (2014, Gynecol. Oncol., doi: 10.1016/j.ygyno.2014.07.105); and Watanabe et al. (2010, Gene Ther., 17:1042-51). Because both of these molecules are proteins, they can be encoded by DNA and produced in cells transduced with vectors containing a transgene, and are small enough to be packaged into AAV vectors.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

SEQUENCE LISTING

```
Sequence total quantity: 44
SEQ ID NO: 1             moltype = AA  length = 736
FEATURE                  Location/Qualifiers
VARIANT                  168
                         note = /replace="Arg"
VARIANT                  204
                         note = /replace="Ser"
VARIANT                  266
                         note = /replace="Gly"
VARIANT                  311
                         note = /replace="Lys"
VARIANT                  411
                         note = /replace="Gln"
VARIANT                  460
                         note = /replace="Glu"
VARIANT                  493
                         note = /replace="Thr"
VARIANT                  562
                         note = /replace="Asn"
VARIANT                  576
                         note = /replace="Glu"
VARIANT                  587
                         note = /replace="Ala"
VARIANT                  609
                         note = /replace="Asp"
REGION                   1..736
                         note = misc_feature - /note="Variant residues given in the
                         sequence have no preference with respect to those in the
                         annotations for variant positions"
source                   1..736
                         mol_type = protein
                         organism = Adeno-associated virus
SEQUENCE: 1
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPAKKR LNFGQTGDSE   180
SVPDPQPLGE PPAAPSGVGS NTMAAGGGAP MADNNEGADG VGNASGNWHC DSTWLGDRVI   240
TTSTRTWALP TYNNHLYKQI SSQSGASTND NTYFGYSTPW GYFDFNRFHC HFSPRDWQRL   300
INNNWGFRPK RLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRT LQFSQAGPSS MANQAKNWLP   480
GPCYRQQRVS KTANQNNNSN FAWTGATKYH LNGRDSLVNP GPAMATHKDD EDKFFPMSGV   540
LIFGKQGAGN SNVDLDNVMI TSEEEIKTTN PVATEQYGTV ATNLQSSNTA PATGTVNSQG   600
ALPGMVWQNR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                  736

SEQ ID NO: 2             moltype = DNA  length = 2208
FEATURE                  Location/Qualifiers
variation                502..504
                         note = /replace="aaa"
variation                610..612
                         note = /replace="agc"
variation                796..798
                         note = /replace="ggc"
variation                931..933
                         note = /replace="aag"
variation                1231..1233
```

|  |  |  |
|---|---|---|
| variation | 1378..1380 | |
| | note = /replace="gag" | |
| variation | 1477..1479 | |
| | note = /replace="acc" | |
| variation | 1684..1686 | |
| | note = /replace="aac" | |
| variation | 1726..1728 | |
| | note = /replace="gag" | |
| variation | 1759..1761 | |
| | note = /replace="gcc" | |
| variation | 1825..1827 | |
| | note = /replace="gac" | |
| misc_feature | 1..2208 | |
| | note = /note="Variation nucleotides given in the sequence have no preference with respect to those in the annotations for variation positions" | |
| source | 1..2208 | |
| | mol_type = genomic DNA | |
| | organism = Adeno-associated virus | |

SEQUENCE: 2

```
atggctgccg atggttatct tccagattgg ctcgaggaca acctctctga gggcattcgc   60
gagtggtggg acttgaaacc tggagccccg aaacccaaag ccaaccagca aaagcaggac  120
gacgccggg gtctggtgct tcctggctac aagtacctcg acccctcaa cggactcgac   180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gcaatcaccc caggaaccag actcctcttc gggcatcggc  480
aagaaaggcc agcagcccgc gaagaagaga ctcaactttg ggcagacagg cgactcagag  540
tcagtgcccg accctcaacc actcggagaa ccccccgcag cccctctgg tgtgggatct  600
aatacaatgg cagcaggcgg tggcgctcca atggcagaca ataacgaagg cgccgacgga  660
gtgggtaacg cctcaggaaa ttggcattgc gattccacat ggctgggcga cagagtcatc  720
accaccagca cccgaacctg ggccctcccc acctacaaca accacctcta caagcaaatc  780
tccagccaat cgggagcaag caccaacgac aacacctact cggctacaga caccccctgg  840
gggtattttg actttaacag attccactgc cacttctcac cacgtgactg gcagcgactc  900
atcaacaaca ctggggatt ccggcccaag agactcaact tcaagctctt caacatccag  960
gtcaaggagg tcacgacgaa tgatggcacc acgacatcg ccaataacct taccagcacg 1020
gttcaggtct ttacggactc ggaataccag ctcccgtacg tcctcggctc tgcgcaccag 1080
ggctgcctgc ctccgttccc ggcggacgtc ttcatgattc tcagtacgg gtacctgact 1140
ctgaacaatg gcagtcaggc cgtgggccgt tcctccttct actgcctgga gtactttcct 1200
tctcaaatgc tgagaacggg caacaacttt gagttcagct acacgtttga ggacgtgcct 1260
tttcacagca gctacgcgca gccaaagc ctggaccggc tgatgaaccc cctcatcgac 1320
cagtacctgt actacctgtc tcggactcag accacgagtg gtaccgcagg aaatcggacg 1380
ttgcaatttt ctcaggccgg gcctagtagc atggcgaatc aggccaaaaa ctggctaccc 1440
gggccctgct accggcagca acgcgtctcc aagacagcga atcaaaataa caacagcaac 1500
tttgcctgga ccggtgccac caagtatcat ctgaatggca gagactctct ggtaaatccc 1560
ggtcccgcta tggcaaccca caggacgac gaagacaaat tttttccgat gagcggagtc 1620
ttaatatttg gaaacaggg agctggaaat agcaacgtgg accttgacaa cgttatgata 1680
accagtgagg aagaaattaa aaccaccaac ccagtggcca cagaacagta cggcacggtg 1740
gccactaacc tgcaatcgtc aaacaccgct cctgctacga gaccgtcaa cagtcaagga 1800
gccttacctg catggtctg gcagaaccgg gacgtgtacc tgcagggtcc tatctgggcc 1860
aagattcctc acacggacgg acactttcat ccctcgccgc tgatgggagg ctttggactg 1920
aaacaccccg ctcctcagat cctgattaag aatacacctg ttcccgcgaa tcctccaact 1980
accttcagtc cagctaagtt tgcgtcgttc atcacgcagt acagcaccgg acaggtcagc 2040
gtggaaattg aatgggagct gcagaaagaa aacagcaaac gctgaaccc agagattcaa 2100
tacacttcca actacaacaa atctacaat gtggactttg ctgttgacac aaatggcgtt 2160
tattctgagc ctcgccccat cggcacccgt tacctcaccc gtaatctg            2208
```

|  |  |
|---|---|
| SEQ ID NO: 3 | moltype = AA length = 737 |
| FEATURE | Location/Qualifiers |
| VARIANT | 157 |
| | note = /replace="Ser" |
| VARIANT | 168 |
| | note = /replace="Arg" |
| VARIANT | 262 |
| | note = /replace="Ser" |
| VARIANT | 263 |
| | note = /replace="His" |
| VARIANT | 312 |
| | note = /replace="Lys" |
| VARIANT | 412 |
| | note = /replace="Gln" |
| VARIANT | 460 |
| | note = /replace="Gln" |
| VARIANT | 461 |
| | note = /replace="Glu" |
| VARIANT | 552 |
| | note = /replace="Ser" |

| | | |
|---|---|---|
| VARIANT | 556 | |
| | note = /replace="Tyr" | |
| VARIANT | 557 | |
| | note = /replace="Ser" | |
| VARIANT | 563 | |
| | note = /replace="Asn" | |
| VARIANT | 580 | |
| | note = /replace="Ile" | |
| VARIANT | 588 | |
| | note = /replace="Ser" | |
| VARIANT | 664 | |
| | note = /replace="Thr" | |
| REGION | 1..737 | |
| | note = misc_feature - /note="Variant residues given in the sequence have no preference with respect to those in the annotations for variant positions" | |
| source | 1..737 | |
| | mol_type = protein | |
| | organism = Adeno-associated virus | |

SEQUENCE: 3

```
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSTGIG KKGQQPAKKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SNSQSGGSTN DNTYFGYSTP WGYFDFNRFH CHFSPRDWQR  300
LINNNWGFRP KRLNFKLFNI QVKEVTTNDG TTTIANNLTS TVQVFTDSEY QLPYVLGSAH  360
QGCLPPFPAD VFMIPQYGYL TLNNGSQAVG RSSFYCLEYF PSQMLRTGNN FEFSYTFEDV  420
PFHSSYAHSQ SLDRLMNPLI DQYLYYLSRT QTTGGTAGNR TLQFSQAGPS SMANQAKNWL  480
PGPCYRQQRV SKTTNQNNNS NFAWTGATKY HLNGRDSLVN PGVAMATHKD DEDRFFPSSG  540
VLIFGKQGAG NDNVDLDNVM ITSEEEIKTT NPVATEEYGV VATNLQSANT APQTGTVNSQ  600
GALPGMVWQN RDVYLQGPIW AKIPHTDGNF HPSPLMGGFG LKHPPPQILI KNTPVPANPP  660
TTFSPAKFAS FITQYSTGQV SVEIEWELQK ENSKRWNPEI QYTSNYNKST NVDFAVDTEG  720
VYSEPRPIGT RYLTRNL                                                737
```

| | | |
|---|---|---|
| SEQ ID NO: 4 | moltype = DNA   length = 2211 | |
| FEATURE | Location/Qualifiers | |
| variation | 469..471 | |
| | note = /replace="agc" | |
| variation | 502..504 | |
| | note = /replace="aag" | |
| variation | 784..786 | |
| | note = /replace="agt" | |
| variation | 787..789 | |
| | note = /replace="cac" | |
| variation | 934..936 | |
| | note = /replace="aag" | |
| variation | 1234..1236 | |
| | note = /replace="cag" | |
| variation | 1378..1380 | |
| | note = /replace="cag" | |
| variation | 1381..1383 | |
| | note = /replace="gag" | |
| variation | 1654..1656 | |
| | note = /replace="agc" | |
| variation | 1666..1668 | |
| | note = /replace="tac" | |
| variation | 1669..1671 | |
| | note = /replace="agc" | |
| variation | 1687..1689 | |
| | note = /replace="aac" | |
| variation | 1738..1740 | |
| | note = /replace="atc" | |
| variation | 1762..1764 | |
| | note = /replace="agc" | |
| variation | 1990..1992 | |
| | note = /replace="acc" | |
| misc_feature | 1..2211 | |
| | note = /note="Variation nucleotides given in the sequence have no preference with respect to those in the annotations for variation positions" | |
| source | 1..2211 | |
| | mol_type = genomic DNA | |
| | organism = Adeno-associated virus | |

SEQUENCE: 4

```
atggctgccg atggttatct tccagattgg ctcgaggaca acctctctga gggcattcgc   60
gagtggtggg acttgaaacc tggagccccg aaacccaaag ccaaccagca aaagcaggac  120
gacgccgggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
```

```
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gcaatcaccc caggaaccag actcctctac gggcatcggc    480
aagaaaggcc agcagcccgc gaaaagagga ctcaactttg gcagactggc gactcagag     540
tcagtgcccg accctcaacc actcggagaa ccccccgcag cccctctgg tgtgggatct     600
aatacaatgg ctgcaggcgg tggcgctcca atggcagaca ataacgaagg cgccgacgga    660
gtgggtaatg cctcaggaaa ttggcattgc gattccacat ggctgggcga cagagtcatc    720
accaccagca cccgaacctg ggccctcccc acctacaaca accacctcta caagcaaatc    780
tccaacagcc aatcgggagg aagcaccaac gacaacacct acttcggcta cagcacccc    840
tgggggtatt ttgactttaa cagattccac tgccacttct caccacgtga ctggcagcga    900
ctcatcaaca caactggggg attccggccc aagagactca acttcaagct cttcaacatc    960
caggtcaagg aggtcacgac gaatgatggc accacgacca tcgccaataa ccttaccagc   1020
acggttcagg tctttacgga ctcggaatac cagctcccgt acgtcctcgg ctctgcgcac   1080
cagggctgcc tgcctccgtt cccggcggac gtcttcatga ttcctcagta cggttacctg   1140
actctgaaca atggcagtca ggccgtgggc cgttcctcct tctactgcct ggagtacttt   1200
ccttctcaaa tgctgagaac gggcaacaac tttgagttca gctacacgtt tgaggacgtg   1260
ccttttcaca gcagctacgc gcacagccaa agcctggacc ggctgatgaa cccccctcatc  1320
gaccagtacc tgtactacct gtctcggact cagaccaccg gaggtaccgc aggaaatgca   1380
acgttgcaat tttctcaggc cgggcctagt agcatggcga atcaggccaa aaactggcta   1440
cccgggccct gctaccggca gcaacgcgtc tccaagacaa cgaatcaaaa taacaacagc   1500
aactttgcct ggaccggtgc caccaagtat catctgaatg gcagagactc tctggtaaat   1560
cccggtgtcg ctatgccaac ccacaaggac gacgaagacc gattttttcc gtccagcgga   1620
gtcttaatat ttgggaaaca gggagctgga aatgacaacc tggaccttgc caacgttatg   1680
ataaccagtg aggaagaaat taaaaccacc aacccagtgg ccacagaaga gtacggcgtg   1740
gtggccacta acctgcaatc ggcaaacacc gctcctcaaa cagggaccgt caacagtcaa   1800
ggagccttac ctggcatggt ctggcagaac cgggacgtgt acctgcaggg tcctatctga   1860
gccaagattc ctcacacgga cggaaacttt catccctcgc cgctgatggg aggctttgga   1920
ctgaaacacc cgcctcctca gatcctgatt aagaatacac ctgttcccgc gaatcctcca   1980
actaccttca gtccagctaa gtttgcgtcg ttcatcacgc agtacagcac cggacaggtc   2040
agcgtggaaa ttgaatggga gctgcagaaa gaaaacgctg aacgctggaa cccagagatt   2100
caatacactt ccaactacaa caaatctaca aatgtggact tgctcgttga cacagaaggc   2160
gtttattctg agcctcgccc catcggcacc cgttacctca cccgtaatct g           2211
```

```
SEQ ID NO: 5           moltype = AA  length = 738
FEATURE                Location/Qualifiers
VARIANT                158
                       note = /replace="Ser"
VARIANT                169
                       note = /replace="Arg"
VARIANT                564
                       note = /replace="Asn"
REGION                 1..738
                       note = misc_feature - /note="Variant residues given in the
                         sequence have no preference with respect to those in the
                         annotations for variant positions"
source                 1..738
                       mol_type = protein
                       organism = Adeno-associated virus
SEQUENCE: 5
MAADGYLPDW LEDNLSEGIR EWWDLKPGAP KPKANQQKQD DGRGLVLPGY KYLGPFNGLD     60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QREPDSSTGI GKKGQQPAKK RLNFGQTGDS   180
ESVPDPQPLG EPPAAPSGVG SNTMAAGGGA PMADNNEGAD GVGNSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTTNE GTKTIANNLT STVQVFTDSE YQLPYVLGSA   360
HQGCLPPFPA DVFMIPQYGY LTLNNGSQAV GRSSFYCLEY FPSQMLRTGN NFQFSYTFED   420
VPFHSSYAHS QSLDRLMNPL IDQYLYYLSR TQTTGGTAGT QTLQFSQAGP SSMANQAKNW   480
LPGPCYRQQR VSTTTQNNNS NFAWTGATK YHLNGRDSLV NPGVAMATHK DDEDRFFPSS    540
GVLIFGKQGA GNDNVDYSNV MITSEEEIKT TNPVATEEYG VVATNLQSAN TAPQTGTVNS   600
QGALPGMVWQ NRDVYLQGPI WAKIPHTDGN FHPSPLMGGF GLKHPPPQIL IKNTPVPADP   660
PTTFNQAKLN SFITQYSTGQ VSVEIEWELQ KENSKRWNPE IQYTSNYYKS TNVDFAVNTE   720
GVYSEPRPIG TRYLTRNL                                                 738
```

```
SEQ ID NO: 6           moltype = DNA  length = 2214
FEATURE                Location/Qualifiers
variation              472..474
                       note = /replace="agc"
variation              505..507
                       note = /replace="aga"
variation              1690..1692
                       note = /replace="aac"
misc_feature           1..2214
                       note = /note="Variation nucleotides given in the sequence
                         have no preference with respect to those in the
                         annotations for variation positions"
source                 1..2214
                       mol_type = genomic DNA
                       organism = Adeno-associated virus
SEQUENCE: 6
```

```
atggctgccg atggttatct tccagattgg ctcgaggaca acctctctga gggcattcgc    60
gagtggtggg acctgaaacc tggagccccg aaacccaaag ccaaccagca aaagcaggac   120
gacggccggg gtctggtgct tcctggctac aagtacctcg acccttcaa cggactcgac    180
aaggggggagc ccgtcaacgc ggcggacgca gcggccctcg agcacgacaa ggcctacgac   240
cagcagctca aagcgggtga caatccgtac ctgcggtata atcacgccga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaga gaccggtaga gcagtcacca cagcgtgagc ccgactcctc cacgggcatc   480
ggcaagaaag gccagcagcc cgccaaaaag agactcaatt tcggtcagac tggcgactca   540
gagtcagtcc ccgaccctca acctctcgga gaacctccag cagcgccctc tggtgtggga   600
tctaatacaa tggctgcagg cggtggcgca ccaatggcag acaataacga aggtgccgac   660
ggagtgggta attcctcggg aaattggcat tgcgattcca catggctggg cgacagagtc   720
atcaccacca gcacccgaac ctgggccctg cccacctaca acaaccacct ctacaagcaa   780
atctccaacg ggacctcggg aggcagcacc aacgacaacc cctactttgg ctacagcacc   840
ccctgggggt attttgactt taacagattc cactgccact ctcaccacg tgactggcag    900
cgactcatca caacaactg gggattccgg cccaagagac tcaacttcaa gctcttcaac   960
atccaggtca agaggtcac gacgaatgaa ggcaccaaga ccatcgccaa taacctcacc  1020
agcaccgtcc aggtgtttac ggactcggaa taccagctgc cgtacgtcct cggctctgcc  1080
caccagggct gcctgcctcc gttcccggca gacgtcttca tgattcctca gtacggctac  1140
ctgactctca caacaactag tcaggccgtg gacgttcct ccttctactg cctggagtac   1200
ttcccctctc agatgctgag aacgggcaac aactttcaat tcagctacac tttcgaggac  1260
gtgccttcc acagcagcta cgcgcacagc cagagtttga caggctgat gaatcctctc  1320
atcgaccagt acctgtacta cctgtcaaga acccagacta cgggaggcac agcgggaacc  1380
cagacgttgc agtttctca ggccgggcct agcagcatgg cgaatcaggc caaaaactgg  1440
ctgcctggac cctgctacag acagcagcgc gtctccacga caacgaatca aaacaacaac  1500
agcaactttg cctggactgg tgccaccaag tatcatctga acggcagaga ctctctggtg  1560
aatccgggcg tcgccatggc aacccacaag gacgacgagg accgcttctt cccatccagc  1620
ggcgtcctca tatttggcaa gcagggagct ggaaatgaca cgtggacta tagcaacgtg  1680
atgataacca gcgaggaaga aatcaagacc accaaccccg tggccacaga agagtatggc  1740
gtggtggcta ctaacctaca gtcggcaaac ccgctcctc aaacgggaca cgtcaacagc  1800
caggggagcct tacctggcat ggtctggcag aaccgggacg tgtacctgca gggtcctatt  1860
tgggccaaga ttcctcacac agatggcaac tttcacccgt ctcctttaat gggcggcttt  1920
ggacttaaac atccgcctcc tcagatcctc atcaaaaaca ctcctgttcc tgcggatcct  1980
ccaacaacgt tcaaccaggc caagctgaat tctttcatca cgcagtacag caccggacaa  2040
gtcagcgtgg agatcgagtg ggagctgcag aaggagaaca gcaagcgctg gaacccagag  2100
attcagtata cttccaacta ctacaaatct acaaatgtgg actttgctgt taatactgag  2160
ggtgtttact ctgagcctcg ccccattggc actcgttacc tcacccgtaa tctg         2214
```

SEQ ID NO: 7        moltype = AA   length = 738
FEATURE             Location/Qualifiers
VARIANT             158
                    note = /replace="Ser"
VARIANT             169
                    note = /replace="Lys"
VARIANT             315
                    note = /replace="Ser"
VARIANT             413
                    note = /replace="Glu"
VARIANT             472
                    note = /replace="Thr" or "Ser"
VARIANT             534
                    note = /replace="Glu"
VARIANT             542
                    note = /replace="Val"
VARIANT             595
                    note = /replace="Val"
REGION              1..738
                    note = misc_feature - /note="Variant residues given in the
                    sequence have no preference with respect to those in the
                    annotations for variant positions"
source              1..738
                    mol_type = protein
                    organism = Adeno-associated virus
SEQUENCE: 7
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QREPDSSTGI GKKGQQPARK RLNFGQTGDS   180
ESVPDPQPLG EPPAAPSGVG SNTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFSYTFED   420
VPFHSSYAHS QSLDRLMNPL IDQYLYYLSR TQTTGGTAGT QTLQFSQAGP SSMANQAKNW   480
LPGPCYRQQR VSTTTSQNNN SNFAWTGATK YHLNGRDSLV NPGVAMATHK DDEDRFFPSS   540
GILIFGKQGA GKDNVDYSNV MLTSEEEIKT TNPVATEEYG VVADNLQQQN TAPQIGTVNS   600
QGALPGMVWQ NRDVYLQGPI WAKIPHTDGN FHPSPLMGGF GLKHPPPQIL IKNTPVPADP   660
PTTFNQAKLN SFITQYSTGQ VSVEIEWELQ KENSKRWNPE IQYTSNYYKS TNVDFAVNTE   720
GVYSEPRPIG TRYLTRNL                                                 738

SEQ ID NO: 8        moltype = DNA   length = 2214

```
FEATURE              Location/Qualifiers
variation            472..474
                     note = /replace="agc"
variation            505..507
                     note = /replace="aag"
variation            943..945
                     note = /replace="agc"
variation            1237..1239
                     note = /replace="gaa"
variation            1414..1416
                     note = /replace="aac" or "agc"
variation            1600..1602
                     note = /replace="gag"
variation            1624..1626
                     note = /replace="gtc"
variation            1783..1785
                     note = /replace="gta"
misc_feature         1..2214
                     note = /note="Variation nucleotides given in the sequence
                      have no preference with respect to those in the
                      annotations for variation positions"
source               1..2214
                     mol_type = genomic DNA
                     organism = Adeno-associated virus
SEQUENCE: 8
atggctgccg atggttatct tccagattgg ctcgaggaca acctctctga gggcattcgc   60
gagtggtggg acctgaaacc tggagccccg aaacccaaag ccaaccagca aaagcaggac  120
gacgccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata atcacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gcagtcacca cagcgtgagc ccgactcctc cacgggcatc  480
ggcaagaaag gccagcagcc cgccagaaag agactcaatt tcggtcagac tggcgactca  540
gagtcagtcc ccgaccctca acctctcgga gaacctccag cgcgccctc tggtgtggga  600
tctaatacaa tggctgcagg cggtggcgca ccaatggcag acaataacga aggtgccgac  660
ggagtgggta gttcctcggg aaattggcat gcgattccac atggctgggc gacagagtc  720
atcaccacca gcacccgaac ctgggccctg cccacctaca caaccaccct ctacaagcaa  780
atctccaacg ggacctcggg aggcagcacc aacgacaacc cctactttgg ctacagcacc  840
ccctgggggt attttgactt taacagattc cactgccact tctcaccacg tgactggcag  900
cgactcatca caacaactg gggattccgg cccaagagac tcaacttcaa gctcttcaac  960
atccaggtca aagaggtcac gcagaatgaa ggcaccaaga ccatcgccaa taacctcacc 1020
agcaccatcc aggtgtttac ggactcggaa taccagctgc cgtacgtcct cggctctgcc 1080
caccagggct gcctgcctcc gttcccggcg gacgtcttca tgattcctca gtacggctac 1140
ctgactctca acaacggtag tcaggccgtg ggacgttcct cctttactg cctggagtac 1200
ttcccctctc agatgctgag aacgggcaac aactttcaat tcagctacac tttcgaggac 1260
gtgcctttcc acagcagcta cgcgcacagc cagagtttgg acaggctgat gaatcctctc 1320
atcgaccagt acctgtacta cctgtcaaga acccagacta cgggaggcac agcgggaacc 1380
cagacgttgc agtttctca ggccgggcct agcaacatgg cgaatcaggc caaaaactgg 1440
ctgcctggac cctgctacag acagcagcgc gtctccacga caacgtcgca aaacaacaac 1500
agcaactttg cctggactgg tgccaccaag tatcatctga acggcagaga ctctctgtg 1560
aatccgggcg tcgccatggc aacccacaag gacgacgagg accgcttctt cccatccagc 1620
ggcatcctca tatttggcaa gcagggagct ggaaaagaca cgtggactaa tagcaacgtg 1680
atgctaacca gcgaggaaga aatcaagacc accaaccccg tggccacaga agagtatggc 1740
gtggtggctg ataacctaca gcagcaaaac accgctcctc aaatagggac cgtcaacagc 1800
cagggagcct tacctggcat ggtctggcag aaccgggacg tgtacctgca gggtcctatt 1860
tgggccaaga ttcctcacac agatggcaac ttccaccgt tcccttaat gggcggcttt 1920
ggacttaaaac atccgcctcc tcagatcctc atcaaaaaca ctcctgttcc tgcgatcct 1980
ccaacaacgt tcaaccaggc caagctgaat tctttcatca cgcagtacag caccggacaa 2040
gtcagcgtgg agatcgagtg ggagctgcag aaggagaaca gcaagcgctg gaacccagag 2100
attcagtata cttccaacta ctacaaatct acaaatgtgg actttgctgt taatactgag 2160
ggtgtttact ctgagcctcg ccccattggc actcgttacc tcacccgtaa tctg       2214

SEQ ID NO: 9           moltype = AA  length = 738
FEATURE                Location/Qualifiers
VARIANT                169
                       note = /replace="Lys"
VARIANT                315
                       note = /replace="Ser"
VARIANT                534
                       note = /replace="Glu"
VARIANT                542
                       note = /replace="Val"
REGION                 1..738
                       note = misc_feature - /note="Variant residues given in the
                        sequence have no preference with respect to those in the
                        annotations for variant positions"
source                 1..738
                       mol_type = protein
```

```
                      organism = Adeno-associated virus
SEQUENCE: 9
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPIG EPPAAPSGVG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYTFED   420
VPFHSSYAHS QSLDRLMNPL IDQYLYYLSR TQSTGGTAGT QQLLFSQAGP SNMSAQAKNW   480
LPGPCYRQQR VSTTLSQNNN SNFAWTGATK YHLNGRDSLV NPGVAMATHK DDEDRFFPSS   540
GILMFGKQGA GKDNVDYSNV MLTSEEEIKT TNPVATEQYG VVADNLQQQN TAPIVGAVNS   600
QGALPGMVWQ NRDVYLQGPI WAKIPHTDGN FHPSPLMGGF GLKHPPPQIL IKNTPVPADP   660
PTTFNQAKLN SFITQYSTGQ VSVEIEWELQ KENSKRWNPE IQYTSNYYKS TNVDFAVNTE   720
GVYSEPRPIG TRYLTRNL                                                738

SEQ ID NO: 10          moltype = DNA  length = 2214
FEATURE                Location/Qualifiers
variation              505..507
                       note = /replace="aaa"
variation              943..945
                       note = /replace="agc"
variation              1600..1602
                       note = /replace="gag"
variation              1624..1626
                       note = /replace="gtc"
misc_feature           1..2214
                       note = /note="Variation nucleotides given in the sequence
                       have no preference with respect to those in the
                       annotations for variation positions"
source                 1..2214
                       mol_type = genomic DNA
                       organism = Adeno-associated virus
SEQUENCE: 10
atggctgccg atggttatct tccagattgg ctcgaggaca acctctctga gggcattcgc    60
gagtggtggg acctgaaacc tggagccccg aaacccaaag ccaaccagca aaagcaggac   120
gacggccggg gtctggtgct tcctggctac aagtacctcg gacccttcaa cggactcgac   180
aaggggagc ccgtcaacgc ggcggacgca gcggccctcg agcacgacaa ggcctacgac   240
cagctgaagg caggggtga caatccgtac ctgcggtata atcacgccga cgccgagttt   300
caggagcgtc tgcaagaaga tacgtctttt ggggggcaacc tcgggcgagc agtcttccag   360
gccaagaagc gggttctcga acctctcggt ctggttgagg aaggcgctaa gacggctcct   420
ggaaagaaga gaccggtaga gccgtcacca cagcgttccc ccgactcctc cacgggcatc   480
ggcaagaaag gccagcagcc cgccagaaag agactcaatt tcggtcagac tggcgactca   540
gagtcagtcc ccgaccctca acctatcgga gaacctccag cagcgccctc tggtgtggga   600
tctggtacaa tggctgcagg cggtggcgca ccaatggcag acaataacga aggtgccgac   660
ggagtgggta gttcctcggg aaattggcat tgcgattcca catggctggg cgacagagtc   720
atcaccacca gcacccgaac ctgggcccctg cccacctaca caaccaccct ctacaagcaa   780
atctccaacg gaacctcggg aggcagcacc aacgacaaca cctactttgg ctacagcacc   840
cctctggggggt attttgactt taacagattc cactgccact tctcaccacg tgactggcag   900
cgactcatca acaacaactg gggattccgg cccaagagac tcaacttcaa gctcttcaac   960
atccaggtca aagaggtcac gcagaatgaa ggcaccaaga ccatcgccaa taacctcacc  1020
agcaccatcc aggtgtttac ggactcggaa taccagctgc cgtacgtcct cggctctgcc  1080
caccagggct gcctgcctcc gttcccggcg gacgtcttca tgattcctca gtacggctac  1140
ctgactctca acaacggtag tcaggccgtg gacgttcct ccttctactg cctggagtac  1200
ttccccctctc agatgctgag aacgggcaac aactttgagt tcagctacac tttcgaggac  1260
gtgcctttcc acagcagcta cgcgcacagc cagagtttgg acaggctgat gaatcctctc  1320
atcgaccagt acctgtacta cctgtcaaga acccagtcta cggagggcac agcgggaacc  1380
cagcagttgc tgtttctca ggccgggcct agcaacatgt cggctcaggc caaaaactgg  1440
ctgcctggac cctgctacag acagcagcgc gtctccacga cactgtcgca aaacaacaac  1500
agcaactttg cctggactgg tgccaccaag tatcatctga acggcagaga ctctctggtg  1560
aatccgggcg tcgccatggc aacccacaag gacgacgagg accgcttctt cccatccagc  1620
ggcatcctca tgtttggcaa gcagggagct ggaaagaca cgtggacta tagcaacgtg  1680
atgctaacca gcgaggaaga aatcaagacc accaaccccg tggccacaga acagtatggc  1740
gtggtgctg ataacctaca gcagcaaaac accgctccta ttgtggggc cgtcaacgcc  1800
cagggagcct tacctggcat ggtctgcag aaccgggacg tgtacctgca gggtcctatt  1860
tgggccaaga ttcctcacac agatggcaac tttcacccgt ctcctttaat gggcggcttt  1920
ggacttaaaa atccgcctcc tcagatcctc atcaaaaaca ctcctgttcc tgcggatcct  1980
ccaacaacgt tcaaccaggc caagctgaat tctttcatca cgcagtacag caccggacaa  2040
gtcagcgtgg agatcgagtg ggagctgcag aaggcgctg caagcagaga gaacccagag  2100
attcagtata cttccaacta ctacaaatct acaaatgtgg actttgctgt taatactgag  2160
ggtgtttact ctgagcctcg ccccattggc actcgttacc tcacccgtaa tctg        2214

SEQ ID NO: 11          moltype = AA  length = 738
FEATURE                Location/Qualifiers
VARIANT                471
                       note = /replace="Asn"
REGION                 1..738
                       note = misc_feature - /note="Variant residues given in the
                       sequence have no preference with respect to those in the
```

```
                        annotations for variant positions"
source                  1..738
                        mol_type = protein
                        organism = Adeno-associated virus
SEQUENCE: 11
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYTFED  420
VPFHSSYAHS QSLDRLMNPL IDQYLYYLSR TQSTGGTAGT QQLLFSQAGP SNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN TAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTE  720
GTYSEPRPIG TRYLTRNL                                                738

SEQ ID NO: 12           moltype = DNA  length = 2214
FEATURE                 Location/Qualifiers
variation               1411..1413
                        note = /replace="aat"
misc_feature            1..2214
                        note = /note="Variation nucleotides given in the sequence
                         have no preference with respect to those in the
                         annotations for variation positions"
source                  1..2214
                        mol_type = genomic DNA
                        organism = Adeno-associated virus
SEQUENCE: 12
atggctgccg atggttatct tccagattgg ctcgaggaca acctctctga gggcattcgc   60
gagtggtggg acttgaaacc tggagccccg aaacccaaag ccaaccagca aaagcaggac  120
gacggccggg gtctggtgct tcctggctac aagtacctcg gacccttcaa cggactcgac  180
aaggggagc ccgtcaacgc ggcagacgca gcgctcgaac acgacaaagc ctactacgac  240
cagcagctca aagcgggtga caatccgtac ctgcggtata accacgccga cgccgagttt  300
caggagcgtc tgcaagaaga tacgtctttt ggggcaacc tcgggcgagc agtcttccag  360
gccaagaagc gggttctcga acctctcggt ctggttgagg aaggcgctaa gacggctcct  420
ggaaagaaga gaccggtaga gccatcaccc agcgttctc agactcctc tacgggcatc  480
ggcaagaaag gccagcagcc cgcgaaaaag agactcaact ttgggcagac tggcgactca  540
gagtcagtgc ccgaccctca accaatcgga gaaccccccg caggcccctc tggtctggga  600
tctggtacaa tggctgcagg cggtggcgct ccaatggcag acaataacga aggcgccgac  660
ggagtgggta gttcctcagg aaattggcat tgcgattcca catggctggg cgacagagtc  720
atcaccacca gcacccgaac ctgggccctc cccacctaca caaccacct ctacaagcaa  780
atctccaacg ggacttcggg aggaagcacc aacgacaaca cctacttcgg ctacagcacc  840
ccctgggggt attttgactt taacagattc cactgccact tctcaccacg tgactggcag  900
cgactcatca caacaactg gggattccgg cccaagagac tcaactttaa gctcttcaac  960
atccaggtca aggaggtcac gcagaatgaa ggcaccaaga ccatcgccaa taaccttacc 1020
agcacgattc aggtctttac ggactcggaa taccagctcc cgtacgtcct cggctctgcg 1080
caccagggct gcctgcctcc gttcccggcg gacgtcttca tgattcctca gtacgggtac 1140
ctgactctga acaatggcag tcaggccgtg ggcgttcct ccttctactg cctggagtac 1200
tttccttctc aaatgctgag aacgggcaac aactttgagt tcagctacac gtttgaggac 1260
gtgccttttc acagcagcta cgcgcacagc aaagcctgg accggctgat gaacccctc 1320
atcgaccagt acctgtacta cctgtctcgg actcagtcca cggaggtac cgcaggaact 1380
cagcagttgc tattttctca ggccgggcct agtaacatgt cggctcaggc caaaaactgg 1440
ctacccgggc cctgctaccg gcagcaacgc gtctccacga cactgtcgca aaataacaac 1500
agcaactttg cctggaccgg tgccaccaag tatcatctga atggcagaga ctctctggta 1560
aatcccggtg tcgctatggc aacccacaag gacgacgaag agcgatttt tccgtccagc 1620
ggagtcttaa tgtttgggaa acagggagct ggaaaagaca acgtggacta tagcagcgtt 1680
atgctaacca gtgaggaaga aattaaaacc accaacccag tggccacaga acagtacggt 1740
gtggtggccg ataacctgca acagcaaaac accgctccta ttgtaggggc cgtcaacagt 1800
caaggagcct tacctggcat ggtctggcag aaccgggacg tgtacctgca gggtcctatc 1860
tgggccaaga ttcctcacac ggacgaaac tttcatcct cgccgctgat gggaggcttt 1920
ggactgaaac acccgcctcc tcagatcctg attaagaata cacctgttcc cgcggatcct 1980
ccaactacct tcagtcaagc taagctggcg tcgttcatca cgcagtacag caccggacag 2040
gtcagcgtgg aaattgaatg ggagctgcag aaagaaaca gcaaacgctg aacccagag 2100
attcaataca cttccaacta ctacaaatct acaaatgtgg actttgctgt taacacagaa 2160
ggcacttatt ctgagcctcg ccccatcggc accgttacc tcacccgtaa tctg         2214

SEQ ID NO: 13           moltype = AA  length = 737
FEATURE                 Location/Qualifiers
VARIANT                 148
                        note = /replace="Gln"
VARIANT                 169
                        note = /replace="Arg"
VARIANT                 314
                        note = /replace="Asn"
VARIANT                 466
                        note = /replace="His"
```

```
VARIANT                  563
                         note = /replace="Ser"
VARIANT                  580
                         note = /replace="Ile"
VARIANT                  588
                         note = /replace="Ser"
REGION                   1..737
                         note = misc_feature - /note="Variant residues given in the
                           sequence have no preference with respect to those in the
                           annotations for variant positions"
source                   1..737
                         mol_type = protein
                         organism = Adeno-associated virus
SEQUENCE: 13
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEPSP QRSPDSSTGI GKKGQQPAKK RLNFGQTGDS   180
ESVPDPQPLG EPPAAPSGVG SGTMAAGGGA PMADNNEGAD GVGNASGNWH CDSTWLGDRV   240
ITTSTRTWAL PTYNNHLYKQ ISSQSAGSTN DNTYFGYSTP WGYFDFNRFH CHFSPRDWQR   300
LINNNWGFRP KKLRFKLFNI QVKEVTTNDG VTTIANNLTS TVQVFSDSEY QLPYVLGSAH   360
QGCLPPFPAD VFMIPQYGYL TLNNGSQSVG RSSFYCLEYF PSQMLRTGNN FEFSYTFEDV   420
PFHSSYAHSQ SLDRLMNPLI DQYLYYLART QSTTGGTAGN RELQFYQAGP STMAEQAKNW   480
LPGPCYRQQR VSKTLDQNNN SNFAWTGATK YHLNGRNSLV NPGVAMATHK DDEDRFFPSS   540
GVLIFGKTGA ANKTTLENVL MTNEEEIKTT NPVATEEYGV VSSNLQSANT APQTQTVNSQ   600
GALPGMVWQN RDVYLQGPIW AKIPHTDGNF HPSPLMGGFG LKHPPPQILI KNTPVPANPP   660
EVFTPAKFAS FITQYSTGQV SVEIEWELQK ENSKRWNPEI QYTSNYDKST NVDFAVDSEG   720
VYSEPRPIGT RYLTRNL                                                 737

SEQ ID NO: 14            moltype = DNA  length = 2211
FEATURE                  Location/Qualifiers
variation                442..444
                         note = /replace="cag"
variation                505..507
                         note = /replace="aga"
variation                940..942
                         note = /replace="aac"
variation                1396..1398
                         note = /replace="cac"
variation                1687..1689
                         note = /replace="agt"
variation                1738..1740
                         note = /replace="ata"
variation                1762..1764
                         note = /replace="tct"
misc_feature             1..2211
                         note = /note="Variation nucleotides given in the sequence
                           have no preference with respect to those in the
                           annotations for variation positions"
source                   1..2211
                         mol_type = genomic DNA
                         organism = Adeno-associated virus
SEQUENCE: 14
atggctgccg atggttatct tccagattgg ctcgaggaca acctctctga gggcattcgc    60
gagtggtggg acctgaaacc tggagccccg aaacccaaag ccaaccagca aaagcaggac   120
gacggccggg gtctggtgct tcctggctac aagtacctcg gacccttcaa cggactcgac   180
aaggggggagc ccgtcaacgc ggcggacgca gcggccctcg agcacgacaa ggcctacgac   240
cagcagctca aagcgggtga caatccgtac ctgcggtata ccacgccga cgccgagttt   300
caggagcgtc tgcaagaaga tacgtcattt ggggggcaacc tcgggcgagc agtcttccag   360
gccaagaagc gggttctcga accctctcgt ctggttgagg aaggcgctaa gacggctcct   420
ggaaagaaga gaccggtaga gccgtcacct cagcgttcc ccgactcctc cacgggcatc   480
ggcaagaaag gccagcagcc cgccaaaaag agactcaatt tcggtcagac tggcgactca   540
gagtcagtcc ccgaccctca acctctcgga gaacctccag cagcgccctc tggtgtggga   600
tctggtacaa tggctgcagg cggtggcgca ccaatggcag acaataacga aggtgccgac   660
ggagtgggta atgcctcagg aaattggcat tgcgattaca tgggctggg cagacagtc   720
attaccacca gcacccgaac ctgggccctg cccaccttaca acaaccacct ctacaagcaa   780
atctccagtc aaagtgcagg tagtaccaac gacaacacct acttcggcta cagcaccccc   840
tgggggtatt ttgactttaa cagattccac tgccacttct caccacgtga ctggcagcga   900
ctcatcaaca acaactgggg attccggccc aagaagctgc ggttcaagct cttcaacatc   960
caggtcaagg aggtcacgac gaatgacggc gttacgacca tcgctaataa ccttaccagc  1020
acggttcagg tatttcgga ctcggaatac cagctgccgt acgtcctcgg ctctgcgcac  1080
cagggctgcc tgcctccgtt cccggcggac gtcttcatga ttcctcagta cggctacctg  1140
actctcaaca atggcagtca gtctgtggga cgttcctcct tctactgcct ggagtacttc  1200
ccctctcaga tgctgagaac gggcaacaac tttgagttcg gctacacctt cgaggacgtg  1260
ccttccaca gcagctacgc acacagccag agcctggatc ggctgatgaa tccctcatc  1320
gaccagtact tgtactacct ggccagaaca cagagtacca aggaggcac agctggcaat  1380
cgggaactgc agttttacca ggccgggcct tcaactatgg ccgaacaagc caagaattgg  1440
ttacctggac cttgctaccg gcaacaaaga gtctccaaaa cgctggatca aaacaacaac  1500
agcaactttg cttggactgg tgccaccaaa tatcacctga cggcagaaa ctcgttggtt  1560
aatcccggcg tcgccatggc aactcacaag gacgacgagg accgcttttt cccatccagc  1620
```

```
ggagtcctga tttttggaaa aactggagca gctaacaaaa ctacattgga aaatgtgtta   1680
atgacaaatg aagaagaaat taaaactact aatcctgtag ccacggaaga atacggggta   1740
gtcagcagca acttacaatc ggctaatact gcaccccaga cacaaactgt caacagccag   1800
ggagccttac ctggcatggt ctggcagaac cgggacgtgt acctgcaggg tcccatctgg   1860
gccaagattc ctcacacgga tggcaacttt caccgcctc ctttgatggg cggcttttga   1920
cttaaacatc cgcctcctca gatcctgatc aagaacactc ccgttccgc taatcctccg   1980
gaggtgttta ctcctgccaa gtttgcttcg ttcatcacac agtacagcac cggacaagtc   2040
agcgtggaaa tcgagtggga gctgcagaag gaaaacagca gcgctggaa cccggagatt   2100
cagtacacct ccaactatga taagtcgact aatgtggact ttgccgttga cagcgagggt   2160
gtttactctg agcctcgccc tattggcact cgttacctca cccgtaatct g            2211
```

| SEQ ID NO: 15 | moltype = AA  length = 735 |
|---|---|
| FEATURE | Location/Qualifiers |
| VARIANT | 162 |
| | note = /replace="Thr" |
| VARIANT | 168 |
| | note = /replace="Arg" |
| VARIANT | 224 |
| | note = /replace="Ser" |
| VARIANT | 310 |
| | note = /replace="Lys" |
| VARIANT | 410 |
| | note = /replace="Gln" |
| VARIANT | 446 |
| | note = /replace="Asn" |
| VARIANT | 461 |
| | note = /replace="Leu" |
| VARIANT | 471 |
| | note = /replace="Ser" |
| VARIANT | 708 |
| | note = /replace="Thr" |
| REGION | 1..735 |
| | note = misc_feature - /note="Variant residues given in the sequence have no preference with respect to those in the annotations for variant positions" |
| source | 1..735 |
| | mol_type = protein |
| | organism = Adeno-associated virus |

```
SEQUENCE: 15
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KSGQQPAKKR LNFGQTGDSE   180
SVPDPQPLGE PPAAPSGVGS NTMASGGGAP MADNNEGADG VGNASGNWHC DSTWLGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTTNDGTT TIANNLTSTV QVFTDSEYQL PYVLGSAHQG   360
CLPPFPADVF MIPQYGYLTL NNGSQAVGRS SFYCLEYFPS QMLRTGNNFT FSYTFEDVPF   420
HSSYAHSQSL DRLMNPLIDQ YLYYLSRTQT TSGTAQNREL QFSQAGPSSM ANQAKNWLPG   480
PCYRQQRVSK TANDNNNSNF AWTGATKYHL NGRDSLVNPG PAMASHKDDE DKFFPMSGVL   540
IFGKQGAGAS NVDLDNVMIT DEEEIKTTNP VATEQYGTVA TNLQSSNTAP ATGTVNSQGA   600
LPGMVWQDRD VYLQGPIWAK IPHTDGHFHP SPLMGGFGLK HPPPQILIKN TPVPANPPTT   660
FSPAKFASFI TQYSTGQVSV EIEWELQKEN SKRWNPEIQY TSNYNKSANV DFTVDTNGVY   720
SEPRPIGTRY LTRNL                                                   735
```

| SEQ ID NO: 16 | moltype = DNA  length = 2205 |
|---|---|
| FEATURE | Location/Qualifiers |
| variation | 484..486 |
| | note = /replace="aca" |
| variation | 502..504 |
| | note = /replace="aga" |
| variation | 670..672 |
| | note = /replace="tcc" |
| variation | 928..930 |
| | note = /replace="aaa" |
| variation | 1228..1230 |
| | note = /replace="cag" |
| variation | 1336..1338 |
| | note = /replace="aac" |
| variation | 1381..1383 |
| | note = /replace="ctg" |
| variation | 1411..1413 |
| | note = /replace="tct" |
| variation | 2122..2124 |
| | note = /replace="acc" |
| misc_feature | 1..2205 |
| | note = /note="Variation nucleotides given in the sequence have no preference with respect to those in the annotations for variation positions" |
| source | 1..2205 |
| | mol_type = genomic DNA |

-continued

```
                        organism = Adeno-associated virus
SEQUENCE: 16
atggctgccg atggttatct tccagattgg ctcgaggaca acctctctga gggcattcgc    60
gagtggtggg acttgaaacc tggagccccg aaacccaaag ccaaccagca aaagcaggac   120
gacggccggg gtctggtgct tcctggctac aagtacctcg gacccttcaa cggactcgac   180
aaggggagc ccgtcaacgc ggcggatgca gcggccctcg agcacgacaa ggcctacgac   240
cagcagctca aagcgggtga caatccgtac ctgcggtata accacgccga cgccgagttt   300
caggagcgtc tgcaagaaga tacgtctttt gggggcaacc tcgggcgagc agtcttccag   360
gccaagaaga gggttctcga acctcttggt ctggttgagg aaggtgctaa gacggctcct   420
ggaaagaaac gtccggtaga gcagtcgcca caagagccag actcctcctc gggcattgge   480
aagtcaggcc agcagcccgc taaaaagaga ctcaattttg gtcagactgg cgactcagag   540
tcagtccccg acccacaacc tctcggagaa cctccagcag ccccctctgg tgtgggatct   600
aatacaatgg cttcaggcgg tggcgcacca atggcagaca taacgaagg cgccgacgga   660
gtgggtaatg cctcaggaaa ttggcattgc gattccacat ggctgggcga cagagtcatc   720
accaccagca cccgaacatg ggccttgccc acctataaca accacctcta caagcaaatc   780
tccagtcaat caggggccag caacgacaac cactacttcg gctacagcac cccctgggga   840
tattttgatt tcaacagatt ccactgccat ttctcaccac gtgactggca gcgactcatc   900
aacaacaatt gggattccg gcccaagaga ctcaacttca agtcttcaa catccaagtc   960
aaggaggtca cgacgaatga tggcaccacg accatcgcta ataaccttac cagcacggtt  1020
caagtcttca cggactcgga gtaccagttg ccgtacgtcc tcggctctgc gcaccagggc  1080
tgcctccctc cgttcccggc ggacgtgttc atgattccgc agtacggcta cctaacgctc  1140
aacaatggca gccaggcagt gggacggtca tccttcctac gcctggaata tttcccatcg  1200
cagatgctga aacgggcaa taactttacc ttcagctaca ccttcgagga cgtgcctttc  1260
cacagcagct acgcgcacag ccagagcctg gaccggctga tgaatcctct catcgaccag  1320
tacctgtatt acctgagcag aactcagact acgtccggaa ctgcccaaaa cagggagttg  1380
cagtttagcc aggcgggtcc atctagcatg gctaatcagg ccaaaaactg gctacctgga  1440
ccctgttacc ggcagcagcg cgtttctaaa acagcaaatg acaacaacaa cagcaacttt  1500
gcctggactg gtgctacaaa atatcacctt aatgggcgtg attctttagt caaccctggc  1560
cctgctatgg cctcacacaa agacgacgaa gacaagttct ttcccatgag cggtgtcttg  1620
attttttggaa agcagggcgc cggagcttca aacgttgatt gcaatgtcat gatcaca    1680
gacgaagagg aaatcaaaac cactaacccc gtggccaccg aacaatatgg gactgtggca  1740
accaatctcc agagcagcaa cacagcccct gcgaccggaa ctgtgaattc tcagggagcc  1800
ttacctggaa tggtgtggca agacagagac gtatacctgc agggtcctat ttgggccaaa  1860
attcctcaca cggatggaca cttttcaccg tctcctctca tgggcggctt tggacttaag  1920
caccccgcctc ctcagatcct catcaaaaac acgcctgttc ctgcgaatcc tccgacaacg  1980
ttttcgcctg caaagtttgc ttcattcatc acccagtatt ccacaggaca agtgagcgtg  2040
gagattgaat gggagctgca gaagaaaac agcaaacgct ggaatccga aatacagtat  2100
acatctaact ataataaatc tgccaacgtt gatttcactg tggacaccaa tggagtttat  2160
agtgagcctg ccccattgg cacccgttac ctcacccgta acctg                   2205

SEQ ID NO: 17           moltype = AA  length = 735
FEATURE                 Location/Qualifiers
VARIANT                 42
                        note = /replace="Ser"
VARIANT                 168
                        note = /replace="Lys"
VARIANT                 310
                        note = /replace="Arg"
VARIANT                 410
                        note = /replace="Gln"
VARIANT                 446
                        note = /replace="Arg"
VARIANT                 461
                        note = /replace="Leu"
VARIANT                 471
                        note = /replace="Ser"
VARIANT                 475
                        note = /replace="Arg"
VARIANT                 504
                        note = /replace="Ala"
VARIANT                 539
                        note = /replace="Asn"
REGION                  1..735
                        note = misc_feature - /note="Variant residues given in the
                          sequence have no preference with respect to those in the
                          annotations for variant positions"
source                  1..735
                        mol_type = protein
                        organism = Adeno-associated virus
SEQUENCE: 17
MAADGYLPDW LEDNLSEGIR EWWDLKPGAP QPKANQQHQD DGRGLVLPGY KYLGPFNGLD    60
KGEPVNEADA AALEHDKAYD QQLKAGDNPY LKYNHADAEF QERLQEDTSF GGNLGRAVFQ   120
AKKRVLEPLG LVEEAAKTAP GKKRPVEQSP QEPDSSSGIG KSGQQPARKR LNFGQTGDSE   180
SVPDPQPLGE PPAAPSGVGS NTMASGGGAP MADNNEGADG VGNSSGNWHC DSTWLGDRVI   240
TTSTRTWALP TYNNHLYKQI SSQSGASNDN HYFGYSTPWG YFDFNRFHCH FSPRDWQRLI   300
NNNWGFRPKK LNFKLFNIQV KEVTQNDGTT TIANNLTSTV QVFTDSEYQL PYVLGSAHQG   360
CLPPFPADVF MIPQYGYLTL NNGSQAVGRS SFYCLEYFPS QMLRTGNNFT FSYTFEDVPF   420
HSSYAHSQSL DRLMNPLIDQ YLYYLSRTQT TSGTTQQSRL QFSQAGPSSM AQQAKNWLPG   480
PCYRQQRVSK TANDNNNSNF AWTGATKYHL NGRDSLVNPG PAMASHKDDE EKFFPMHGVL   540
```

```
                                            -continued
IFGKQGTGAS NVDLDNVMIT DEEEIRTTNP VATEQYGTVA TNLQSSNTAP ATGTVNSQGA   600
LPGMVWQDRD VYLQGPIWAK IPHTDGHFHP SPLMGGFGLK HPPPQILIKN TPVPANPPTT   660
FSPAKFASFI TQYSTGQVSV EIEWELQKEN SKRWNPEIQY TSNYNKSVNV DFTVDTNGVY   720
SEPRPIGTRY LTRNL                                                   735

SEQ ID NO: 18            moltype = DNA   length = 2205
FEATURE                  Location/Qualifiers
variation                124..126
                         note = /replace="agt"
variation                502..504
                         note = /replace="aaa"
variation                928..930
                         note = /replace="aga"
variation                1228..1230
                         note = /replace="cag"
variation                1336..1338
                         note = /replace="aga"
variation                1381..1383
                         note = /replace="ctc"
variation                1411..1413
                         note = /replace="tct"
variation                1423..1425
                         note = /replace="aga"
variation                1510..1512
                         note = /replace="gcg"
variation                1615..1617
                         note = /replace="gac"
misc_feature             1..2205
                         note = /note="Variation nucleotides given in the sequence
                          have no preference with respect to those in the
                          annotations for variation positions"
source                   1..2205
                         mol_type = genomic DNA
                         organism = Adeno-associated virus
SEQUENCE: 18
atggctgctg acggttatct tccagattgg ctcgaggaca acctttctga aggcattcgt    60
gagtggtggg atctgaaacc tggagcccct caacccaaag cgaaccaaca acaccaggac   120
gacggtcggg gtcttgtgct tccggggtac aaataccctc gacccttaa cggactcgac    180
aaaggagagc cggtcaacga ggcggacgcg gcagccctcg aacacgacaa agcttacgac   240
cagcagctca aggccggtga caaccccgta ctcaagtaca ccacgccga cgccgagttt    300
caggagcgtc ttcaagaaga tacgtctttt ggggggcaacc ttggcagagc agtcttccag   360
gccaaaaaga gggtccttga gcctcttggt ctggttgagaa agcagctaa aacggctcct   420
ggaaagaaga ggcctgtaga acagtctcct caggaaccgg actcatcatc tggtattggc   480
aaatcgggcc aacagcctgc cagaaaaaga ctaaatttcg gtcagactgg agactcagag   540
tcagtcccag accctcaacc tctcggagaa ccaccagcag cccccctcagg tgtgggatct   600
aatacaatgg cttcaggcgg tggcgcacca atggcagaca taacgagggg tgccgatgga   660
gtgggtaatt cctcaggaaa ttggcattgc gattccacat ggctgggcga cagagtcatc   720
accaccagca ccagaaccctg ggccctgccc acttacaaca accatctcta caagcaaatc   780
tccagccaat caggagcttc aaacgacaac cactactttg gctacagcac ccttggggga   840
tatttgact ttaacagatt ccactgccac ttctcaccac gtgactggca gcgactcatt   900
aacaacaact gggattccg gcccaagaaa ctcaacttca agtcttcaa catccaagtt   960
aaagaggtca cgcagaacga tggcacgacg actattgcca ataaccttac agcacggtt   1020
caagtgttta cggactcgga gtatcagctc ccgtacgtgc tcgggtcggc gcaccaaggc   1080
tgtctccccgc cgtttccagc ggacgtcttc atgatccctc agtatggata cctcaccctg   1140
aacaacggaa gtcaagcggt gggacgctca tcctttact gcctggagta cttccccttcg   1200
cagatgctaa ggactggaaa taacttcaca ttcagctata ccttcgagga tgtacctttt   1260
cacagcagct acgctcacag ccagagtttg gatcgcttga tgaatcctct tattgatcag   1320
tatctgtact acctgagcag aacgcaaaca acctctggaa caacccaaca atcacggctg   1380
caatttagcc aggctgggcc ttcgtctatg gctcagcagg ccaaaaattg gctacctggg   1440
ccctgctacc ggcaacagag agtttcaaag actgctaacg acaacaacaa cagtaacttt   1500
gcttggacag gggccaccaa atatcatctc aatggccgcg actcgctggt gaatccagga   1560
ccagctatgg ccagtcacaa ggacgatgaa gaaaaatttt tccctatgca cggcgttcta   1620
atatttggca acaagggac aggggcaagt aacgtagatt tagataatgt aatgattacg   1680
gatgaagaag agattcgtac caccaatccc gtggcacaag aaccatatgga aactgtggca   1740
actaacttgc agagctcaaa tacagctccc gcgactggaa ctgtcaatag tcagggggcc   1800
ttacctggca tggtgtggca agatcgtgac gtgtaccttc aaggacctat ctgggcaaag   1860
attcctcaca cggatggaca cttttcatcct tctcctctga tgggaggctt tggactgaaa   1920
catccgcctc ctcaaatctt gatcaaaaat actccggtac cggcaaatcc tccgacgact   1980
ttcagcccgg ccaagtttgc ttcatttatc actcagtact ccactggaca gtcagcgtg   2040
gaaattgagt gggagctaca gaaagaaaac agcaaacgtt ggaatccaga gattcagtac   2100
acttccaact acaacaagtc tgttaatgtg gactttactg tagacactaa tggtgtttat   2160
agtgaacctc gccctattgg aacccggtat ctcacacgaa acttg             2205

SEQ ID NO: 19            moltype = AA   length = 736
FEATURE                  Location/Qualifiers
source                   1..736
                         mol_type = protein
                         organism = Adeno-associated virus
SEQUENCE: 19
```

```
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPARKR LNFGQTGDSE   180
SVPDPQPLGE PPAAPSGVGS NTMAAGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK RLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRT LQFSQAGPSS MANQAKNWLP   480
GPCYRQQRVS KTANQNNNSN FAWTGATKYH LNGRDSLVNP GPAMATHKDD EDKFFPMSGV   540
LIFGKQGAGN SNVDLDNVMI TNEEEIKTTN PVATEQYGTV ATNLQSANTA PATGTVNSQG   600
ALPGMVWQDR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                   736

SEQ ID NO: 20          moltype = AA  length = 736
FEATURE                Location/Qualifiers
source                 1..736
                       mol_type = protein
                       organism = Adeno-associated virus
SEQUENCE: 20
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPAKKR LNFGQTGDSE   180
SVPDPQPLGE PPAAPSGVGS NTMASGGGAP MADNNEGADG VGNASGNWHC DSTWLGDRVI   240
TTSTRTWALP TYNNHLYKQI SSQSGASTND NTYFGYSTPW GYFDFNRFHC HFSPRDWQRL   300
INNNWGFRPK RLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF QFSYTFEDVP   420
FHSSYAHSQS LDRLMNPLID QYLYYLSRTQ TTSGTAGNRE LQFSQAGPSS MANQAKNWLP   480
GPCYRQQRVS KTTNQNNNSN FAWTGATKYH LNGRDSLVNP GPAMATHKDD EDKFFPMSGV   540
LIFGKQGAGN SNVDLDNVMI TNEEEIKTTN PVATEEYGTV ATNLQSANTA PATGTVNSQG   600
ALPGMVWQNR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                   736

SEQ ID NO: 21          moltype = AA  length = 736
FEATURE                Location/Qualifiers
source                 1..736
                       mol_type = protein
                       organism = Adeno-associated virus
SEQUENCE: 21
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPARKR LNFGQTGDSE   180
SVPDPQPLGE PPAAPSGVGS NTMAAGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK RLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRE LQFSQAGPSS MANQAKNWLP   480
GPCYRQQRVS KTTNQNNNSN FAWTGATKYH LNGRDSLVNP GPAMATHKDD EDKFFPMSGV   540
LIFGKQGAGN SNVDLDNVMI TSEEEIKTTN PVATEEYGTV ATNLQSSNTA PATGTVNSQG   600
ALPGMVWQER DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                   736

SEQ ID NO: 22          moltype = AA  length = 736
FEATURE                Location/Qualifiers
source                 1..736
                       mol_type = protein
                       organism = Adeno-associated virus
SEQUENCE: 22
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPARKR LNFGQTGDSE   180
SVPDPQPLGE PPAAPSGVGS NTMASGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK KLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRE LQFSQAGPSS MANQAKNWLP   480
GPCYRQQRVS KTTNQNNNSN FAWTGATKYH LNGRDSLVNP GPAMATHKDD EDKFFPMSGV   540
LIFGKQGAGN SNVDLDNVMI TSEEEIKTTN PVATEEYGTV ATNLQSANTA PATGTVNSQG   600
ALPGMVWQDR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                   736

SEQ ID NO: 23          moltype = AA  length = 736
FEATURE                Location/Qualifiers
source                 1..736
                       mol_type = protein
                       organism = Adeno-associated virus
```

```
SEQUENCE: 23
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPARKR LNFGQTGDSE   180
SVPDPQPLGE PPAAPSGVGS NTMAAGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK KLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF QFSYTFEDVP   420
FHSSYAHSQS LDRLMNPLID QYLYYLSRTQ TTSGTAGNRT LQFSQAGPSS MANQAKNWLP   480
GPCYRQQRVS KTTNQNNNSN FAWTGATKYH LNGRDSLVNP GPAMATHKDD EDKFFPMSGV   540
LIFGKQGAGN SNVDLDNVMI TNEEEIKTTN PVATEEYGTV ATNLQSANTA PATGTVNSQG   600
ALPGMVWQDR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                  736

SEQ ID NO: 24            moltype = AA   length = 736
FEATURE                  Location/Qualifiers
source                   1..736
                         mol_type = protein
                         organism = Adeno-associated virus
SEQUENCE: 24
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPAKKR LNFGQTGDSE   180
SVPDPQPLGE PPAAPSGVGS NTMAAGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK KLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRT LQFSQAGPSS MANQAKNWLP   480
GPCYRQQRVS KTANQNNNSN FAWTGATKYH LNGRDSLVNP GPAMATHKDD EDKFFPMSGV   540
LIFGKQGAGN SNVDLDNVMI TSEEEIKTTN PVATEQYGTV ATNLQSSNTA PATGTVNSQG   600
ALPGMVWQNR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                  736

SEQ ID NO: 25            moltype = AA   length = 736
FEATURE                  Location/Qualifiers
source                   1..736
                         mol_type = protein
                         organism = Adeno-associated virus
SEQUENCE: 25
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPAKKR LNFGQTGDSE   180
SVPDPQPLGE PPAAPSGVGS NTMASGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK KLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRT LQFSQAGPSS MANQAKNWLP   480
GPCYRQQRVS KTANQNNNSN FAWTGATKYH LNGRDSLVNP GPAMATHKDD EDKFFPMSGV   540
LIFGKQGAGN SNVDLDNVMI TSEEEIKTTN PVATEEYGTV ATNLQSSNTA PATGTVNSQG   600
ALPGMVWQNR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                  736

SEQ ID NO: 26            moltype = AA   length = 736
FEATURE                  Location/Qualifiers
source                   1..736
                         mol_type = protein
                         organism = Adeno-associated virus
SEQUENCE: 26
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KKGQQPAKKR LNFGQTGDSE   180
SVPDPQPLGE PPAAPSGVGS NTMASGGGAP MADNNEGADG VGNASGNWHC DSTWLGDRVI   240
TTSTRTWALP TYNNHLYKQI SSQSGGSTND NTYFGYSTPW GYFDFNRFHC HFSPRDWQRL   300
INNNWGFRPK KLNFKLFNIQ VKEVTTNDGT TTIANNLTST VQVFTDSEYQ LPYVLGSAHQ   360
GCLPPFPADV FMIPQYGYLT LNNGSQAVGR SSFYCLEYFP SQMLRTGNNF EFSYTFEDVP   420
FHSSYAHSQS LDRLMNPLID QYLYYLSRTQ TTSGTAGNRE LQFSQAGPSS MANQAKNWLP   480
GPCYRQQRVS KTTNQNNNSN FAWTGATKYH LNGRDSLVNP GPAMATHKDD EDKFFPMSGV   540
LIFGKQGAGN SNVDLDNVMI TNEEEIKTTN PVATEQYGTV ATNLQSANTA PATGTVNSQG   600
ALPGMVWQDR DVYLQGPIWA KIPHTDGHFH PSPLMGGFGL KHPPPQILIK NTPVPANPPT   660
TFSPAKFASF ITQYSTGQVS VEIEWELQKE NSKRWNPEIQ YTSNYNKSTN VDFAVDTNGV   720
YSEPRPIGTR YLTRNL                                                  736

SEQ ID NO: 27            moltype = AA   length = 738
FEATURE                  Location/Qualifiers
source                   1..738
                         mol_type = protein
```

```
                    organism = Adeno-associated virus
SEQUENCE: 27
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 28           moltype = AA   length = 736
FEATURE                 Location/Qualifiers
source                  1..736
                        mol_type = protein
                        organism = Adeno-associated virus
SEQUENCE: 28
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PPFHSSYAHSQ SLDRLMNPLI DQYLYYLSKT INGSGQNQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 29           moltype = AA   length = 736
FEATURE                 Location/Qualifiers
source                  1..736
                        mol_type = protein
                        organism = Adeno-associated virus
SEQUENCE: 29
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPFG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD KDKFFPMSGV   540
MIFGKESAGA SNTALDNVMI TDEEEIKATN PVATERFGTV AVNLQSSSTD PATGDVHVMG   600
ALPGMVWQDR DVYLQGPIWA KIPHTDGHFH PSPLMGGFGL KHPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                   736

SEQ ID NO: 30           moltype = AA   length = 736
FEATURE                 Location/Qualifiers
source                  1..736
                        mol_type = protein
                        organism = Adeno-associated virus
SEQUENCE: 30
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEEVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD EDKFFPMSGV   540
MIFGKESAGA SNTALDNVMI TDEEEIKATN PVATERFGTV AVNFQSSSTD PATGDVHAMG   600
ALPGMVWQDR DVYLQGPIWA KIPHTDGHFH PSPLMGGFGL KNPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                   736

SEQ ID NO: 31           moltype = AA   length = 735
FEATURE                 Location/Qualifiers
source                  1..735
```

```
                        mol_type = protein
                        organism = Adeno-associated virus
SEQUENCE: 31
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNRQA ATADVNTQGV   600
LPGMVWQDRD VYLQGPIWAK IPHTDGHFHP SPLMGGFGLK HPPPQILIKN TPVPANPSTT   660
FSAAKFASFI TQYSTGQVSV EIEWELQKEN SKRWNPEIQY TSNYNKSVNV DFTVDTNGVY   720
SEPRPIGTRY LTRNL                                                   735

SEQ ID NO: 32           moltype = AA  length = 736
FEATURE                 Location/Qualifiers
source                  1..736
                        mol_type = protein
                        organism = Adeno-associated virus
SEQUENCE: 32
MAADGYLPDW LEDNLSEGIR EWWALKPGVP QPKANQQHQD NRRGLVLPGY KYLGPGNGLD    60
KGEPVNEADA AALEHDKAYD QQLKAGDNPY LKYNHADAEF QERLQEDTSF GGNLGRAVFQ   120
AKKRILEPLG LVEEAAKTAP GKKGAVDQSP QEPDSSSGVG KSGKQPARKR LNFGQTGDSE   180
SVPDPQPLGE PPAAPTSLGS NTMASGGGAP MADNNEGADG VGNSSGNWHC DSQWLGDRVI   240
TTSTRTWALP TYNNHLYKQI SSQSGASNDN HYFGYSTPWG YFDFNRFHCH FSPRDWQRLI   300
NNNWGFRPKK LSFKLFNIQV RGVTQNDGTT TIANNLTSTV QVFTDSEYQL PYVLGSAHQG   360
CLPPFPADVF MVPQYGYLTL NNGSQAVGRS SFYCLEYFPS QMLRTGNNFQ FSYTFEDVPF   420
HSSYAHSQSL DRLMNPLIDQ YLYYLNRTQG TTSGTTNQSR LLFSQAGPQS MSLQARNWLP   480
GPCYRQQRLS KTANDNNSN FPWTAASKYH LNGRDSLVNP GPAMASHKDD EEKFFPMHGN   540
LIFGKEGTTA SNAELDNVMI TDEEEIRTTN PVATEQYGTV ANNLQSSNTA PTTGTVNHQG   600
ALPGMVWQDR DVYLQGPIWA KIPHTDGHFH PSPLMGGFGL KHPPPQIMIK NTPVPANPPT   660
TFSPAKFASF ITQYSTGQVS VEIEWELQKE NSKRWNPEIQ YTSNYNKSVN VDFTVDTNGV   720
YSEPRPIGTR YLTRNL                                                  736

SEQ ID NO: 33           moltype = AA  length = 736
FEATURE                 Location/Qualifiers
source                  1..736
                        mol_type = protein
                        organism = Adeno-associated virus
SEQUENCE: 33
MAADGYLPDW LEDNLSEGIR EWWALKPGVP QPKANQQHQD NRRGLVLPGY KYLGPGNGLD    60
KGEPVNEADA AALEHDKAYD QQLKAGDNPY LKYNHADAEF QERLQEDTSF GGNLGRAVFQ   120
AKKRILEPLG LVEEAAKTAP GKKRPVDQSP QEPDSSSGVG KSGKQPARKR LNFGQTGDSE   180
SVPDPQPLGE PPAAPTSLGS NTMASGGGAP MADNNEGADG VGNSSGNWHC DSQWLGDRVI   240
TTSTRTWALP TYNNHLYKQI SSQSGASNDN HYFGYSTPWG YFDFNRFHCH FSPRDWQRLI   300
NNNWGFRPKK LSFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFQ FSYTFEDVPF   420
HSSYAHSQSL DRLMNPLIDQ YLYYLNRTQG TTSGTTNQSR LLFSQAGPQS MSLQARNWLP   480
GPCYRQQRLS KTANDNNSN FPWTAASKYH LNGRDSLVNP GPAMASHKDD EEKFFPMHGN   540
LIFGKEGTTA SNAELDNVMI TDEEEIRTTN PVATEQYGTV ANNLQSSNTA PTTRTVNDQG   600
ALPGMVWQDR DVYLQGPIWA KIPHTDGHFH PSPLMGGFGL KHPPPQIMIK NTPVPANPPT   660
TFSPAKFASF ITQYSTGQVS VEIEWELQKE NSKRWNPEIQ YTSNYNKSVN VDFTVDTNGV   720
YSEPRPIGTR YLTRNL                                                  736

SEQ ID NO: 34           moltype = AA  length = 737
FEATURE                 Location/Qualifiers
source                  1..737
                        mol_type = protein
                        organism = Adeno-associated virus
SEQUENCE: 34
MAADGYLPDW LEDNLSEGIR EWWDLKPGAP KPKANQQKQD NGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP AKKRPVEPSP QRSPDSSTGI GKKGQQPARK RLNFGQTGDS   180
ESVPDPQPLG EPPAAPSSVG SGTVAAGGGA PMADNNEGAD GVGNASGNWH CDSTWLGDRV   240
ITTSTRTWAL PTYNNHLYKQ ISSETAGSTN DNTYFGYSTP WGYFDFNRFH CHFSPRDWQR   300
LINNWGFRP KKLRFKLFNI QVKEVTTNDG VTTIANNLTS TIQVFSDSEY QLPYVLGSAH   360
QGCLPPFPAD VFMIPQYGYL TLNNGSQSVG RSSFYCLEYF PSQMLRTGNN FEFSYSFEDV   420
PFHSSYAHSQ SLDRLMNPLI DQYLYYLART QSNPGGTAGN RELQFYQGGP STMAEQAKNW   480
LPGPCFRQQR VSKTLDQNNN SNFAWTGATK YHLNGRNSLV NPGVAMATHK DDEDRFFPSS   540
GVLIFGKGTA TNKTTLENVL MTNEEEIRPT NPVATEEYGI VSSNLQAANT AAQTQVVNNQ   600
GALPGMVWQN RDVYLQGPIW AKIPHTDGNF HPSPLMGGFG LKHPPPQILI KNTPVPANPP   660
EVFTPAKFAS FITQYSTGQV SVEIEWELQK ENSKRWNPEI QYTSNFEKQT GVDFAVDSQG   720
VYSEPRPIGT RYLTRNL                                                 737

SEQ ID NO: 35           moltype = DNA  length = 2211
FEATURE                 Location/Qualifiers
```

| | | |
|---|---|---|
| source | 1..2211<br>mol_type = genomic DNA<br>organism = Adeno-associated virus | |

SEQUENCE: 35

```
atggctgccg atggttatct tccagattgg ctcgaggaca acctctctga gggcattcgc   60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gcaatcaccc aggaaccaga ctcctcttc gggcatcggc   480
aagaaaggcc agcagcccgc gaaaaagaga ctcaactttg gcagacagg cgactcagag   540
tcagtgccg accctcaacc actcggagaa ccccccgcag ccccctctgg tgtgggtct   600
aatacaatgg ctgcaggcgg tggcgctcca atggcagaca ataacgaagg cgccgacgga  660
gtgggtaacg cctcaggaaa ttggcattgc gattccacat ggctgggcga cagagtcatc  720
accaccagca cccgaacctg gccctccc acctacaaca accacctcta caagcaaatc   780
tccagccaat cgggagcaag caccaacact tcggctacag caccccctgg  840
gggtatttg actttaacag attccactgc cacttctcac cacgtgactg gcagcgactc   900
atcaacaaca actggggatt ccggcccaag agactcaact tcaagctctt caacatccag  960
gtcaaggagg tcacgacgaa tgatggcacc acgaccatcg ccataacct taccagcacg 1020
gttcaggtct ttacgactcg gaataccag ctcccgtacg tcctcggctc tgcgcaccag 1080
ggctgcctgc ctccgttcc ggcggacgtc ttcatgattc tcagtacgg gtacctgact  1140
ctgaacaatg gcagtcaggc cgtgggccgt tcctccttct actgcctgga gtactttcct 1200
tctcaaatgc tgagaacggg caacaacttt gagttcagct acacgtttga ggacgtgcct 1260
tttcacagca gctacgcgca cagccaaagc ctggaccggc tgatgaaccc cctcatcgac 1320
cagtacctgt actacctgtc tcggactcag accacgagtg gtaccgcagg aaatcggacg 1380
ttgcaattt tctcaggccg gcctagtagc atggcgaatc aggccaaaaa ctggctaccc 1440
gggccctgct accggcagca acgcgtctcc aagacagcga atcaaaataa caacagcaac 1500
tttgcctgga ccggtgccac caagtatcat ctgaatgca ggactctct ggtaaatcc  1560
ggtcccgcta tggcaaccca caaggacgac gaagacaaat tttttccgat gagcggagtc 1620
ttaatatttg gaaacagg agctggaaat agcaacgtgg accttgacaa cgttatgata  1680
accagtgagg aagaaattaa aaccaccaac ccagtggcca cagaacagta cggcacggtg  1740
gccactaacc tgcaatcgtc aaacaccgct cctgctacga ggacgtcaa cagtcaagga  1800
gccttacctg gcatggtctg gcagaaccgg gacgtgtacc tgcagggtcc tatctgggcc  1860
aagattcctc acacggacgg acactttcat ccctcgccgc tgatgggagg ctttggactg  1920
aaacacccgc ctcctcagat cctgattaag aatacacctg ttcccgcgaa tcctccaact 1980
accttcagtc cagctaagtt tgcgtcgttc atcacgcagt acagcaccgg acaggtcagc  2040
gtggaaattg aatgggagct gcagaaagaa aacagcaaac gctggaaccc agagattcaa  2100
tacacttcca actacaacaa atctacaaat gtggactttg ctgttgacac aaatgcgtt  2160
tattctgagc ctcgccccat cggcaccgt tacctcaccc gtaatctgta a          2211
```

| SEQ ID NO: 36<br>FEATURE<br>source | moltype = AA  length = 738<br>Location/Qualifiers<br>1..738<br>mol_type = protein<br>organism = Adeno-associated virus |
|---|---|

SEQUENCE: 36

```
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSTGI GKKGQQPAKK RLNFGQTGDS   180
ESVPDPQPIG EPPAGPSGLG SGTMAAGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQTSGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                                  738
```

| SEQ ID NO: 37<br>FEATURE<br>source | moltype = AA  length = 21<br>Location/Qualifiers<br>1..21<br>mol_type = protein<br>organism = Adeno-associated virus |
|---|---|

SEQUENCE: 37

```
EIKATNPVAT ERFGTVAVNF Q                                              21
```

| SEQ ID NO: 38<br>FEATURE<br>source | moltype = AA  length = 21<br>Location/Qualifiers<br>1..21<br>mol_type = protein<br>organism = Adeno-associated virus |
|---|---|

SEQUENCE: 38

```
EIKATNPVAT ERFGTVAVNL Q                                              21
```

| SEQ ID NO: 39 | moltype = AA  length = 21 |
|---|---|

-continued

| FEATURE | Location/Qualifiers |
|---|---|
| source | 1..21<br>mol_type = protein<br>organism = Adeno-associated virus |

SEQUENCE: 39
EIRTTNPVAT EQYGSVSTNL Q                                              21

| SEQ ID NO: 40 | moltype = AA  length = 21 |
|---|---|
| FEATURE | Location/Qualifiers |
| source | 1..21<br>mol_type = protein<br>organism = Adeno-associated virus |

SEQUENCE: 40
EIRTTNPVAT EQYGTVANNL Q                                              21

| SEQ ID NO: 41 | moltype = AA  length = 21 |
|---|---|
| FEATURE | Location/Qualifiers |
| source | 1..21<br>mol_type = protein<br>organism = Adeno-associated virus |

SEQUENCE: 41
EIRTTNPVAT EQYGTVATNL Q                                              21

| SEQ ID NO: 42 | moltype = AA  length = 21 |
|---|---|
| FEATURE | Location/Qualifiers |
| source | 1..21<br>mol_type = protein<br>organism = Adeno-associated virus |

SEQUENCE: 42
EIKTTNPVAT EQYGTVATNL Q                                              21

| SEQ ID NO: 43 | moltype = AA  length = 21 |
|---|---|
| FEATURE | Location/Qualifiers |
| VARIANT | 12<br>note = /replace="Glu" |
| REGION | 1..21<br>note = misc_feature - /note="Variant residues given in the<br>  sequence have no preference with respect to those in the<br>  annotations for variant positions" |
| source | 1..21<br>mol_type = protein<br>organism = Adeno-associated virus |

SEQUENCE: 43
EIKTTNPVAT EQYGTVATNL Q                                              21

| SEQ ID NO: 44 | moltype = AA  length = 6 |
|---|---|
| FEATURE | Location/Qualifiers |
| REGION | 1..6<br>note = source = /note="Description of Artificial Sequence:<br>  Synthetic 6xHis tag" |
| source | 1..6<br>mol_type = protein<br>organism = synthetic construct |

SEQUENCE: 44
HHHHHH                                                                6

What is claimed is:

1. A method comprising:
    administering a plurality of recombinant adeno-associated virus (rAAV) particles to a subject in need thereof,
    wherein each rAAV particle comprises (i) a transgene and (ii) one or more AAV capsid polypeptides that comprise an amino acid sequence according to SEQ ID NOs: 19, 20, 21, 22, 23, 24, 25, or 26, and
    wherein the transgene is within the rAAV particle.

2. The method of claim 1, wherein the one or more AAV capsid polypeptides comprises the amino acid sequence of SEQ ID NO: 19.

3. The method of claim 1, wherein the one or more AAV capsid polypeptides comprises the amino acid sequence of SEQ ID NO: 20.

4. The method of claim 1, wherein the one or more AAV capsid polypeptides comprises the amino acid sequence of SEQ ID NO: 21.

5. The method of claim 1, wherein the one or more AAV capsid polypeptides comprises the amino acid sequence of SEQ ID NO: 22.

6. The method of claim 1, wherein the one or more AAV capsid polypeptides comprises the amino acid sequence of SEQ ID NO: 23.

7. The method of claim 1, wherein the one or more AAV capsid polypeptides comprises the amino acid sequence of SEQ ID NO: 24.

8. The method of claim 1, wherein the one or more AAV capsid polypeptides comprises the amino acid sequence of SEQ ID NO: 25.

9. The method of claim 1, wherein the one or more AAV capsid polypeptides comprises the amino acid sequence of SEQ ID NO: 26.

10. The method of claim 1, wherein the method is a method of vaccinating the subject.

11. The method of claim 1, wherein the method is a method of delivering gene therapy to the subject.

12. The method of claim 1, wherein the subject is a human.

13. The method of claim 1, wherein the plurality of rAAV particles are administered in a composition comprising a pharmaceutically acceptable carrier.

14. The method of claim 1, wherein the plurality of rAAV particles transduces or infects cells in the subject.

15. The method of claim 14, wherein the cells are ear cells.

16. The method of claim 15, wherein the ear cells are inner ear cells.

17. The method of claim 1, wherein a therapeutically effective dose of the rAAV particles is administered.

18. A method of vaccinating or delivering gene therapy to a subject, the method comprising:
   administering a therapeutically effective dose of recombinant adeno-associated virus (rAAV) particles to a subject,
   wherein each rAAV particle comprises (i) a transgene and (ii) one or more AAV capsid polypeptides that comprise an amino acid sequence according to SEQ ID NOs: 19, 20, 21, 22, 23, 24, 25, or 26, and
   wherein the transgene is within the rAAV particle.

19. The method of claim 18, wherein the rAAV particles transduce or infect cells in the subject.

20. A method of delivering a transgene to a subject, the method comprising:
   obtaining recombinant adeno-associated virus (rAAV) particles, wherein each rAAV particle comprises (i) one or more AAV capsid polypeptides and (ii) a transgene located within the rAAV particle, wherein the one or more AAV capsid polypeptides comprise an amino acid sequence according to SEQ ID NO: 19, 20, 21, 22, 23, 24, 25, or 26; and
   administering to the subject in need thereof a therapeutically effective amount of the rAAV particles.

21. The method of claim 20, wherein obtaining the one or more rAAV particles comprises purifying.

\* \* \* \* \*